United States Patent
Shiomi et al.

(10) Patent No.: US 9,837,616 B2
(45) Date of Patent: Dec. 5, 2017

(54) AROMATIC AMINE DERIVATIVE, AND ORGANIC ELECTROLUMINESCENT ELEMENT CONTAINING SAME

(75) Inventors: Takushi Shiomi, Sodegaura (JP); Masami Watanabe, Sodegaura (JP); Mitsuru Eida, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 768 days.

(21) Appl. No.: 14/233,370

(22) PCT Filed: Jul. 23, 2012

(86) PCT No.: PCT/JP2012/004664
§ 371 (c)(1),
(2), (4) Date: Jan. 16, 2014

(87) PCT Pub. No.: WO2013/014908
PCT Pub. Date: Jan. 31, 2013

(65) Prior Publication Data
US 2014/0151677 A1 Jun. 5, 2014

(30) Foreign Application Priority Data
Jul. 26, 2011 (JP) .................. 2011-163171

(51) Int. Cl.
| | | |
|---|---|---|
| B32B 9/00 | (2006.01) | |
| H01L 51/00 | (2006.01) | |
| C07D 209/86 | (2006.01) | |
| C08G 61/12 | (2006.01) | |
| C07D 405/12 | (2006.01) | |
| H01L 51/50 | (2006.01) | |
| C08K 5/18 | (2006.01) | |

(52) U.S. Cl.
CPC ......... *H01L 51/006* (2013.01); *C07D 209/86* (2013.01); *C07D 405/12* (2013.01); *C08G 61/12* (2013.01); *C08G 61/124* (2013.01); *H01L 51/0059* (2013.01); *H01L 51/0061* (2013.01); *H01L 51/0072* (2013.01); *H01L 51/0095* (2013.01); *H01L 51/5012* (2013.01); *C08G 2261/124* (2013.01); *C08G 2261/3142* (2013.01); *C08G 2261/3162* (2013.01); *C08G 2261/3241* (2013.01); *C08G 2261/411* (2013.01); *C08G 2261/5222* (2013.01); *C08G 2261/95* (2013.01); *C08K 5/18* (2013.01); *H01L 51/0037* (2013.01); *H01L 51/5056* (2013.01)

(58) Field of Classification Search
CPC combination set(s) only.
See application file for complete search history.

(56) References Cited

U.S. PATENT DOCUMENTS

| | | |
|---|---|---|
| 2005/0100805 A1 | 5/2005 | Tanaka et al. |
| 2005/0208402 A1 | 9/2005 | Tanaka et al. |
| (Continued) | | |

FOREIGN PATENT DOCUMENTS

| | | |
|---|---|---|
| JP | 2004-109999 A | 4/2004 |
| JP | 2006-203172 A | 8/2006 |
| (Continued) | | |

OTHER PUBLICATIONS

Wong et al. ("Synthesis and properties of dumbbell-shaped dendrimers containing 9-phenylcarbazole dendron") provided with the Information Disclosure Statement filed Mar. 13, 2014.*

(Continued)

*Primary Examiner* — Austin Murata
(74) *Attorney, Agent, or Firm* — Foley & Lardner LLP

(57) ABSTRACT

An aromatic amine derivative represented by the following formula (1): wherein
$Z_1$ is a group represented by the following formula (2);
$Z_2$ is a group represented by the following formula (3) or (3'); and
P and Q are independently a group represented by the following formula (4) or (5):

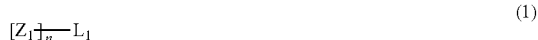

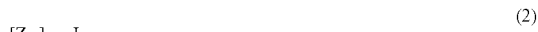

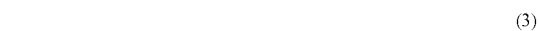

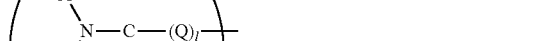

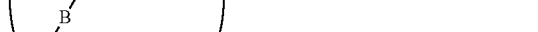

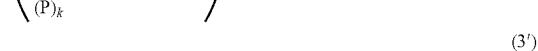

18 Claims, No Drawings

(56) References Cited

U.S. PATENT DOCUMENTS

2006/0134464 A1    6/2006  Nariyuki
2012/0013247 A1*   1/2012  Yi et al. ............... C08G 83/002
                                                           313/506

FOREIGN PATENT DOCUMENTS

| JP | 2007-110093 A | 4/2007 |
| JP | 2008-047935 A | 2/2008 |
| JP | 2008-198989 A | 8/2008 |
| JP | 2008-218983 A | 9/2008 |

OTHER PUBLICATIONS

International Preliminary Report on Patentability & Written Opinion in PCT/JP2012/004664 dated Feb. 6, 2014.
International Search Report in PCT/JP2012/004664 dated Sep. 25, 2012.
Wong et al., "Synthesis and Properties of Dumbell-Shaped Dendrimers Containing 9-Phenylcarbazole Dendrons", Organic Letters; 2007, vol. 9, p. 4531-4534.

* cited by examiner

AROMATIC AMINE DERIVATIVE, AND ORGANIC ELECTROLUMINESCENT ELEMENT CONTAINING SAME

This application is a National Phase of PCT/JP2012/004664, filed Jul. 23, 2012, which claims priority from Japanese Patent Application No. 2011-163171, filed Jul. 26, 2011 the disclosures of which are hereby incorporated by reference in their entirety.

TECHNICAL FIELD

The invention relates to an aromatic amine derivative, and an organic electroluminescence device containing the same.

BACKGROUND ART

Recently, a display and a lighting device using an organic electroluminescence device (organic EL device) have been actively studied for their practical realization. In particular, reducing the cost and sizing up of a display is given as a big issue to be solved. Under such circumstances, the (solution) coating type organic EL device has come to attract more expectations than ever as compared with traditional vacuum deposition type organic EL devices. It is expected that a coating type organic EL device has a high material-use efficiency, is easy in formation of a large-sized display, and is inexpensive regarding the apparatus cost due to elimination of a vacuum system.

Here, the organic EL material for a coating type organic device is divided into the low molecular-based one and the high molecular-based one. In respect of solubility, uniform coating and capability of being formed into a stacked device, a high molecular-based one is preferable. In particular, the development of high molecular-based materials for a hole transporting (injecting) layer which can be used both in a display and a lighting device has been desired.

As for the high molecular-based material for a hole transporting (injecting) layer, one disclosed in Patent documents 1 to 3 can be given. However, these materials provide insufficient hole transporting function (mobility) or insufficient solubility in a coating solvent.

In addition, coating type materials for a hole transporting (injecting) layer are disclosed in Patent documents 4 and 5, in which a polymerizable monomer which is substituted by a vinyl group or the like is applied to a triarylamine-based hole-transporting material, followed by a treatment such as heating to obtain a polymer, whereby a material for a hole transporting (injecting) layer which is insoluble in a solvent of an emitting layer is disclosed (Patent Documents 4 and 5). However, an organic EL device having a hole transporting (injecting) layer obtained from the above-mentioned polymerizable monomer cannot provide sufficient device properties such as a prolonged life (half life) and a high luminous efficiency.

RELATED ART DOCUMENTS

Patent Documents

[Patent Document 1] JP-2006-203172-A
[Patent Document 2] JP-2007-110093-A
[Patent Document 3] JP-2008-47935-A
[Patent Document 4] JP-2008-198989-A
[Patent Document 5] JP-2008-218983-A

SUMMARY OF THE INVENTION

An object of the invention is to provide an aromatic amine derivative having high heat resistance, amorphous property and high solubility in a solvent, and a high hole mobility suitable for being used in a hole-injecting/transporting material.

An object of the invention is to provide a novel polymerizable monomer having a polymerizable functional group, a polymer derived from the monomer through heat polymerization or the like, which the polymer is suitable as a material for a coating type organic device, in particular a hole-injecting/transporting material with which a hole-injecting/transporting layer can be uniformly formed.

Another object of the invention is to provide an organic EL device which is suitable for practical use, i.e. can be driven at high temperatures, have excellent device properties such as a prolonged life and a high luminous efficiency.

According to the invention, the following aromatic amine derivative and the like are provided.

1. An aromatic amine derivative represented by the following formula (1):

wherein $Z_1$ is a group represented by the following formula (2);

$L_1$ is a linkage group, and may have one or more substituents; and n is an integer of 2 to 10:

wherein $Z_2$ is a group represented by the following formula (3) or (3');

$L_2$ is a linkage group, and may have one or more substituents;

$L_1$ in the formula (1) bonds to any of $Z_2$ and $L_2$; and m is an integer of 2 to 10:

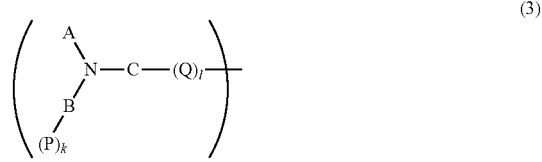

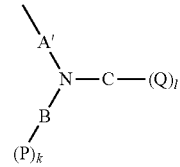

wherein in the formulas (3) and (3'),

A is a hydrogen atom, a substituted or unsubstituted aromatic hydrocarbon group having 6 to 25 ring carbon atoms that form a ring (hereinafter referred to as the "ring carbon atoms"), a substituted or unsubstituted aromatic heterocyclic group having 5 to 25 atoms that form a ring (hereinafter referred to as the "ring atoms") or a group formed of plural rings;

A' is a single bond, a substituted or unsubstituted aromatic hydrocarbon group having 6 to 25 ring carbon atoms, a substituted or unsubstituted aromatic heterocyclic group having 5 to 25 ring atoms or a group formed of plural rings;

B is a single bond, a substituted or unsubstituted aromatic hydrocarbon group having 6 to 25 ring carbon atoms, a substituted or unsubstituted aromatic heterocyclic group having 5 to 25 ring atoms or a group formed of plural rings;

C is a single bond, a substituted or unsubstituted aromatic hydrocarbon group having 6 to 25 ring carbon atoms, a substituted or unsubstituted aromatic heterocyclic group having 5 to 25 ring atoms or a group formed of plural rings;

P and Q are independently a substituted or unsubstituted aromatic hydrocarbon group having 6 to 25 ring carbon atoms, a substituted or unsubstituted aromatic heterocyclic group having 5 to 25 ring atoms, a group formed of plural rings or a group represented by the following formula (4) or (5);

$L_2$ in the formula (3) bonds to any of A, B, C, P and Q, and $L_2$ in the formula (3') bonds to A'; and k and l are independently an integer of 0 or 1, and k+l≥1:

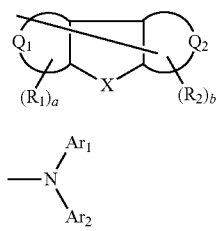

(4)

(5)

wherein in the formula (4), X is —O—, —S—, or —N($R_a$)—, $R_a$ is an atom or a group selected from a hydrogen atom, a substituted or unsubstituted linear or branched alkyl group having 1 to 20 carbon atoms, a substituted or unsubstituted linear or branched alkenyl group having 2 to 20 carbon atoms, a substituted or unsubstituted cycloalkyl group having 3 to 20 carbon atoms, a trialkylsilyl group of which the alkyl parts are each a substituted or unsubstituted alkyl group having 1 to 20 carbon atoms, a triarylsilyl group of which the aryl parts are each a substituted or unsubstituted aryl group having 6 to 24 ring carbon atoms, an alkylarylsilyl group having a substituted or unsubstituted alkyl group having 1 to 20 carbon atoms and a substituted or unsubstituted aryl group having 6 to 24 ring carbon atoms, a substituted or unsubstituted aryl group having 6 to 25 ring carbon atoms and a substituted or unsubstituted heteroaryl group having 5 to 24 ring atoms;

$R_1$ and $R_2$ are independently an atom or a group selected from a substituted or unsubstituted linear or branched alkyl group having 1 to 20 carbon atoms, a substituted or unsubstituted linear or branched alkenyl group having 2 to 15 carbon atoms, a substituted or unsubstituted cycloalkyl group having 3 to 20 carbon atoms, a trialkylsilyl group of which the alkyl parts are each a substituted or unsubstituted alkyl group having 1 to 20 carbon atoms, a triarylsilyl group of which the aryl parts are each a substituted or unsubstituted aryl group having 6 to 24 ring carbon atoms, an alkylarylsilyl group having a substituted or unsubstituted alkyl group having 1 to 20 carbon atoms and a substituted or unsubstituted aryl group having 6 to 24 ring carbon atoms, a substituted or unsubstituted aryl group having 6 to 24 ring carbon atoms, a substituted or unsubstituted heteroaryl group having 5 to 24 ring atoms, a halogen atom and a cyano group, and adjacent plural $R_1$s, adjacent plural $R_2$s, and/or adjacent $R_1$ and $R_2$ may bond to each other to form a saturated or unsaturated ring;

a and b are independently an integer of 0 to 3 and $Q_1$ and $Q_2$ are independently a group having 5 to 25 atoms which forms a saturated or unsaturated ring;

in the formula (5), $Ar_1$ and $Ar_2$ are independently a substituted or unsubstituted aromatic hydrocarbon group having 6 to 25 ring carbon atoms or a substituted or unsubstituted aromatic heterocyclic group having 5 to 25 ring atoms, and at least one of $Ar_1$ and $Ar_2$ is a group formed of plural rings having 9 to 40 ring carbon atoms or a fused aromatic ring group having 10 to 25 ring carbon atoms.

2. The aromatic amine derivative according to 1, wherein one or more selected from $L_1$, $L_2$, A and A' is a linkage group or a group comprising a group represented by any of the following formulas:

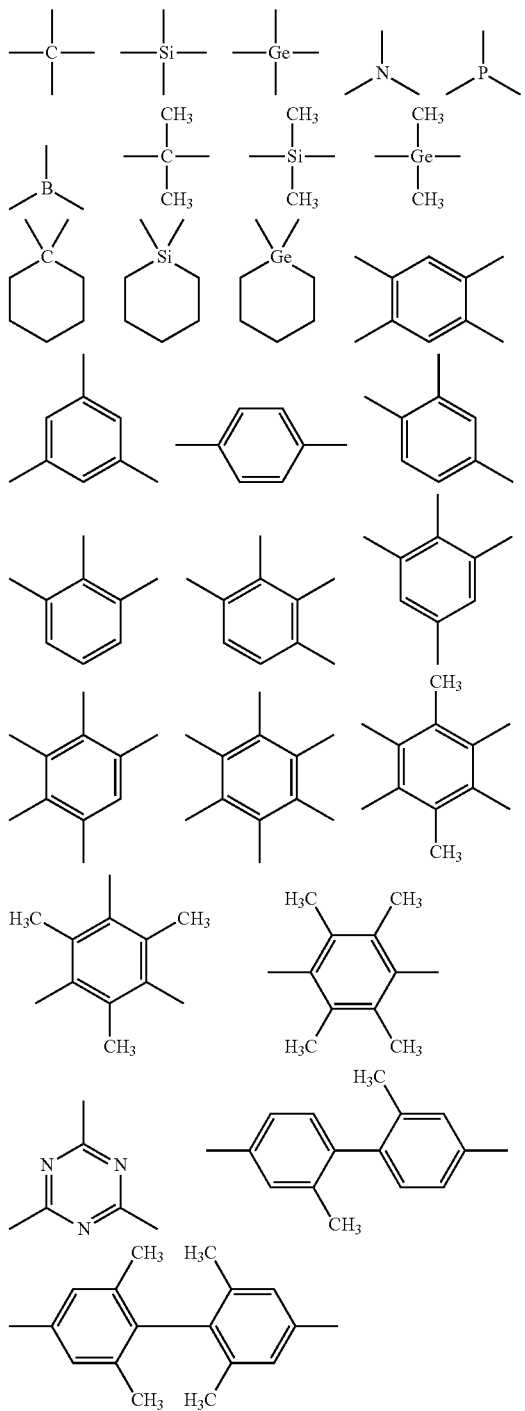

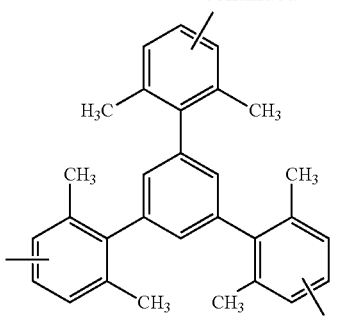
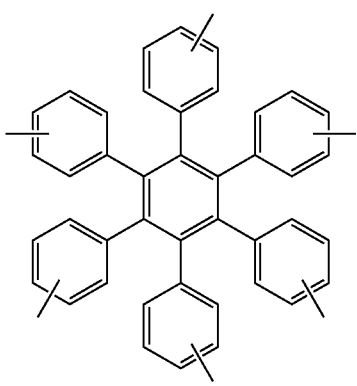
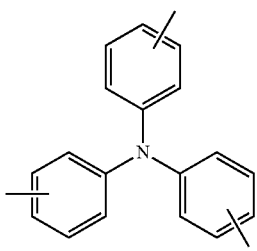
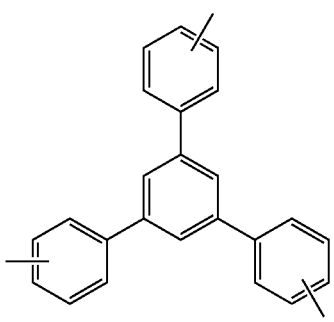
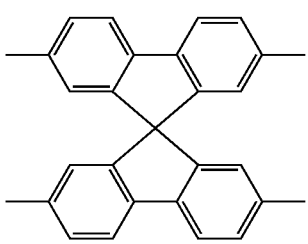

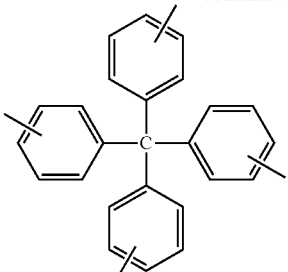
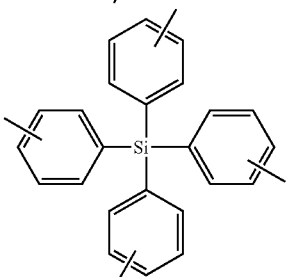
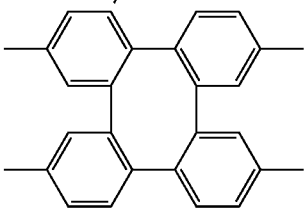

wherein $R_3$ and $R_4$ are independently a hydrogen atom, a methyl group, an ethyl group, a propyl group, an isopropyl group, a butyl group, an isobutyl group or a t-butyl group;

j is an integer of $2 \leq j \leq 20$, plural $R_3$s may be the same or different, and plural $R_4$s may be the same or different:

wherein $R_5$, $R_6$, $R_7$ and $R_8$ are independently a hydrogen atom, a liner or branched alkyl group having 1 to 20 carbon atoms, a liner or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

$R_5$ and $R_6$ and/or $R_7$ and $R_8$ may be bonded to each other to form a saturated or unsaturated ring;

x and y are an integer of $1 \leq x \leq 3$ and an integer of $1 \leq y \leq 3$, respectively, and when x is 2 or 3, plural $R_7$s may be the same or different, and when y is 2 or 3, plural $R_8$s may be the same or different:

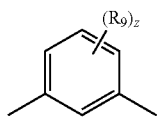

wherein $R_9$ is a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms; and z is an integer of $1 \leq z \leq 4$ and when z is 2, 3 or 4, plural $R_9$s may be the same or different:

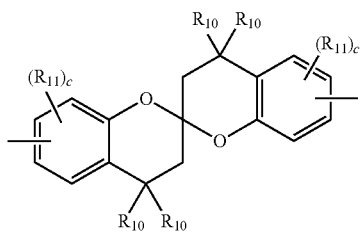

wherein $R_{10}$ and $R_{11}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

plural $R_{10}$s and/or plural $R_{11}$s may be bonded to each other to form a saturated or unsaturated ring; and c is an integer of $1 \leq c \leq 3$, and when c is 2 or 3, plural $R_{11}$s may be the same or different.

3. The aromatic amine derivative according to 1 or 2, wherein one or more selected from $L_1$, $L_2$, A and A' is a linkage group or a group comprising a group that interrupts conjugation between N atoms.

4. The aromatic amine derivative according to 3, wherein the linkage group or the group comprising a group that interrupts conjugation between N atoms is a linkage group or a group comprising a group represented by any of the following formulas:

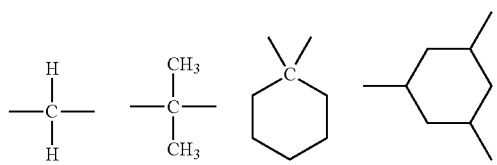

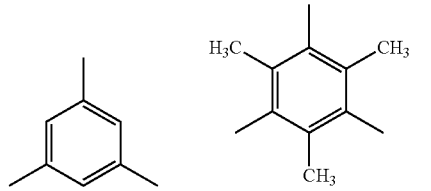

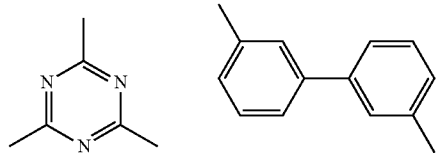

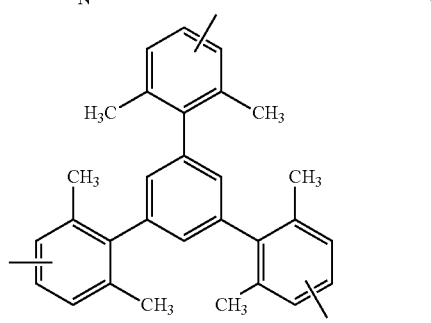

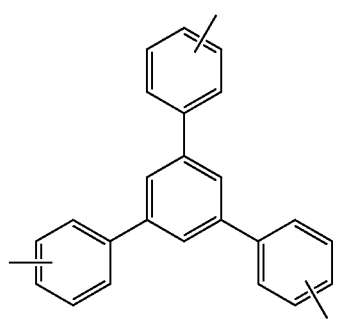

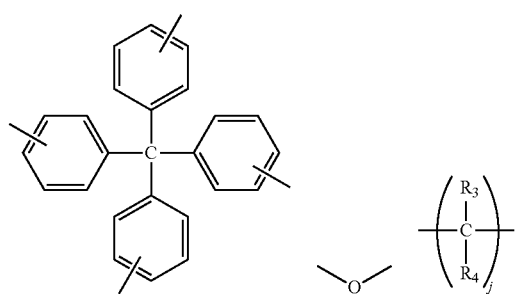

wherein $R_3$ and $R_4$ are independently a hydrogen atom, a methyl group, an ethyl group, a propyl group, an isopropyl group, a butyl group, an isobutyl group or a t-butyl group, and j is an integer of $2 \leq j \leq 20$, plural $R_3$s may be the same or different, and plural $R_4$s may be the same or different:

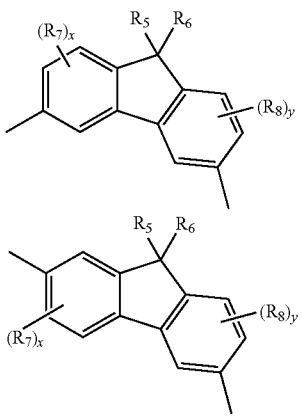

wherein $R_5$, $R_6$, $R_7$ and $R_8$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

$R_5$ and $R_6$ and/or $R_7$ and $R_8$ may be bonded to each other to form a saturated or unsaturated ring; and x and y are an integer of $1 \leq x \leq 3$ and an integer of $1 \leq y \leq 3$, respectively, and when x is 2 or 3, plural $R_7$s may be the same or different, and when y is 2 or 3, plural $R_8$s may be the same or different:

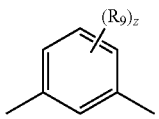

wherein $R_9$ is a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms; and z is an integer of $1 \leq z \leq 4$, and when z is 2, 3 or 4, plural $R_9$s may be the same or different:

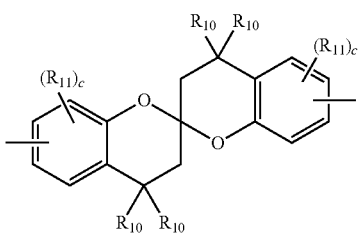

wherein $R_{10}$ and $R_{11}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

plural $R_{10}$s and/or plural $R_{11}$s may be bonded to each other to form a saturated or unsaturated ring; and c is an integer of $1 \leq c \leq 3$, and when c is 2 or 3, plural $R_{11}$s may be the same or different.

5. The aromatic amine derivative according to any of 1 to 4, wherein P and/or Q is independently a group represented by the following formula (6) or (7):

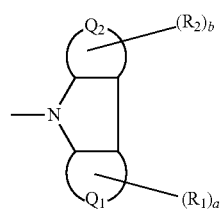

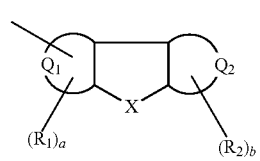

wherein $R_1$, $R_2$, a, b, $Q_1$ and $Q_2$ are as defined in the formula (4); and X is —O—, —S—, or —N($R_a$)—, and $R_a$ is as defined in the formula (4).

6. The aromatic amine derivative according to any of 1 to 5, wherein P and/or Q is independently a group represented by the following formula (8):

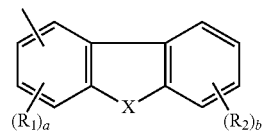

wherein $R_1$, $R_2$, a and b are as defined in the formula (4); and

X is —O—, —S—, or —N($R_a$)—, and $R_a$ is as defined in the formula (4).

7. The aromatic amine derivative according to any of 1 to 6, wherein P and/or Q is independently a group represented by the following formula (8-1) or (8-2):

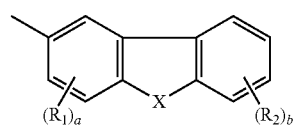

-continued

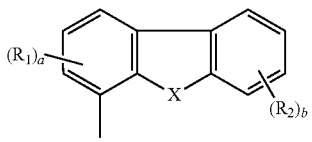
(8-2)

wherein $R_1$, $R_2$, a and b are as defined in the formula (4); and X is —O—, —S—, or —N($R_a$)—, and $R_a$ is as defined in the formula (4).

8. The aromatic amine derivative according to any of 1 to 7, wherein at least one of $L_1$, $L_2$, A, A', B, C, P and Q is bonded to a group comprising a polymerizable functional group.

9. The aromatic amine derivative according to 8, wherein the group comprising a polymerizable functional group is
  a group comprising a vinyl group, a vinylidene group, a vinylene group or an ethynylene group represented by the following formula (i);
  a group comprising a benzocyclobutene group represented by the following formula (ii);
  a group comprising an N-maleimide group represented by the following formula (iii);
  a group comprising a norbornenyl group represented by the following formula (iv);
  a group comprising an acetylenyl group represented by the following formula (v); or
  (vi) a group comprising a functional group capable of cyclopolymerization or ring-opening polymerization selected from the group consisting of a group having a substituted or unsubstituted norbornene skeleton other than a group represented by the formula (iv), a group having a substituted or unsubstituted epoxy group or an oxetane group, a functional group having a lactone structure or a lactam structure, a cyclooctatetraene group, a 1,5-cyclooctadiene group, a 1,ω-diene group, an O-divinylbenzene group and a 1, ω-diyne group:

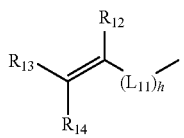
(i)

wherein $R_{12}$, $R_{13}$ and $R_{14}$ are independently a hydrogen atom, a fluorine atom, a substituted or unsubstituted linear or branched alkyl group having 1 to 20 carbon atoms, or a substituted or unsubstituted aryl group having 6 to 24 ring carbon atoms;
  $L_{11}$ is a linkage group; and
  h is an integer of 0 or 1, and when h is 0, $L_{11}$ is a single bond:

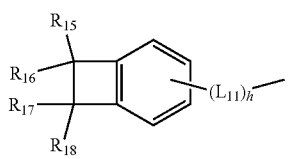
(ii)

wherein $R_{15}$, $R_{16}$, $R_{17}$ and $R_{18}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;
  $R_{15}$ and $R_{16}$, $R_{16}$ and $R_{17}$, and/or $R_{17}$ and $R_{18}$ may be bonded to each other to form a saturated or unsaturated ring,
  $L_{11}$ is a linkage group; and
  h is an integer of 0 or 1, and when h is 0, $L_{11}$ is a single bond:

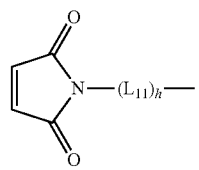
(iii)

wherein $L_{11}$ is a linkage group; and
  h is an integer of 0 or 1, and when h is 0, $L_{11}$ is a single bond:

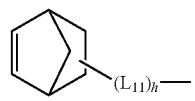
(iv)

wherein $L_{11}$ is a linkage group; and
  h is an integer of 0 or 1, and when h is 0, $L_{11}$ is a single bond:

(v)

wherein $R_{19}$ is a hydrogen atom, a substituted or unsubstituted linear or branched alkyl group having 1 to 20 carbon atoms, or a substituted or unsubstituted aryl group having 6 to 24 ring carbon atoms,
  $L_{11}$ is a linkage group; and
  h is an integer of 0 or 1, and when h is 0, $L_{11}$ is a single bond.

10. An organic electroluminescence device comprising one or more organic thin film layers including at least an emitting layer between a cathode and an anode, wherein at least one layer of the organic thin film layers comprises a polymer containing one or more types of repeating units derived from the aromatic amine derivative according to any of 1 to 9 and/or the amine derivative according to any of 1 to 9.

11. The organic electroluminescence device according to 10, wherein
  the organic thin film layers comprise at least one layer of a hole-transporting layer and a hole-injecting layer, and
  the at least one layer of a hole-transporting layer and a hole-injecting layer comprises the polymer.

According to the invention, an aromatic amine derivative having high heat resistance, amorphous property and high solubility in a solvent, and a high hole mobility suitable as a hole-injecting/transporting material can be obtained.

According to the invention, a novel polymerizable monomer having a polymerizable functional group and a material for a coating-type organic device obtained by subjecting the monomer to a heat polymerization or the like can be obtained. In particular, a polymer suitable for use as a hole-injection/transporting material which is capable of forming a hole-injection/transporting layer uniformly can be obtained.

According to the invention, an organic EL device which is suitable for practical use, i.e. can be driven at high temperatures, have excellent device properties such as a prolonged life and a high luminous efficiency is obtained.

BEST MODE FOR CARRYING THE INVENTION

The aromatic amine derivative of the invention is represented by the following formula (1): An aromatic amine derivative represented by the following formula (1):

$$[Z_1]_nL_1 \quad (1)$$

wherein $Z_1$ is a group represented by the following formula (2);

$L_1$ is a linkage group, and may have one or more substituents; and n is an integer of 2 to 10:

$$[Z_2]_mL_2 \quad (2)$$

wherein $Z_2$ is a group represented by the following formula (3) or (3');

$L_2$ is a linkage group, and may have one or more substituents;

$L_1$ in the formula (1) bonds to any of $Z_2$ and $L_2$; and m is an integer of 2 to 10:

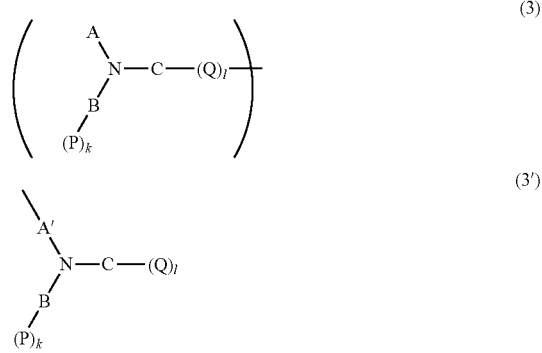

wherein in the formula (3), $L_2$ is bonded to any of A, B, C, P and Q, and in the formula (3)', $L_2$ is bonded to A';

A is a hydrogen atom, a substituted or unsubstituted aromatic hydrocarbon group having 6 to 25 ring carbon atoms, a substituted or unsubstituted aromatic heterocyclic group having 5 to 25 ring atoms or a group formed of plural rings;

A' is a single bond, a substituted or unsubstituted aromatic hydrocarbon group having 6 to 25 ring carbon atoms, a substituted or unsubstituted aromatic heterocyclic group having 5 to 25 ring atoms or a group formed of plural rings;

B is a single bond, a substituted or unsubstituted aromatic hydrocarbon group having 6 to 25 ring carbon atoms, a substituted or unsubstituted aromatic heterocyclic group having 5 to 25 ring atoms or a group formed of plural rings;

C is a single bond, a substituted or unsubstituted aromatic hydrocarbon group having 6 to 25 ring carbon atoms, a substituted or unsubstituted aromatic heterocyclic group having 5 to 25 ring atoms or a group formed of plural rings;

P and Q are independently a substituted or unsubstituted aromatic hydrocarbon group having 6 to 25 ring carbon atoms, a substituted or unsubstituted aromatic heterocyclic group having 5 to 25 ring atoms, a group formed of plural rings or a group represented by the following formula (4) or (5); and k and l are independently an integer of 0 or 1, and k+l≥1:

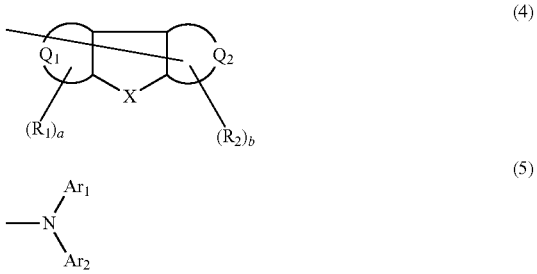

wherein in the formula (4), X is —O—, —S—, or —N($R_a$)—, $R_a$ is an atom or a group selected from a hydrogen atom, a substituted or unsubstituted linear or branched alkyl group having 1 to 20 carbon atoms, a substituted or unsubstituted linear or branched alkenyl group having 2 to 20 carbon atoms, a substituted or unsubstituted cycloalkyl group having 3 to 20 carbon atoms, a trialkylsilyl group of which the alkyl parts are each a substituted or unsubstituted alkyl group having 1 to 20 carbon atoms, a triarylsilyl group of which the aryl parts are each a substituted or unsubstituted aryl group having 6 to 24 ring carbon atoms, an alkylarylsilyl group having a substituted or unsubstituted alkyl group having 1 to 20 carbon atoms and a substituted or unsubstituted aryl group having 6 to 24 ring carbon atoms, a substituted or unsubstituted aryl group having 6 to 25 ring carbon atoms and a substituted or unsubstituted heteroaryl group having 5 to 24 ring atoms;

$R_1$ and $R_2$ are independently an atom or a group selected from a substituted or unsubstituted linear or branched alkyl group having 1 to 20 carbon atoms, a substituted or unsubstituted linear or branched alkenyl group having 2 to 15 carbon atoms, a substituted or unsubstituted cycloalkyl group having 3 to 20 carbon atoms, a trialkylsilyl group of which the alkyl parts are each a substituted or unsubstituted alkyl group having 1 to 20 carbon atoms, a triarylsilyl group of which the aryl parts are each a substituted or unsubstituted aryl group having 6 to 24 ring carbon atoms, an alkylarylsilyl group having a substituted or unsubstituted alkyl group having 1 to 20 carbon atoms and a substituted or unsubstituted aryl group having 6 to 24 ring carbon atoms, a substituted or unsubstituted aryl group having 6 to 24 ring carbon atoms, a substituted or unsubstituted heteroaryl group having 5 to 24 ring atoms, a halogen atom and a cyano group, and adjacent plural $R_1$s, adjacent plural $R_2$s, and/or adjacent $R_1$ and $R_2$ may bond to each other to form a saturated or unsaturated ring;

a and b are independently an integer of 0 to 3 and $Q_1$ and $Q_2$ are independently a group having 5 to 25 atoms which forms a saturated or unsaturated ring;

in the formula (5), $Ar_1$ and $Ar_2$ are independently a substituted or unsubstituted aromatic hydrocarbon group having 6 to 25 ring carbon atoms or a substituted or unsubstituted aromatic heterocyclic group having 5 to 25 ring atoms, and at least one of $Ar_1$ and $Ar_2$ is a group formed of plural rings having 9 to 40 ring carbon atoms, preferably 18 to 25 ring carbon atoms or a fused aromatic ring group having 10 to 25 ring carbon atoms.

The term of "plural rings" in "the group formed of plural rings" of A, A', B, C, P, Q, $Ar_1$ and $Ar_2$ means a structure in which two or more rings (two or more rings selected from single rings and fused rings of an aromatic hydrocarbon, and single rings and fused rings of an aromatic heterocyclic ring) are directly bonded to each other through a single bond or a double bond and the number of the direct bonding is smaller by 1 than that of the rings. For example, one obtained by bonding a benzene ring and a benzene ring, one obtained by bonding a benzene ring and a naphthalene ring, one obtained by bonding a benzene ring, a naphthalene ring and a pyridine ring, or the like can be given.

As for the group formed of plural rings, the bonding position to other groups than the plural rings may be any positions of any rings forming the plural rings.

The term "fused aromatic ring" used herein means one in which at least two rings are bonded to each other through two common atoms and at least one ring is an aromatic ring. Specific examples of the fused aromatic ring group include a naphthyl group, an anthryl group and a fluorenyl group.

The aromatic amine derivative of the invention loses the molecular planarity due to the presence of plural aromatic amine units $Z_1$ in a molecule, thereby to exhibit the solubility in a coating solvent and the amorphous property.

In addition, when the aromatic amine derivative comprise the polymerizable functional group described later, since the molecular weight can be increased, high heat resistance (high Tg: high glass-transition temperature) can be obtained. Thus, if a polymer film is derived from the derivative by a high temperature treatment, the coating film does not tend to be crystallized easily, whereby a uniform film can be formed. As a result, it is possible to obtain an organic EL device which has excellent device properties such as a long life and a high luminous efficiency and is suitable for practical use. Specifically, it is possible to obtain an organic EL device which suffers only slight deterioration even when it is subjected to a high-temperature driving that is especially practical conducted in applications of a display or an illumination. Further, since a hole-injecting/transporting layer can be formed uniformly, the organic amine derivative of the invention is suitable for cost reduction or an increase in size in applications of displays and illuminations.

Due to the structure represented by the formula (4), the aromatic amine derivative of the invention has a wide band gap that enables electrons to be blocked, thereby allowing holes and electrons to recombine efficiently in an emitting layer. As a result, the ionization potential can be easily adjusted to a level that is suitable for injecting holes into the emitting layer, leading to a high mobility or the like for reducing the driving voltage.

Further, due to the structure represented by the formula (5), the aromatic amine derivative of the invention has a high heat resistance (high Tg: high glass-transition temperature). Coating solvents have normally a high boiling point. Therefore, a treatment at high temperatures is required for removal of a residual solvent after coating. Even if an aromatic amine derivative has a polymerizable functional group, described later and thus a polymer film is formed from the aromatic amine derivative during the treatment at high temperatures, the film may suffer disarrayed membrane interface or disordered molecular arrangement when the treatment temperature is over Tg. However, the structure of the invention can suppress such problems. As a result, an organic EL device having excellent device properties such as a prolonged lifetime and a high luminous efficiency can be obtained. In addition, the organic EL device which is suitable for practical use can be obtained; specifically, it is possible to obtain an organic EL device which suffers only a slight degree of deterioration even when it is subjected to a high-temperature driving that is especially practical conducted in applications of a display or an illumination.

In the formulas (1) to (3) and (3'), it is preferred that one or more selected from $L_1$, $L_2$, A and A' be a linkage group or a group including a group represented by any of the following groups. A' in the formula (3') is preferably a linkage group including a divalent group among the following groups.

The linkage group or group including the following group can allow plural aromatic amine units (hole-injecting/transporting unit) to be bonded to increase the amorphous property and the solubility in a solvent of the aromatic amine derivative, thereby enabling a large-size film to be formed by coating uniformly.

Further, when the aromatic amine derivative contains a polymerizable function group mentioned later, a polymer derived from the monomer (aromatic amine derivative) can be amorphous. By this, if the monomer is treated at high temperatures to be a film of a polymer, the coating film is hardly crystallized, whereby a uniform film can be formed. As a result, a practical organic EL device which has excellent device properties such as a prolonged lifetime and a high luminous efficiency, and suffers only a slight deterioration when it is subjected to a high-temperature driving, that is particularly practical in applications such as displays and illuminations, can be obtained. In addition, since a hole-injecting/transporting layer can be formed uniformly, the aromatic amine derivative of the invention is suitable for reducing the cost and increasing the display size in the applications of displays and illuminations.

It suffices that $L_1$, $L_2$, A and A' contain any of the following groups as the part of the structure. They may contain a group formed by repetition of plural identical groups of the following groups. They may also contain the following group formed by combination of plural different groups.

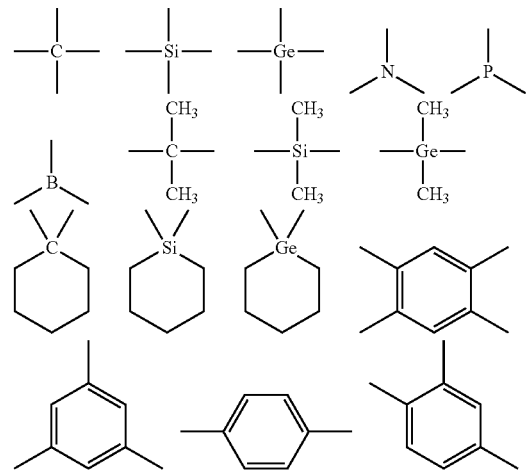

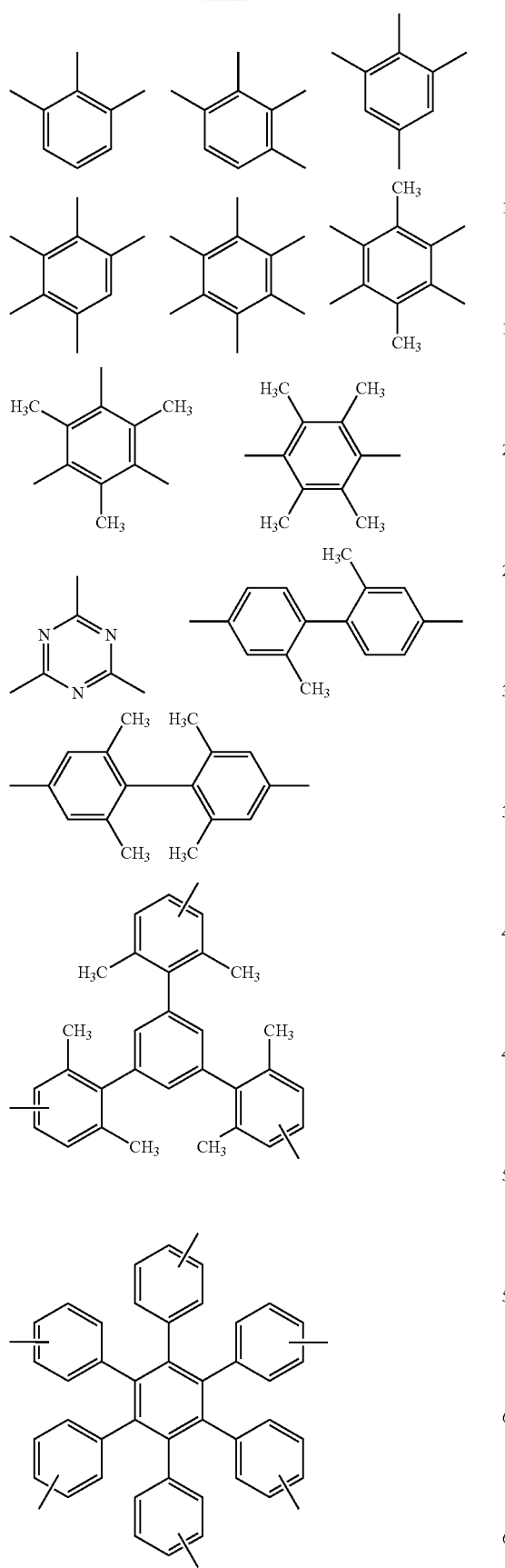
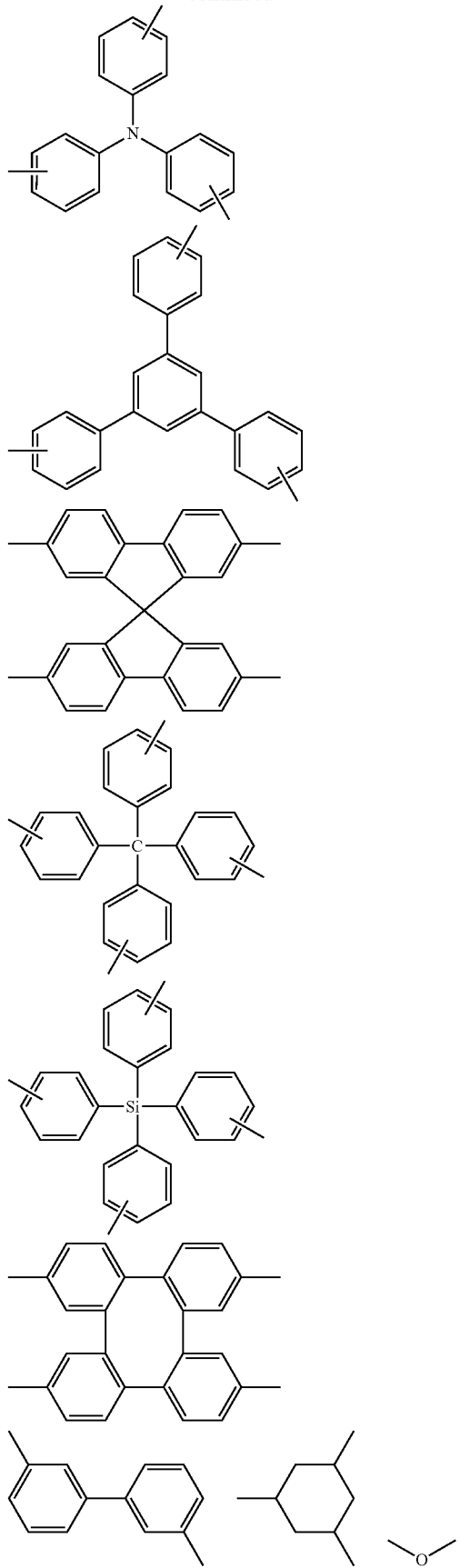

-continued

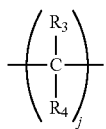

wherein $R_3$ and $R_4$ are independently a hydrogen atom, a methyl group, an ethyl group, a propyl group, an isopropyl group, a butyl group, an isobutyl group or a t-butyl group;

j is an integer of $2 \leq j \leq 20$, plural $R_3$s may be the same or different, and plural $R_4$s may be the same or different:

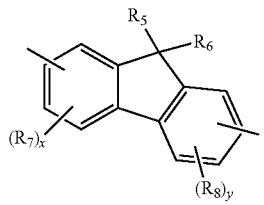

wherein $R_5$, $R_6$, $R_7$ and $R_8$ are independently a hydrogen atom, a liner or branched alkyl group having 1 to 20 carbon atoms, a liner or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

$R_5$ and $R_6$ and/or $R_7$ and $R_8$ may be bonded to each other to form a saturated or unsaturated ring;

x and y are an integer of $1 \leq x \leq 3$ and an integer of $1 \leq y \leq 3$, respectively, and when x is 2 or 3, plural $R_7$s may be the same or different, and when y is 2 or 3, plural $R_8$s may be the same or different:

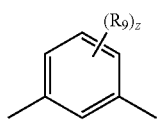

wherein $R_9$ is a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms; and z is an integer of $1 \leq z \leq 4$, and when z is 2, 3 or 4, plural $R_9$s may be the same or different:

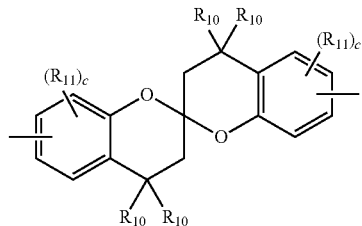

wherein $R_{10}$ and $R_{11}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

plural $R_{10}$s and/or plural $R_{11}$s may be bonded to each other to form a saturated or unsaturated ring; and c is an integer of $1 \leq c \leq 3$, and when c is 2 or 3, plural $R_{11}$s may be the same or different.

In the formulas (1) to (3) and (3)', one or more selected from $L_1$, $L_2$, A and A' is preferably a linkage group or a group comprising a group that interrupts conjugation between N atoms. Here, the "interrupt conjugation" means that the electron cloud of an unshared electron pair contained in an N atom does not overlap between plural N atoms.

The conjugation between hole-injecting/transporting units of plural $Z_1$ are interrupted since $L_1$, $L_2$, A and A' interrupt the conjugation of N atoms. As a result, the resulting polymer film can exhibit a wide band gap which can block electrons, thereby to recombine holes and electrons in an emitting layer efficiently and an ionization potential suitable for injecting holes into the emitting layer.

The linkage group comprising a group that interrupts conjugation between N atoms is preferably a linkage group comprising a group represented by any of the following formulas. When A' in the formula (3') is the linkage group comprising a group that interrupts conjugation between N atoms, the linkage group is preferably a linkage group comprising the following divalent group.

It suffices that the linkage group comprising a group that interrupts conjugation between N atoms contains any of the following groups as the part of the structure. It may contain the group formed by repetition of plural identical groups of the following groups. It may contain the following group formed by combination of plural different groups.

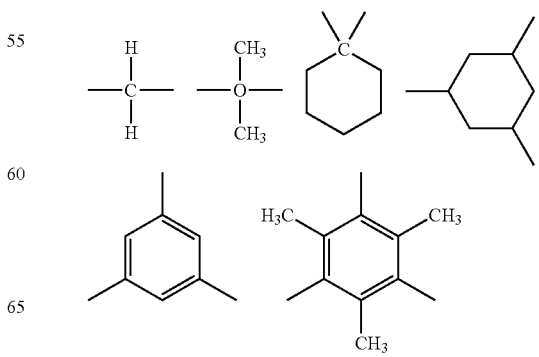

-continued

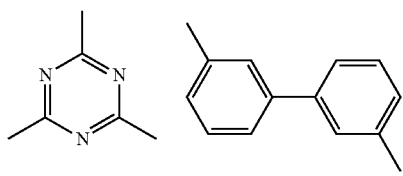

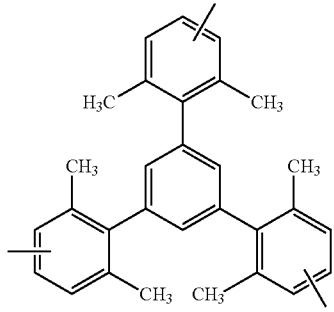

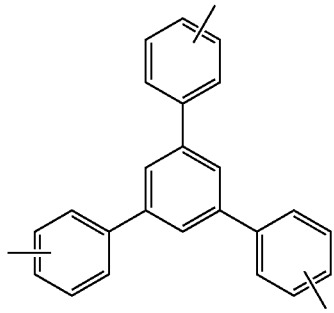

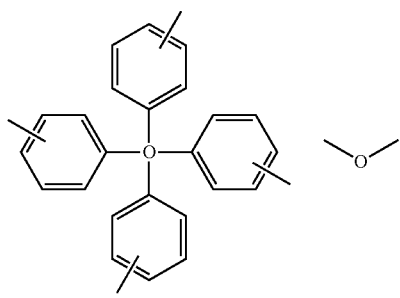

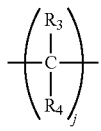

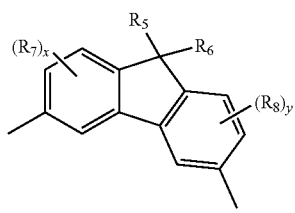

wherein R₃ and R₄ are independently a hydrogen atom, a methyl group, an ethyl group, a propyl group, an isopropyl group, a butyl group, an isobutyl group or a t-butyl group, and j is an integer of 2≤j≤20, plural R₃s may be the same or different, and plural R₄s may be the same or different:

-continued

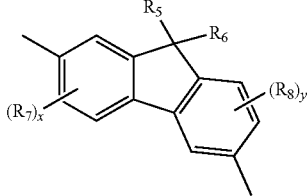

wherein R₅, R₆, R₇ and R₈ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

R₅ and R₆ and/or R₇ and R₈ may be bonded to each other to form a saturated or unsaturated ring; and x and y are an integer of 1≤x≤3 and an integer of 1≤y≤3, respectively, and when x is 2 or 3, plural R₇s may be the same or different, and when y is 2 or 3, plural R₈s may be the same or different:

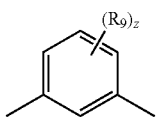

wherein R₉ is a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms; and z is an integer of 1≤z≤4, and when z is 2, 3 or 4, plural R₉s may be the same or different:

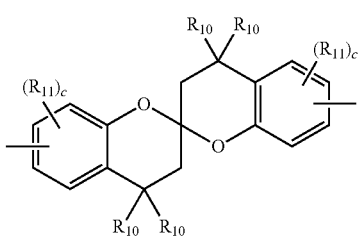

wherein R₁₀ and R₁₁ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

plural $R_{10}$s and/or plural $R_{11}$s may be bonded to each other to form a saturated or unsaturated ring; and c is an integer of $1 \leq c \leq 3$, and when c is 2 or 3, plural $R_{11}$s may be the same or different.

In the formula (3), P and/or Q is independently a group represented by the following formulas (6) or (7), preferably.

By allowing P and Q to be a monovalent group represented by the formula (6) or (7), the amorphous property can be improved while improving the electron resistance and hole mobility of an aromatic amine derivative. Further, when the aromatic amine derivative comprises a polymerizable functional group, the electron resistance, hole mobility and amorphous property of the resulting polymer film can be increased.

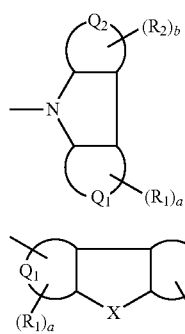

wherein $R_1$, $R_2$, a, b, $Q_1$ and $Q_2$ are as defined in the formula (4); and X is —O—, —S—, or —N($R_a$)—, and $R_a$ is as defined in the formula (4).

In the formula (3), P and/or Q is each preferably a group represented by the following formula (8):

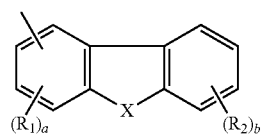

wherein $R_1$, $R_2$, a and b are as defined in the formula (4); and

X is —O—, —S—, or —N($R_a$)—, and $R_a$ is as defined in the formula (4).

In the formulas (3) and (3'), P and/or Q is preferably independently a group represented by the following formula (8-1) or (8-2).

By allowing P and/or Q to be a monovalent group represented by the formula (8-1) or (8-2), the synthesis and purification of the aromatic amine derivative can be easily conducted, thereby increasing the purity. As a result, the life of the resulting device such as an organic EL device can be prolonged. Further, when the aromatic amine derivative comprises a polymerizable functional group, the electron resistance, hole mobility and amorphous property of the resulting polymer film can be increased.

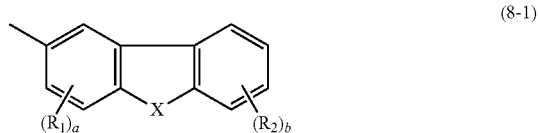

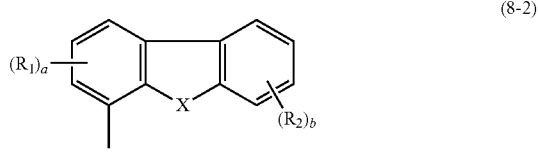

wherein $R_1$, $R_2$, a and b are as defined in the formula (4); and

X is —O—, —S—, or —N($R_a$)—, and $R_a$ is as defined in the formula (4).

The aromatic amine derivative of the invention is preferably a polymerizable monomer in which at least one of $L_1$, $L_2$, A, A', B, C, P and Q in the formulas (1) to (3) and (3') is bonded to a group comprising a polymerizable functional group.

Here, the "group comprising a polymerizable functional group" means a group comprising a functional group that can induce a chemical reaction in which two or more molecules of one unit compound are bonded to generate a compound having a molecular weight equal to the integral multiple of the unit compound.

The group comprising a polymerizable functional group is preferably bonded to $L_1$.

By substituting $L_1$ with the group comprising a polymerizable functional group, the group comprising a polymerizable functional group can be distant from a hole-injecting/transporting unit of $Z_1$ to reduce adverse effects exerted by a radical and/or cation as a polymerization reacting species on the hole-injecting/transporting unit. Further, when monomers are polymerized to be a polymer, the degree of freedom of the hole-injecting/transporting unit of $Z_1$ can be ensured. As a result, holes can transfer between molecules in the state similar to the low-molecular state. Therefore, even in the state of a polymer, the hole mobility can be easily maintained.

The aromatic amine derivative of the invention preferably comprises two or more polymerizable functional groups.

By allowing the aromatic amine derivative to comprise two or more polymerizable functional groups, the solubility of a polymerizable monomer in a coating solvent can be improved. When monomers are polymerized to be a polymer, the polymer becomes insoluble in a coating solvent of stacked emitting materials due to the presence of a cross-linked structure. As a result, an emitting device having a stacked structure can be obtained without causing an interfacial disorder between a hole-injecting/transporting layer and an emitting layer.

The above-mentioned group comprising a polymerizable functional group is a group comprising a vinyl group, a vinylidene group, a vinylene group or an ethynylene group represented by the following formula (i); a group comprising a benzocyclobutene group represented by the following formula (ii); a group comprising an N-maleimide group represented by the following formula (iii); a group comprising a norbornenyl group represented by the following formula (iv); a group comprising an acetylenyl group represented by the following formula (v); or (vi) a group comprising a functional group capable of cyclopolymerization or ring-opening polymerization selected from the group consisting of a group having a substituted or unsubstituted norbornene skeleton other than a group represented by the formula (iv), a group having a substituted or unsubstituted epoxy group or an oxetane group, a functional group having a lactone structure or a lactam structure, a cyclooctatetraene group, a 1,5-cyclooctadiene group, a 1,ω-diene group, an O-divinylbenzene group and a 1,ω-diyne group:

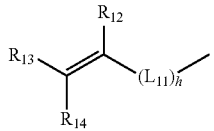

(i)

wherein $R_{12}$, $R_{13}$ and $R_{14}$ are independently a hydrogen atom, a fluorine atom, a substituted or unsubstituted linear or branched alkyl group having 1 to 20 carbon atoms, or a substituted or unsubstituted aryl group having 6 to 24 ring carbon atoms;

$L_{11}$ is a linkage group; and h is an integer of 0 or 1, and when h is 0, $L_{11}$ is a single bond:

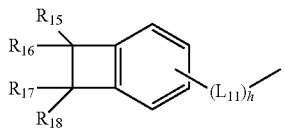

(ii)

wherein $R_{15}$, $R_{16}$, $R_{17}$ and $R_{18}$ are independently a hydrogen atom, a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms or a heteroaryl group having 5 to 24 ring atoms;

$R_{15}$ and $R_{16}$, $R_{16}$ and $R_{17}$, and/or $R_{17}$ and $R_{18}$ may be bonded to each other to form a saturated or unsaturated ring, $L_{11}$ is a linkage group; and h is an integer of 0 or 1, and when h is 0, $L_{11}$ is a single bond:

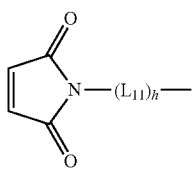

(iii)

wherein $L_{11}$ is a linkage group; and h is an integer of 0 or 1, and when h is 0, $L_{11}$ is a single bond:

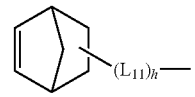

(iv)

wherein $L_{11}$ is a linkage group; and h is an integer of 0 or 1, and when h is 0, $L_{11}$ is a single bond:

(v)

wherein $R_{19}$ is a hydrogen atom, a substituted or unsubstituted linear or branched alkyl group having 1 to 20 carbon atoms, or a substituted or unsubstituted aryl group having 6 to 24 ring carbon atoms, $L_{11}$ is a linkage group; and h is an integer of 0 or 1, and when h is 0, $L_{11}$ is a single bond.

In the formulas (i) to (v), the divalent linkage group represented by $L_{11}$ includes any one of divalent linkage groups represented by $L_{12}$-, —O—, —C(=O)—, —C(=O)O—, —OC(=O)—, —C(=O)NR$_{15}$—, —NR$_{16}$C(=O)—, —NR$_{17}$—, —S— and —C(=S)—, or a linkage group obtained by bonding two or more of these linkage groups in an arbitral order.

$L_{12}$ is a linkage group selected from the group consisting of a substituted or unsubstituted arylene group having 6 to 24 ring carbon atoms, a substituted or unsubstituted divalent heterocyclic group having 3 to 24 ring atoms, a substituted or unsubstituted linear or branched alkylene group having 1 to 20 carbon atoms, a substituted or unsubstituted vinylene group, a substituted or unsubstituted vinylidene group and an ethynylene group, or a linkage group obtained by bonding two or more groups selected from the above-mentioned group in an arbitral order. $R_{15}$ to $R_{17}$ are independently selected from the group consisting of a hydrogen atom, a substituted or unsubstituted linear or branched alkyl group having 1 to 20 carbon atoms and a substituted or unsubstituted aryl group having 6 to 24 ring carbon atoms.

By allowing $L_{11}$ to be the above-mentioned linkage group, the solubility of a monomer in a coating solvent is improved, the rate of polymerization reaction becomes high, and the amount of unreacted monomers is decreased. As a result, an organic device, in particular an organic EL device, can be improved for the durability and life time.

$L_{12}$ is preferably a linkage group comprising a substituted or unsubstituted linear or branched alkylene group having 3 to 12 carbon atoms.

$L_{12}$ comprising a substituted or unsubstituted linear or branched alkylene group having 3 to 12 carbon atoms can increase the solubility of the monomer in a coating solvent. At the same time, the hole-injecting/transporting unit of $Z_1$ is separated from the part where polymerization reaction occurs by the polymerizable function group, thereby to suppress adverse effects exerted by a radical and a cation as polymerization reaction species. In addition, the increased degree of freedom of the polymerizable function group enhances the rate of polymerization reaction and reduces the amount of unreacted monomers. Therefore, a radical and/or a cation derived from unreacted monomers which may exert adverse effects on an organic device during the driving thereof, in particular an organic EL device, is reduced, whereby the durability and the lifetime thereof can be improved. When monomers are polymerized to be a polymer, the degree of freedom of the hole-injecting/transporting unit of $Z_1$ enables the hole transfer between molecules to be conducted in the state similar to that of a low molecular polymer, whereby even a polymer can easily remain the hole mobility.

An alkylene group is a divalent group obtained by drawing out two hydrogen atoms from an alkyl group. In the case of an alkylene group having less than 3 carbon atoms, the above-mentioned effects may be small. In the case of an alkylene group having more than 12 carbon atoms, increasing insulating components may reduce the hole-transporting functional capability, whereby in an organic device, in particular an organic EL device, the efficiency may be easily lowered (increasing voltage) or the heat resistance may be lowered (decreasing glass-transition temperature).

As the group of (vi), a group having a substituted or unsubstituted epoxy group or an oxetane group is preferable. When the group comprising a polymerization functional group is a group of (vi), the polymerization reaction can be conducted at low temperatures, whereby adverse effects induced by heat on a hole-injecting/transporting unit can be suppressed.

Specific examples of the group constituting the compound represented by the formulas (1) to (8) will be explained below.

In the invention, the term "aryl group" means the "group obtained by removing a hydrogen atom from an aromatic hydrocarbon compound". The aryl group includes not only the "aryl group" which is monovalent but also the "arylene group" which is divalent. When the group constituting the compound represented by the formulas (1) to (8) is a group having two or more valences, it is a residue corresponding to the following specific examples of the aryl group. The aryl group is also referred to as an "aromatic hydrocarbon group" or an "aromatic hydrocarbon residue".

The term "heteroaryl group" means a "group obtained by removing a hydrogen atom from an aromatic heterocyclic compound". The heteroaryl group includes not only the "heteroaryl group" which is monovalent but also the "heteroarylene group" which is divalent. When the group constituting the compound represented by the formulas (1) to (8) is a group having two or more valences, it is a residue corresponding to the following specific examples of the heteroaryl group. The heteroaryl group is also referred to as an "aromatic heterohydrocarbon group", an "aromatic heterohydrocarbon residue" or an "aromatic heterocyclic group".

In the invention, the "hydrogen atom" includes deuterium and tritium.

As the substituted or unsubstituted aryl group (aromatic hydrocarbon group), a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a biphenyl-2-yl group, a biphenyl-3-yl group, a biphenyl-4-yl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenyl-4-yl group, a 4"-t-butyl-p-terphenyl-4-yl group, a fluorene-1-yl group, a fluorene-2-yl group, a fluorene-3-yl group, a fluorene-4-yl group or the like can be given.

Of these, a phenyl group, a 1-naphthyl group, a 2-naphthyl group, a 1-anthryl group, a 2-anthryl group, a 9-anthryl group, a biphenyl-2-yl group, a biphenyl-3-yl group, a biphenyl-4-yl group, a p-terphenyl-4-yl group, a p-terphenyl-3-yl group, a p-terphenyl-2-yl group, an o-tolyl group, an m-tolyl group, a p-tolyl group, a fluorene-2-yl group and a fluorene-3-yl group are preferable, with a phenyl group, a 1-naphthyl group, a 2-naphthyl group, an m-tolyl group, a p-tolyl group, a fluorene-2-yl group and a fluorene-3-yl group being more preferable.

As the substituted or unsubstituted alkyl group, a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, an n-nonyl group, an n-decanyl group, an n-undecanyl group, an n-dodecanyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group or the like can be given. Preferably, a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group and an n-nonyl group can be given.

As the alkenyl group, a substituent having an unsaturated bond in the molecule of the above-mentioned alkyl group can be given.

As the substituted or unsubstituted cycloalkyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, a 2-norbornyl group or the like can be given. A cyclopentyl group and a cyclohexyl group are preferable.

As the trialkylsilyl group, a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group, a trihexysilyl group or the like can be given. A trimethylsilyl group and a triethylsilyl group are preferable.

The alkyl groups substituting a silyl group may be the same or different.

As the triarylsilyl group, a triphenylsilyl group, a trinaphthylsilyl group or the like can be given. A triphenylsilyl group is preferable.

The aryl groups substituting a silyl group may be the same or different.

As the alkylarylsilyl group, a dimethylphenylsilyl group, a diethylphenylsilyl group, a diphenylmethylsilyl group, an ethyldiphenylsilyl group or the like can be given. A diphenylmethylsilyl group and an ethyldiphenylsilyl group are preferable.

The alkyl and aryl groups substituting a silyl group may independently be the same or different.

As the substituted or unsubstituted heteroaryl group (aromatic heterocyclic group), a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methypyrrole-1-yl group, a 2-methypyrrole-3-yl group, a 2-methypyrrole-4-yl group, a 2-methypyrrole-5-yl group, a 3-methypyrrole-1-yl group, a 3-methypyrrole-2-yl group, a 3-methypyrrole-4-yl group, a 3-methypyrrole-5-yl group, a 2-t-butylpyrrole-4-yl group, a 3-(2-phenylpropyl) pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group or the like can be given.

Preferred are a 1-pyrrolyl group, a 2-pyrrolyl group, a 3-pyrrolyl group, a 1-carbazolyl group, a 2-carbazolyl group, a 3-carbazolyl group, a 4-carbazolyl group and a 9-carbazolyl group.

As the halogen atom, fluorine, chlorine and bromine can be given, and fluorine is preferable.

As the alkane residue and cycloalkane residue of $L_1$ and $L_2$, a residue corresponding to the above-mentioned alkyl group and cycloalkyl group can be given. As the trialkylamine residue, triarylamine residue and alkylarylmine residue of $L_1$ and $L_2$, the residue obtained by substituting amine with the above-mentioned aryl group and alkyl group can be given.

The substituent will be explained below.

The substituents relating to the "substituted or unsubstituted" are independently a linear or branched alkyl group having 1 to 20 carbon atoms, a linear or branched alkenyl group having 2 to 20 carbon atoms, a cycloalkyl group having 3 to 20 carbon atoms, a trialkylsilyl group having an alkyl group having 1 to 20 carbon atoms, a triarylsilyl group having an aryl group having 6 to 24 ring carbon atoms, an alkylarylsilyl group having an alkyl group having 1 to 20 carbon atoms and an aryl group having 6 to 24 ring carbon atoms, an aryl group having 6 to 24 ring carbon atoms, a heteroaryl group having 5 to 24 ring atoms, a halogen atom or a cyano group. Specifically, the substituent is selected from the above-mentioned aryl group, alkyl group, alkenyl group, cycloalkyl group, trialkylsilyl group, triarylsilyl group, alkylarylsilyl group, heteroaryl group, a halogen atom and a cyano group. Specific examples of the above-mentioned alkyl group or the like are as described above.

The "substituent" in the case where $L_1$ and $L_2$ have a substituent are also as described above.

Specific examples of the aromatic amine derivative of the invention will be shown below. However, the aromatic amine derivative of the invention is not limited thereto.

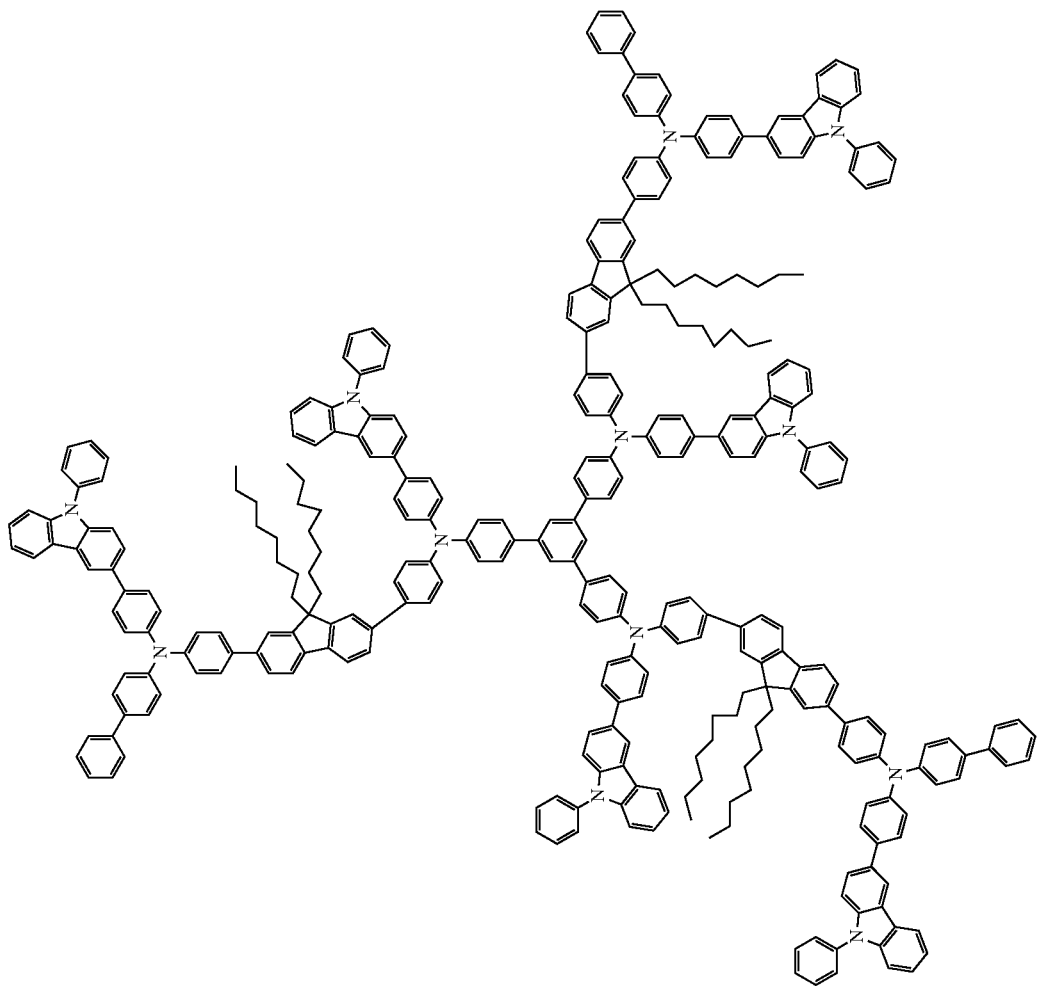

-continued
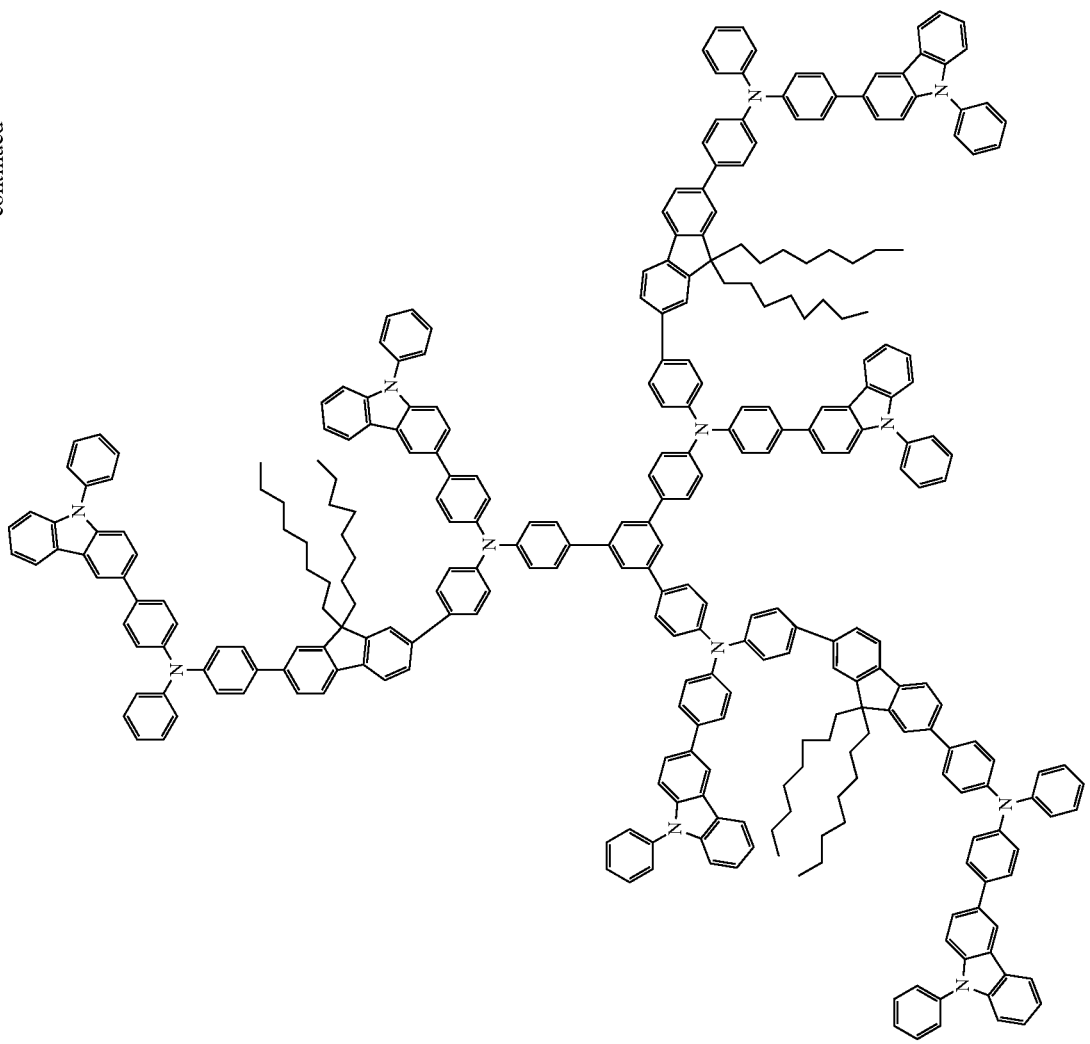

-continued
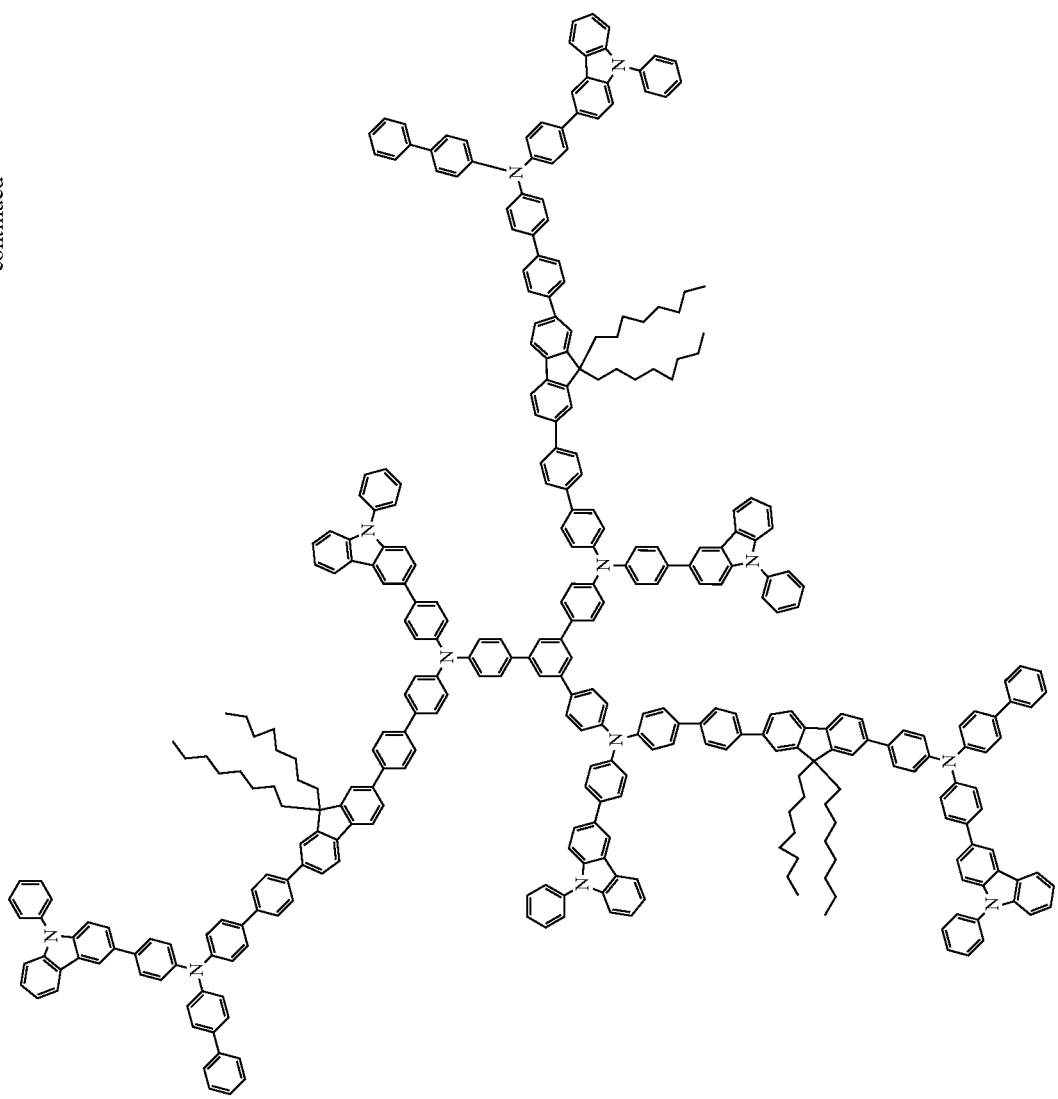

-continued
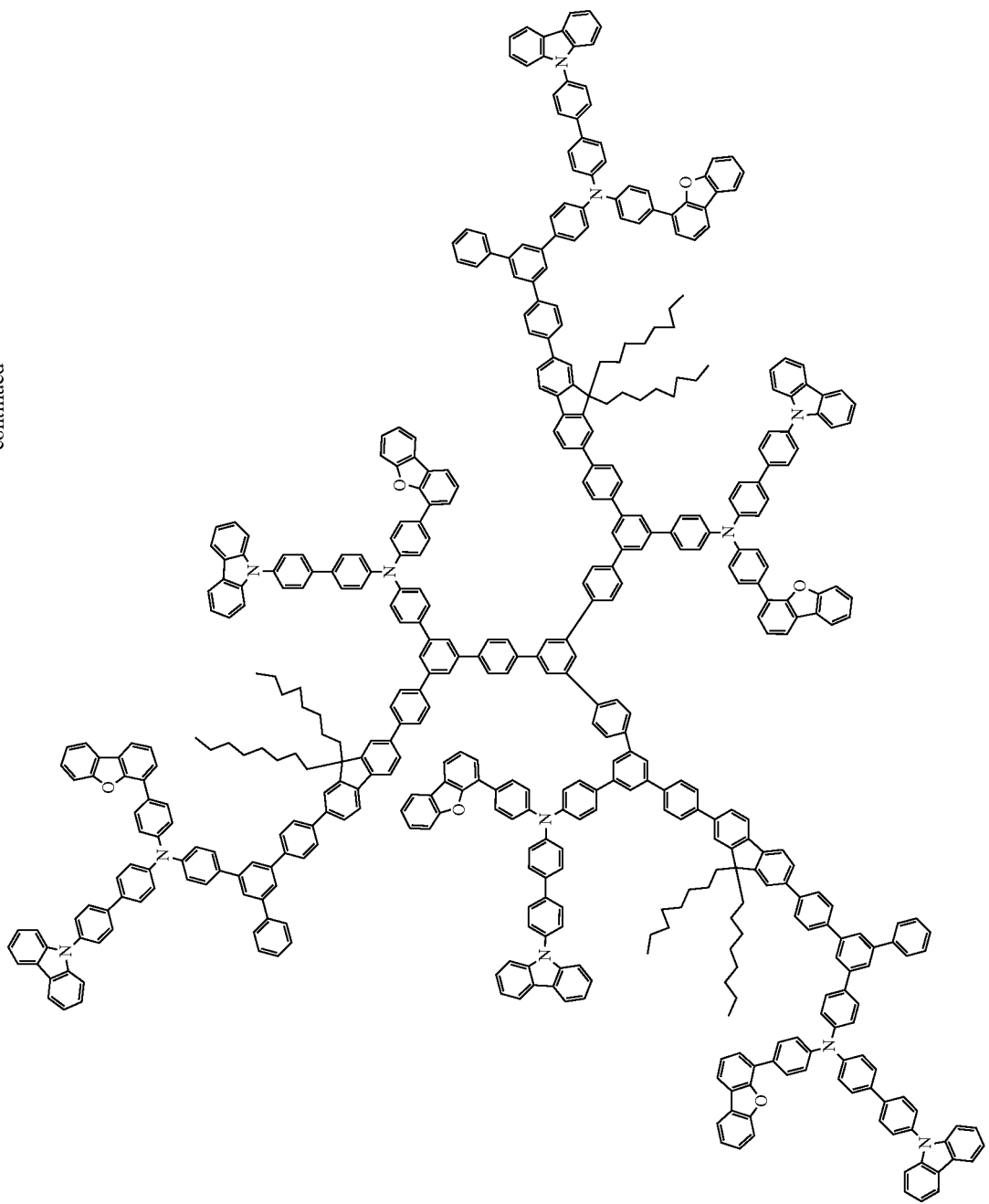

-continued
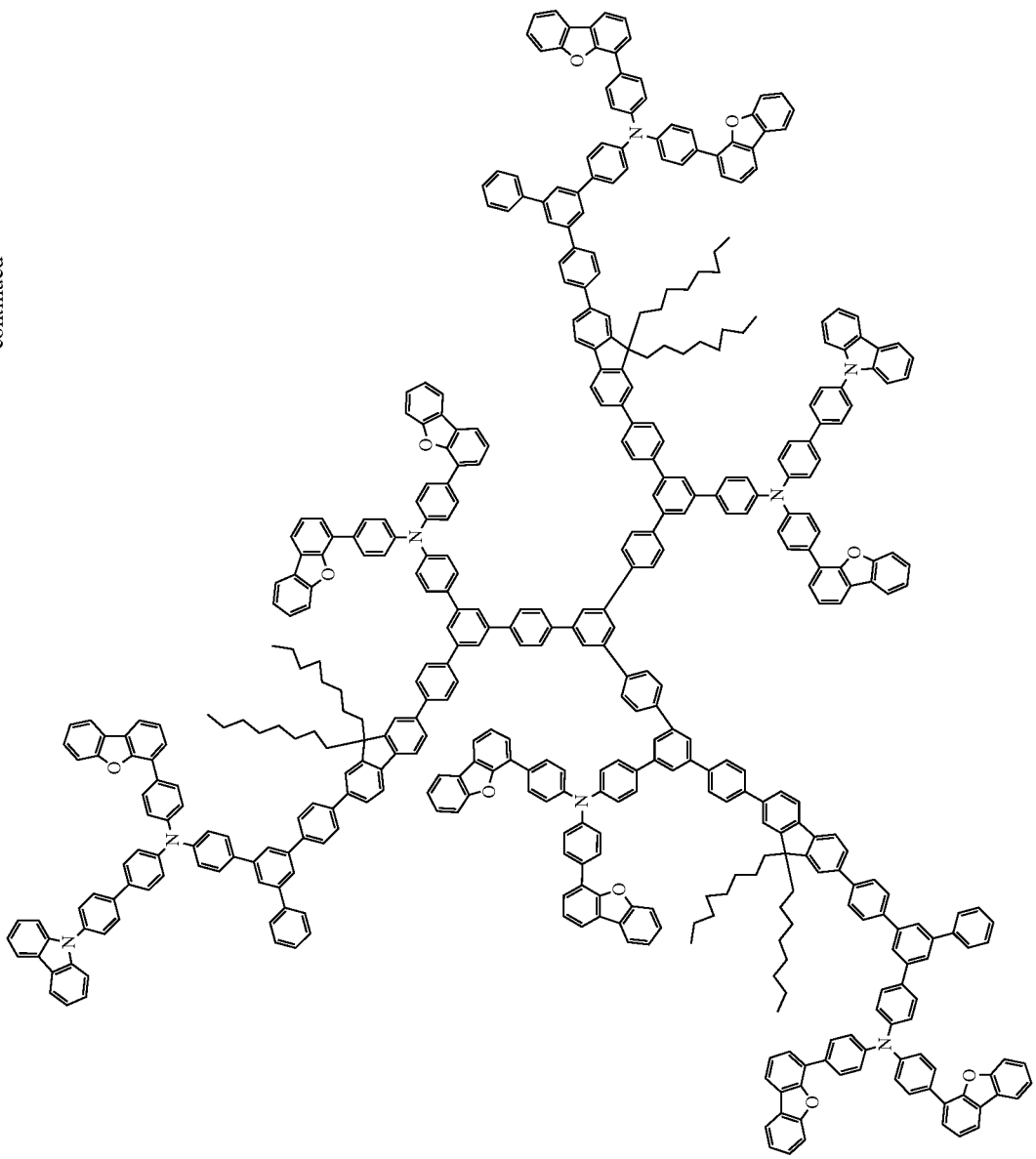

-continued
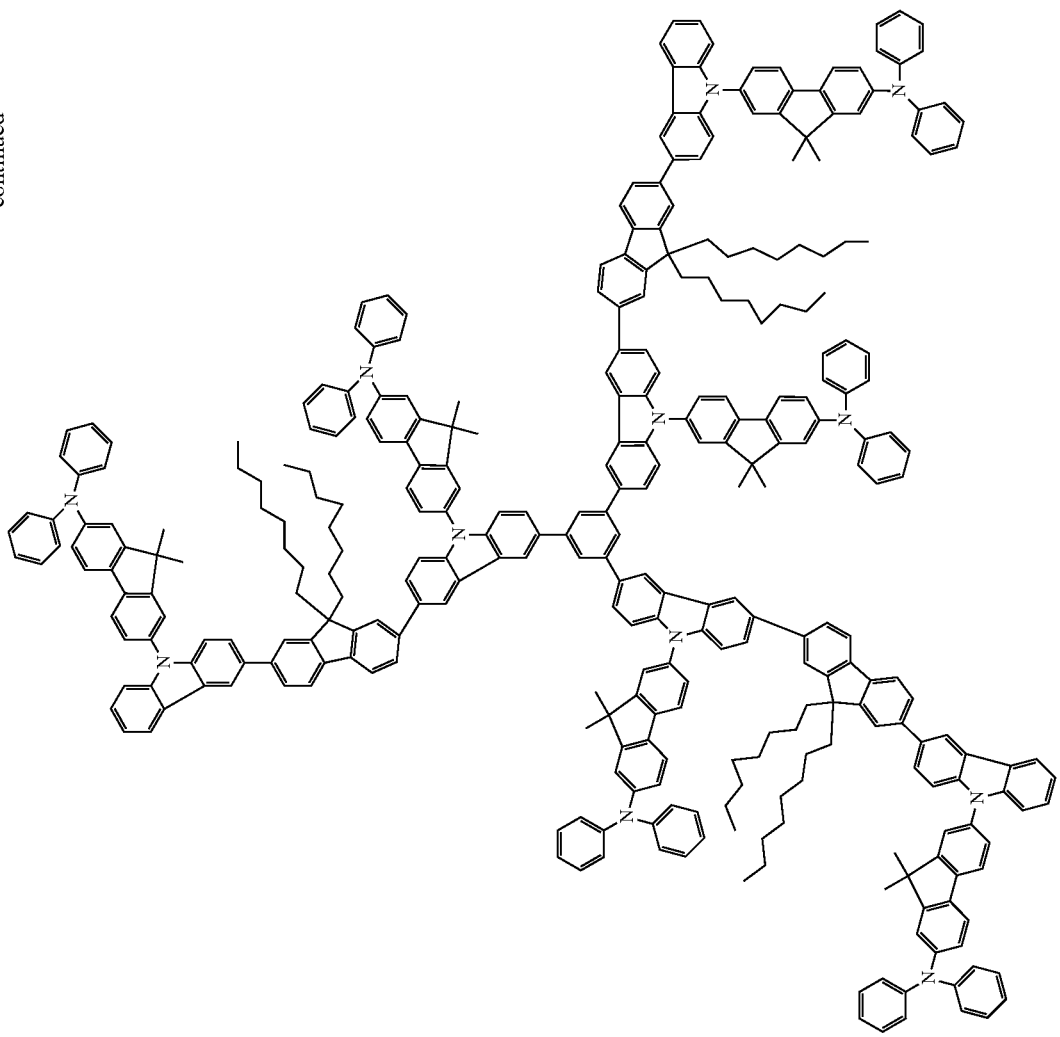

-continued
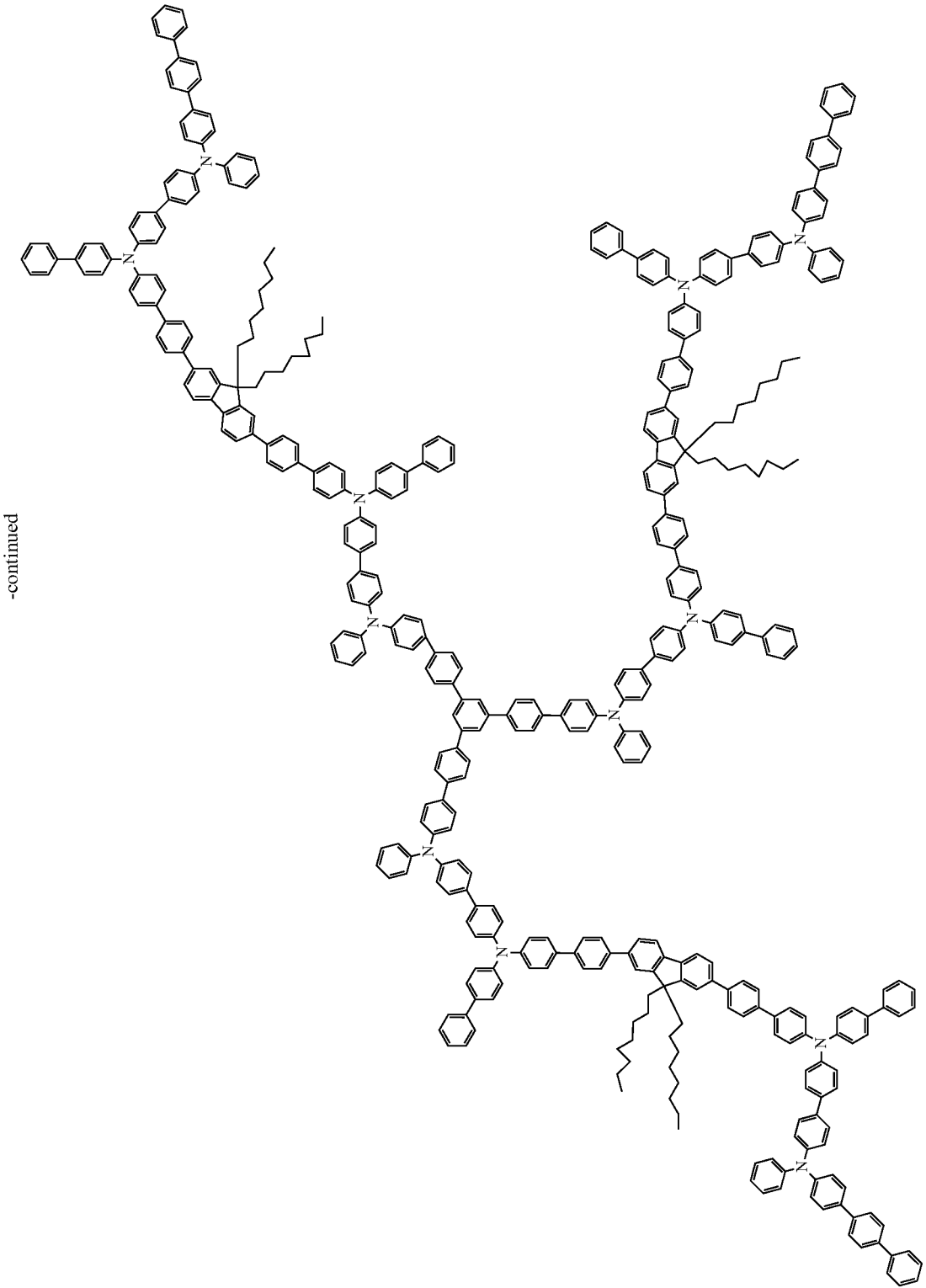

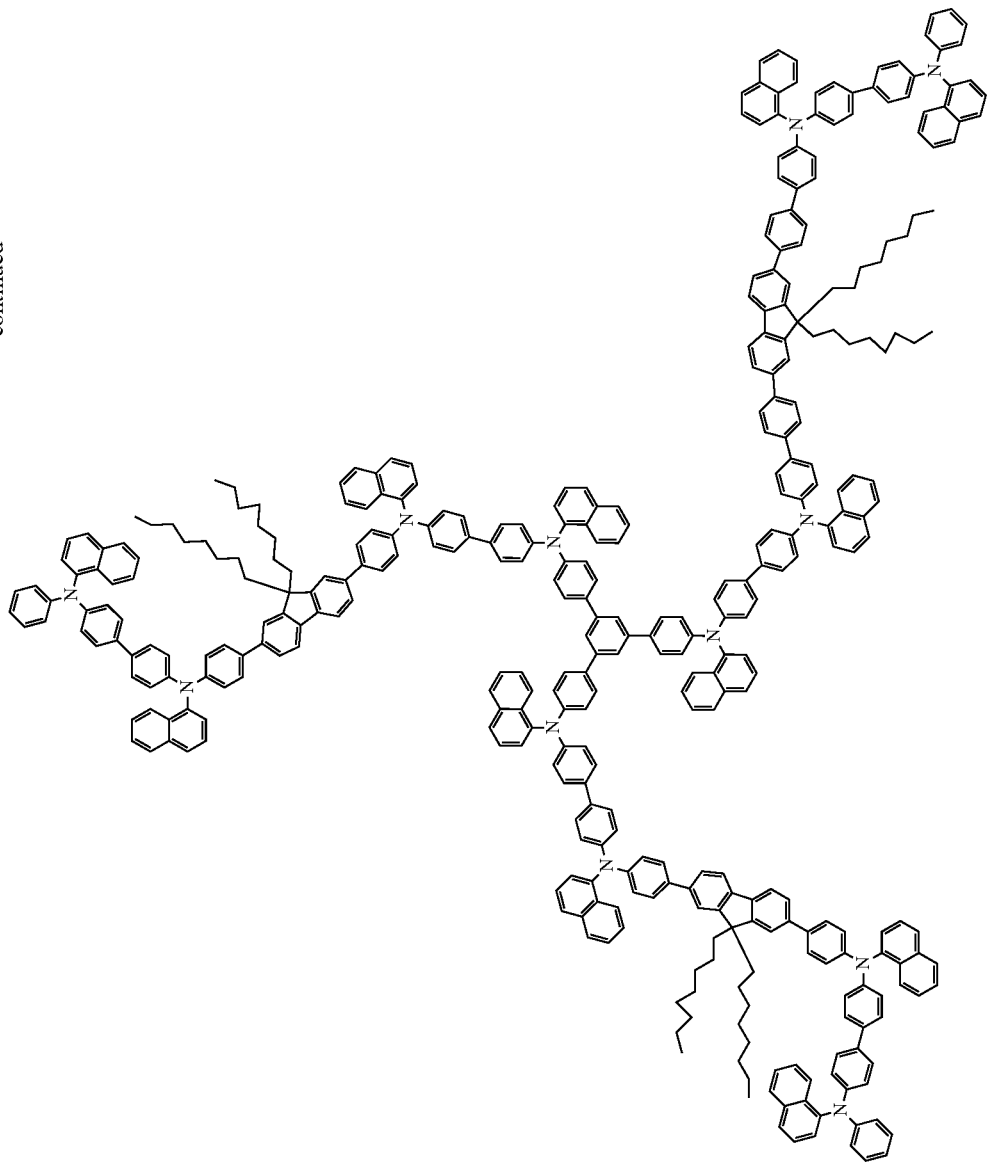

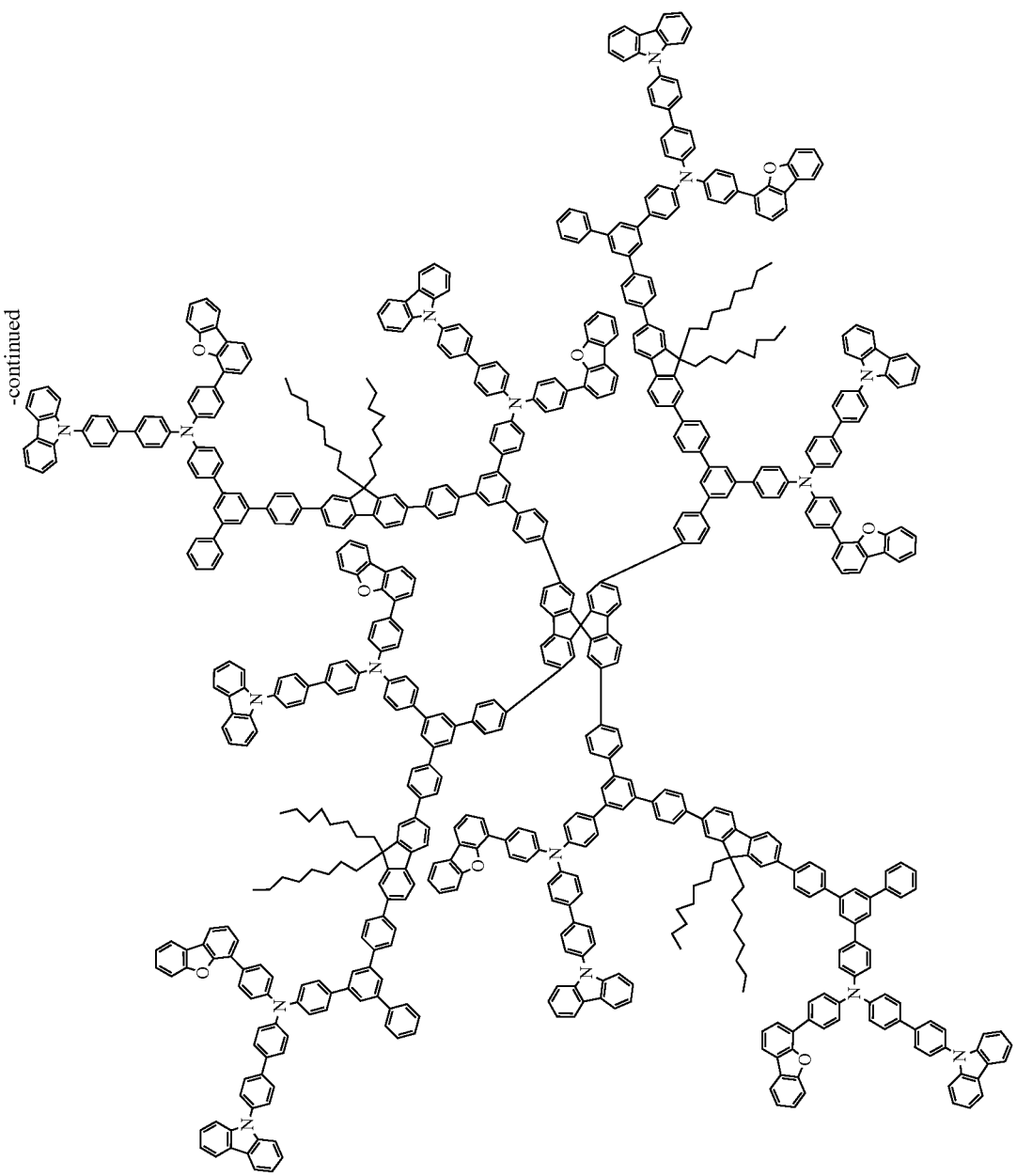

-continued
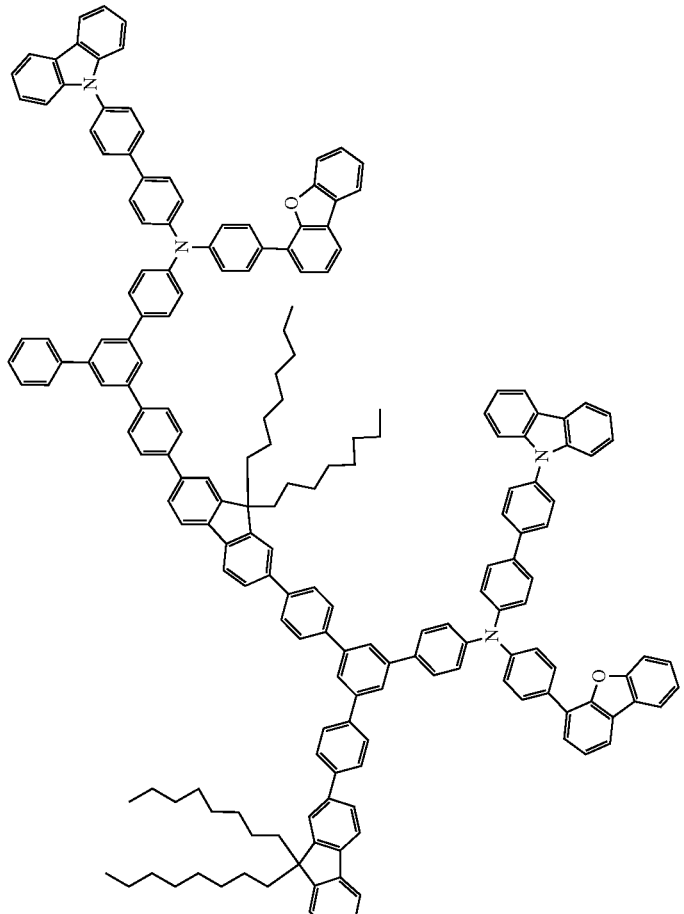
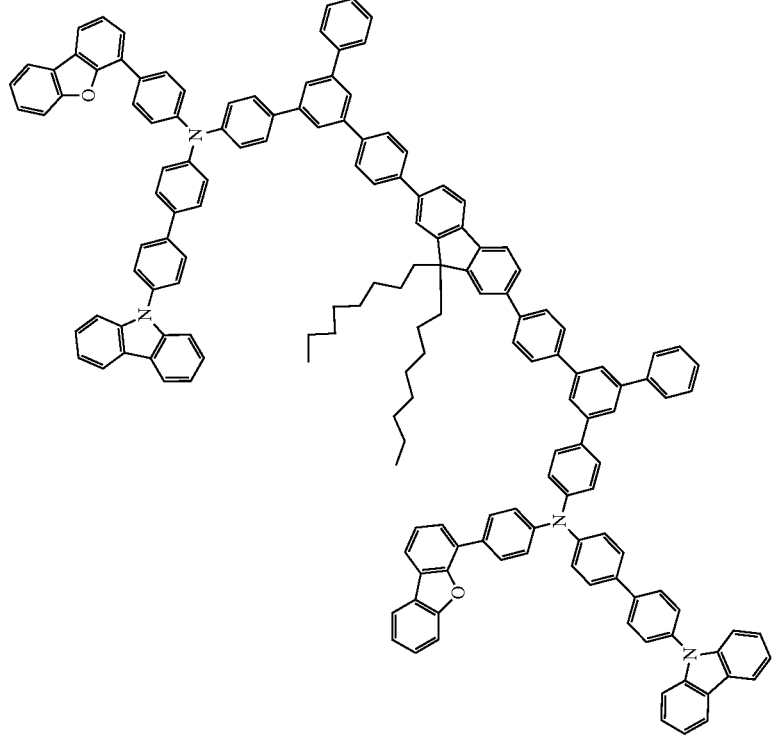

-continued
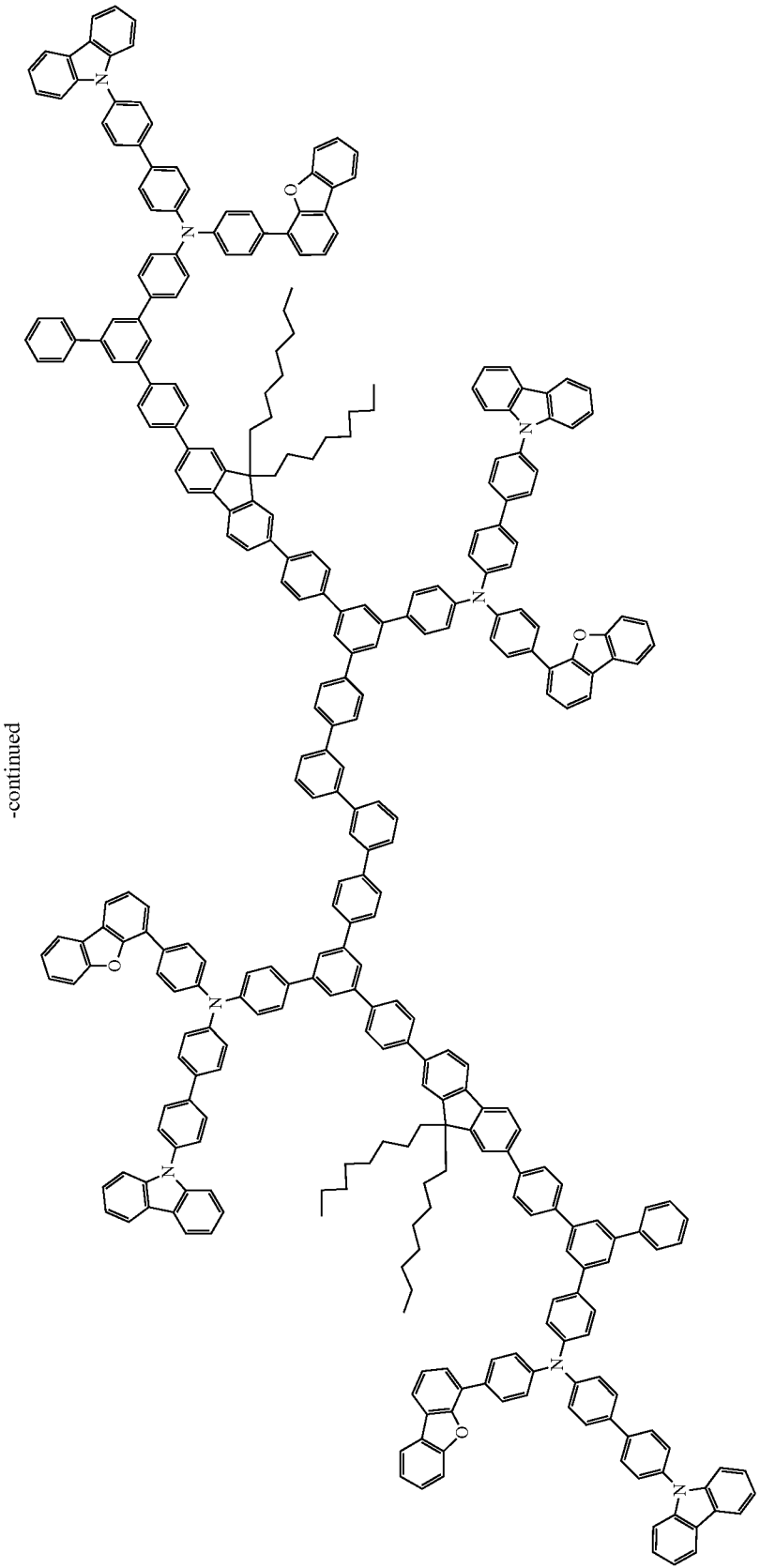

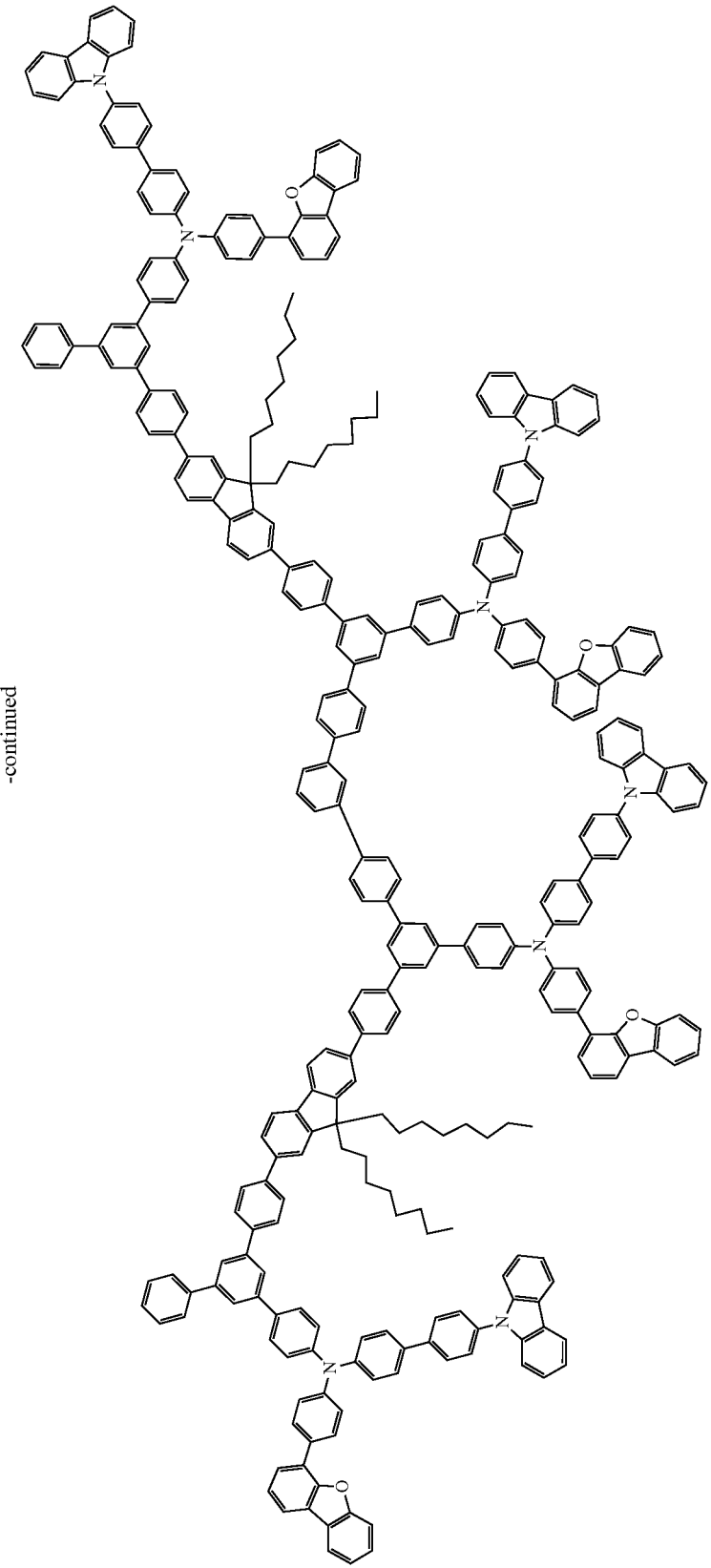

-continued
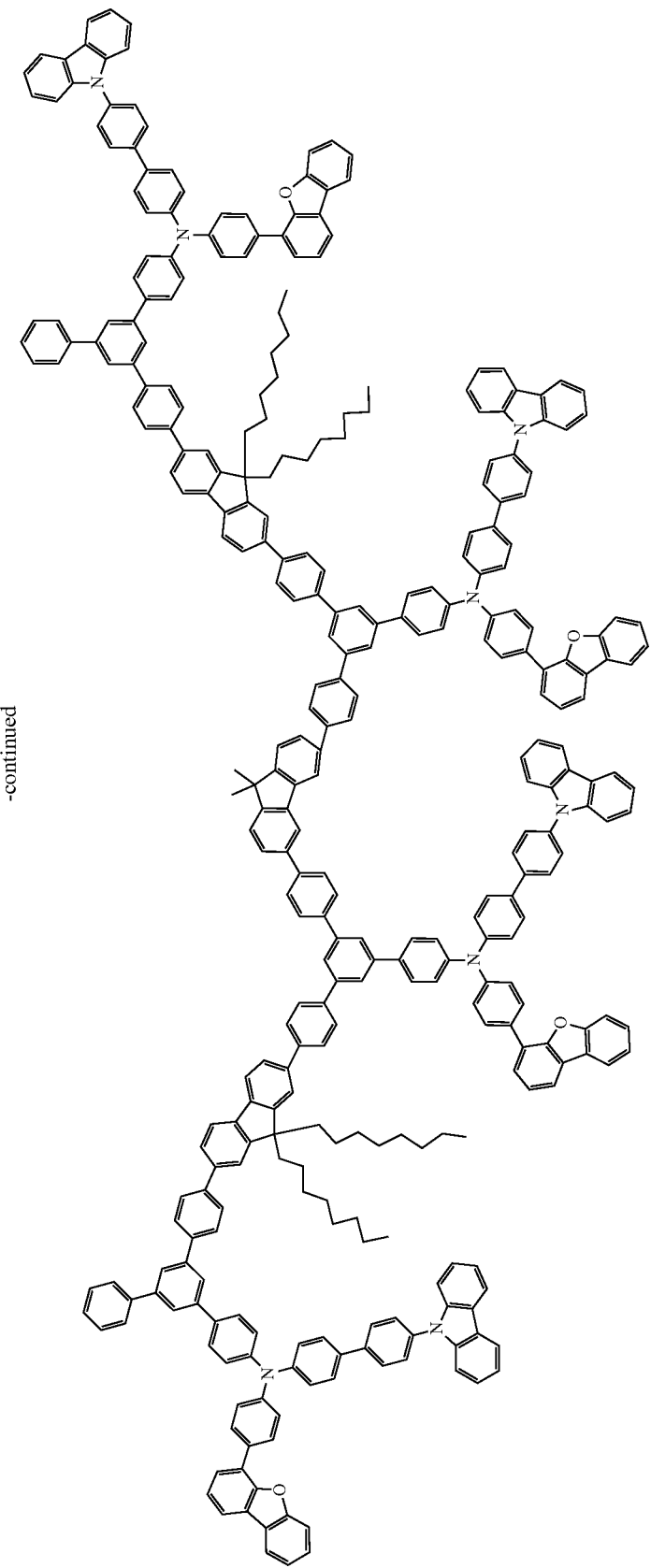

-continued
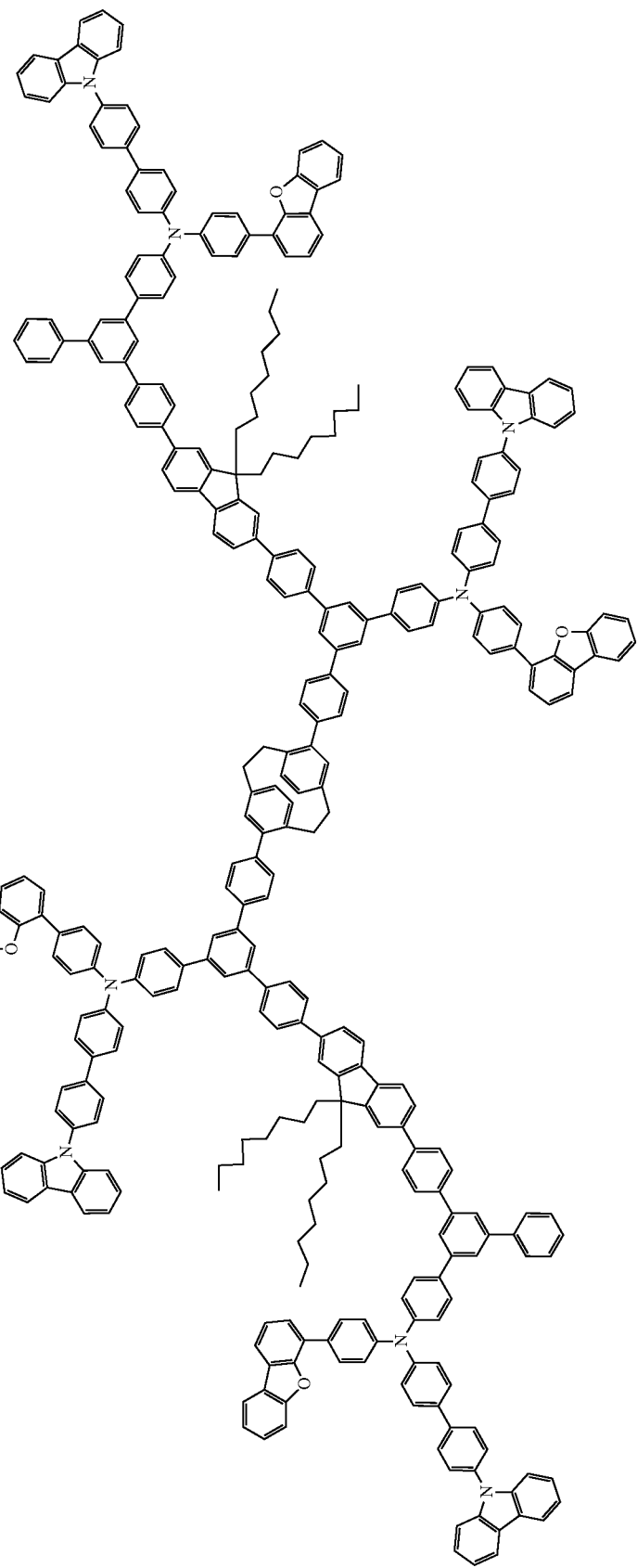

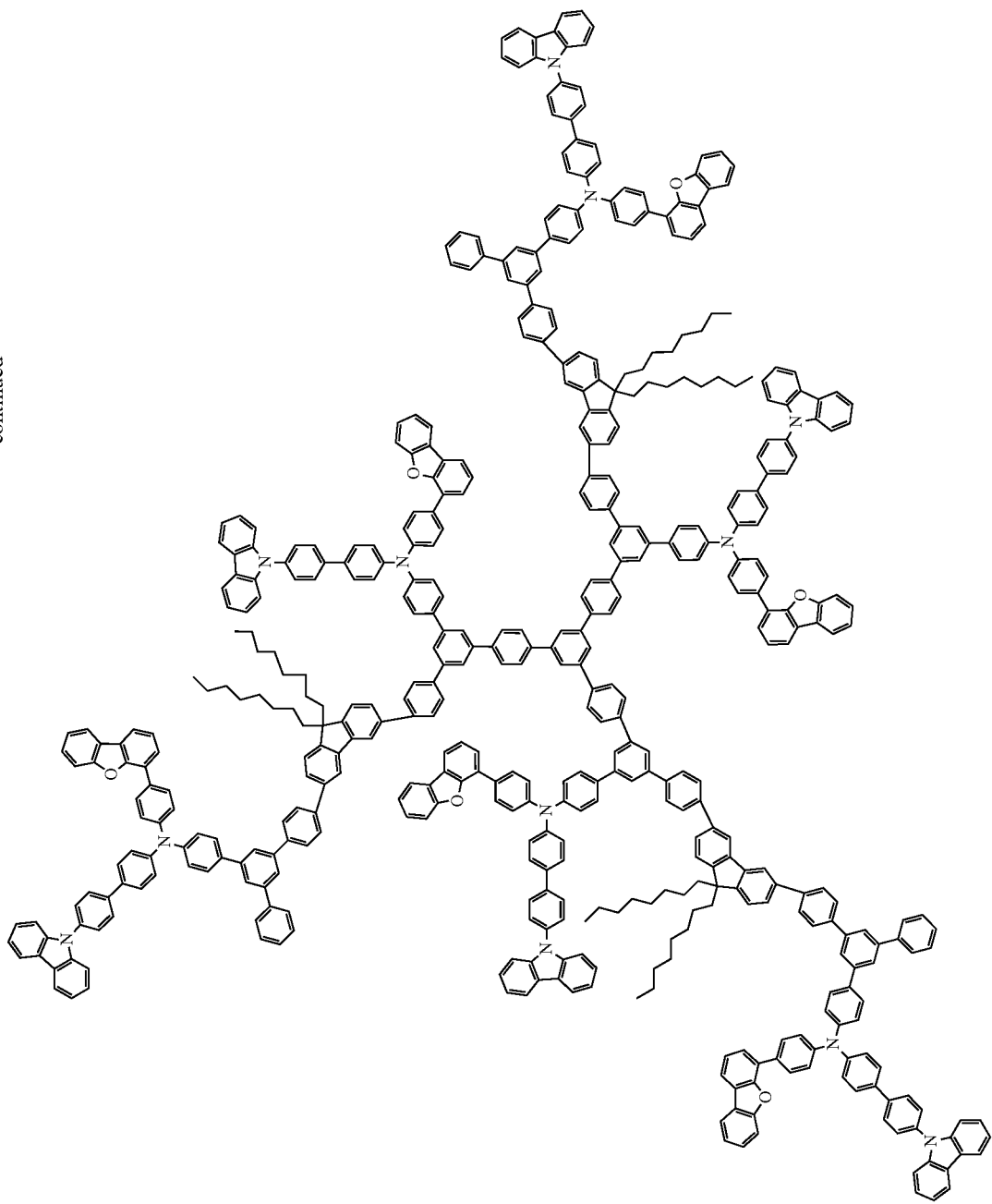

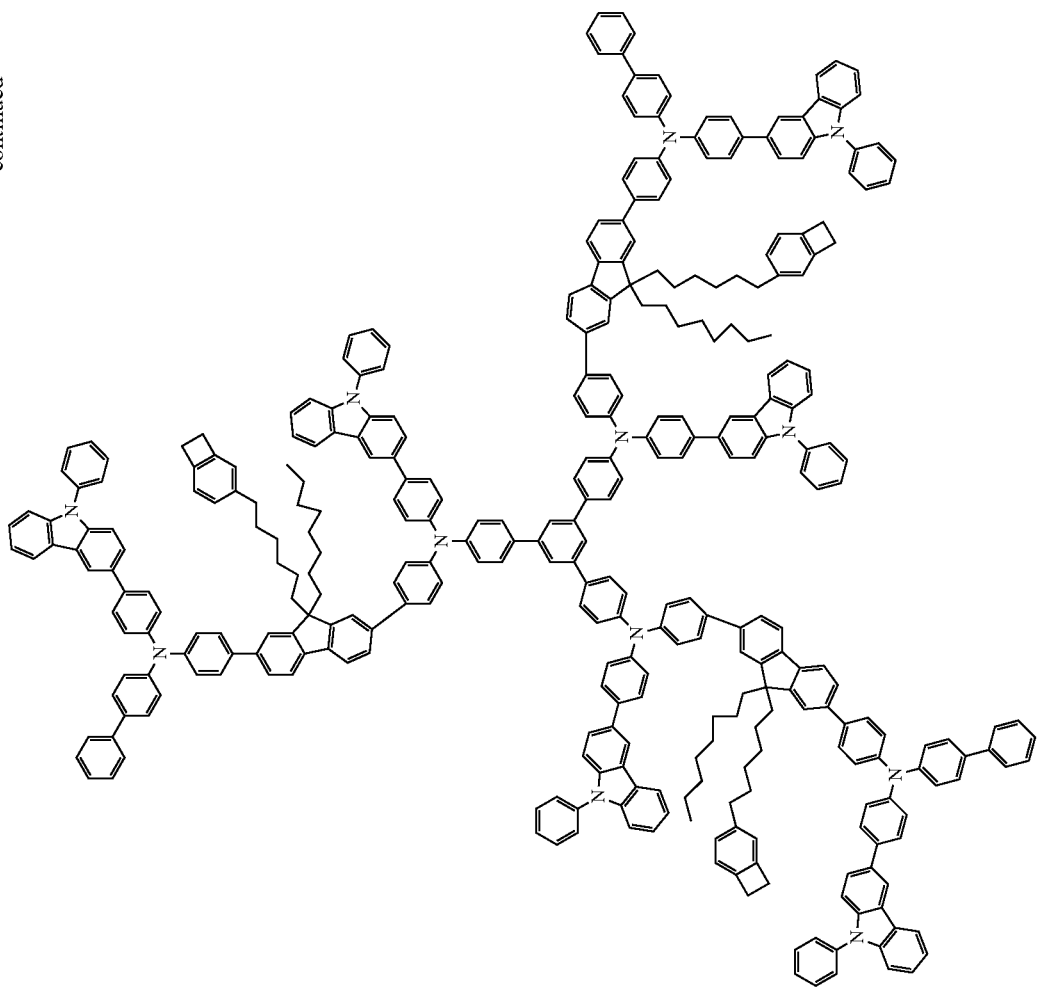

-continued
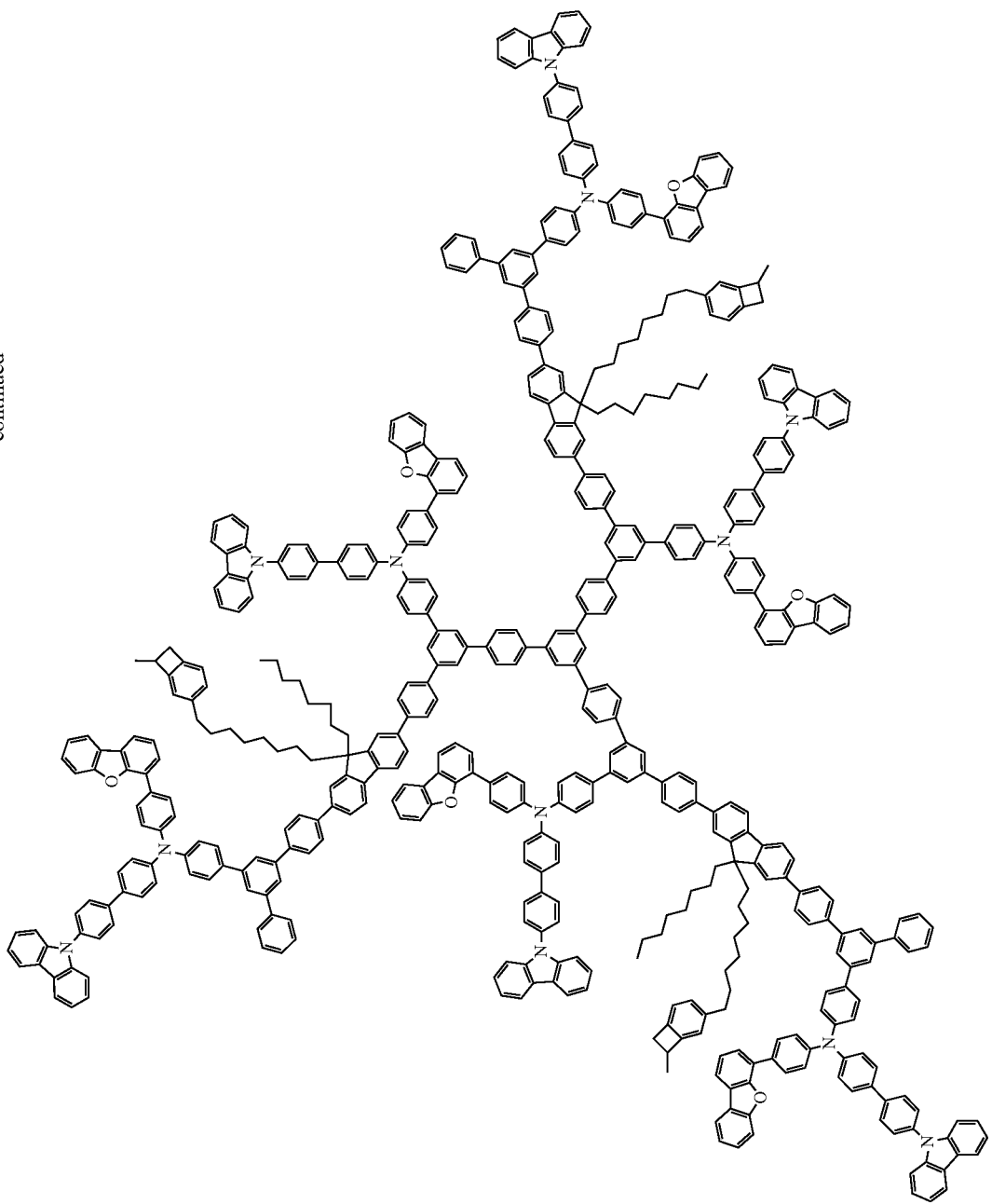

-continued
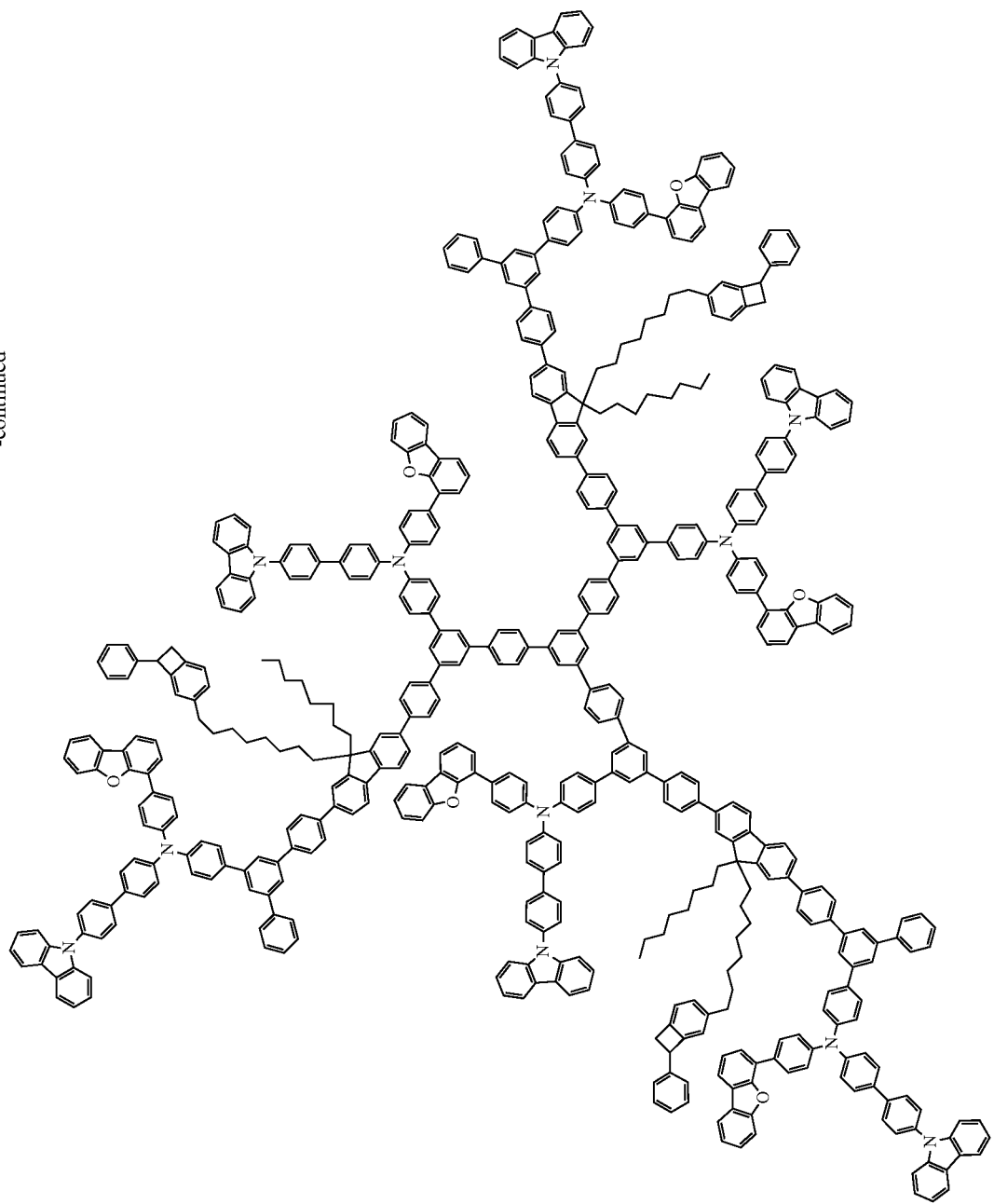

-continued
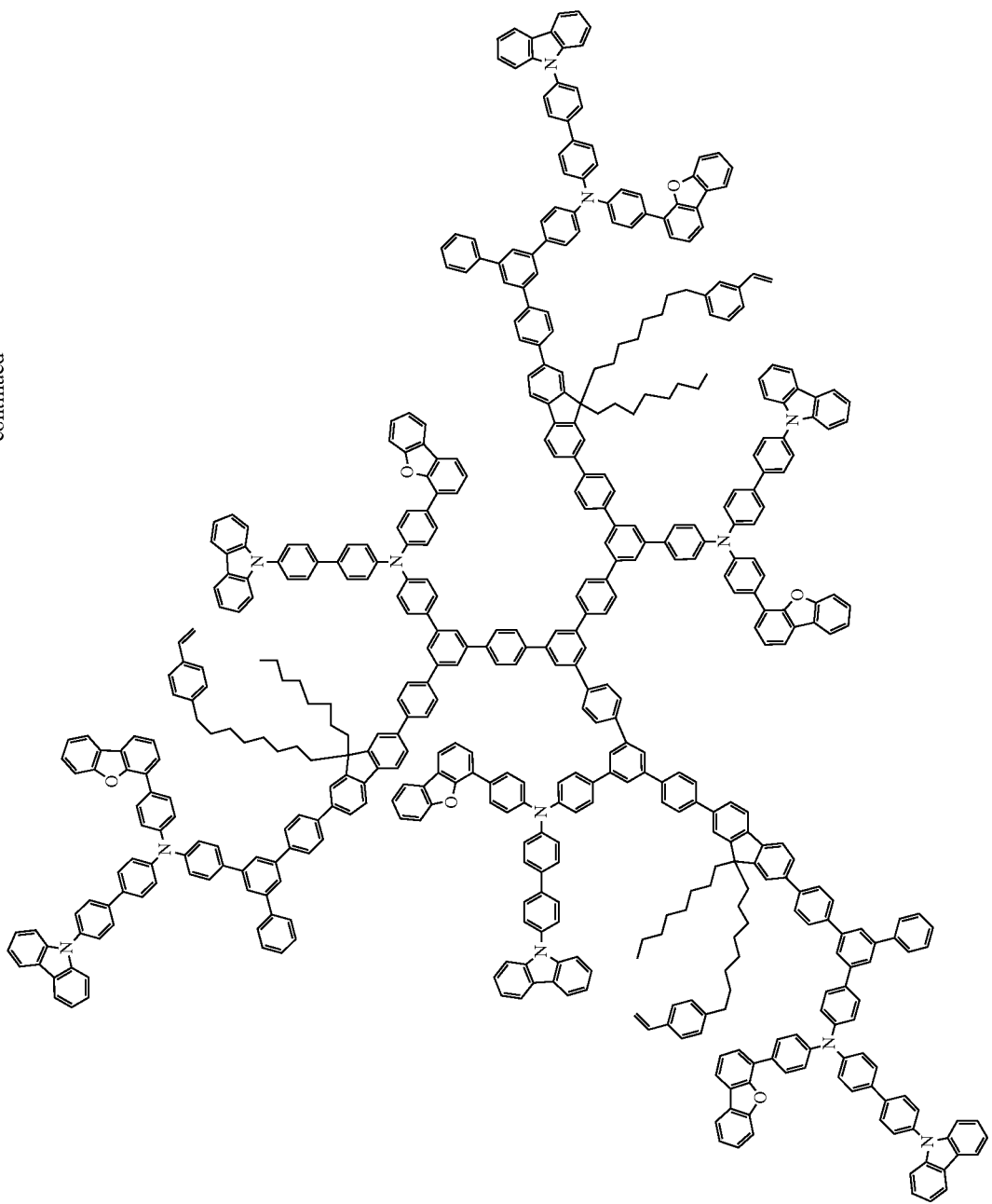

-continued
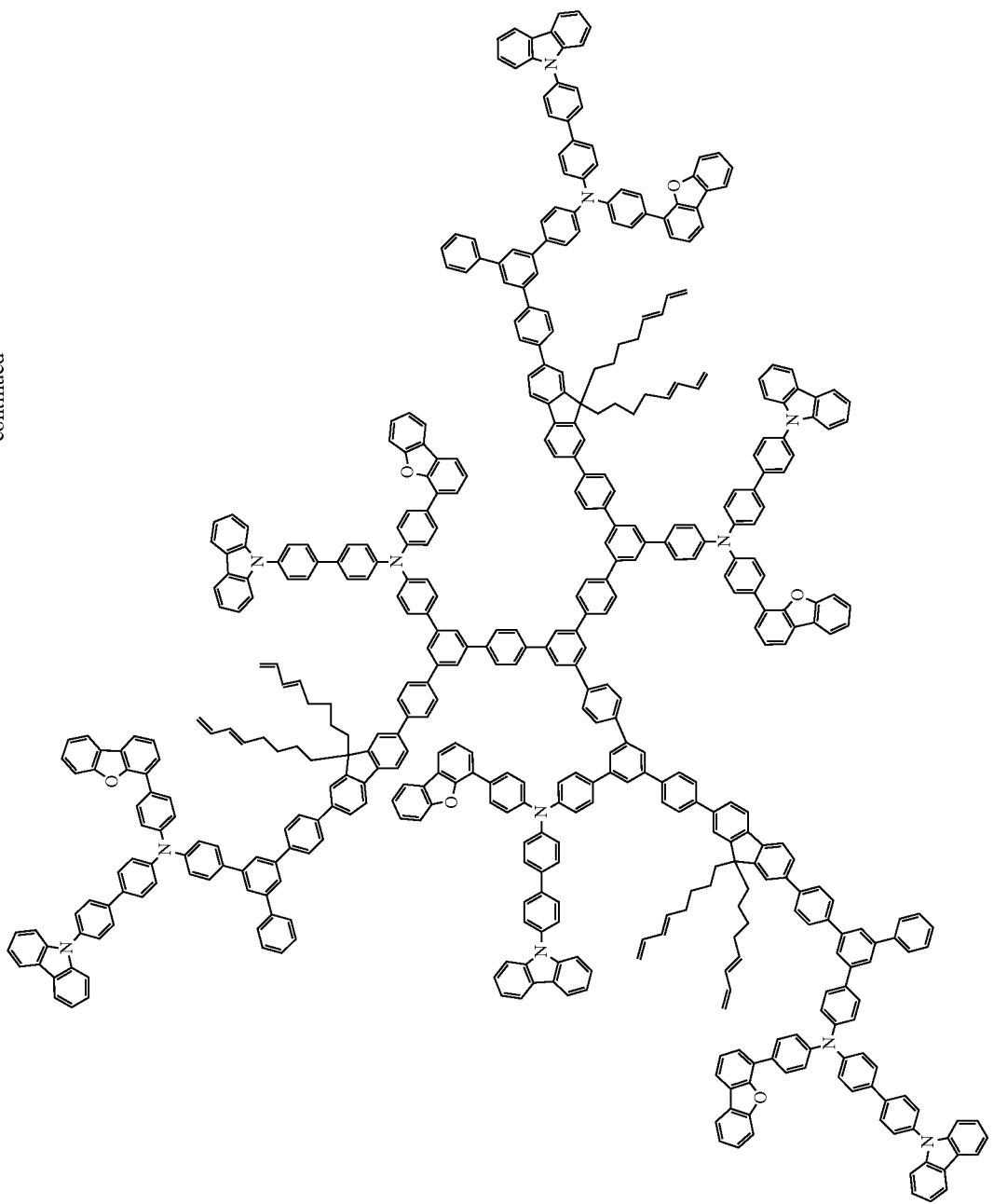

-continued
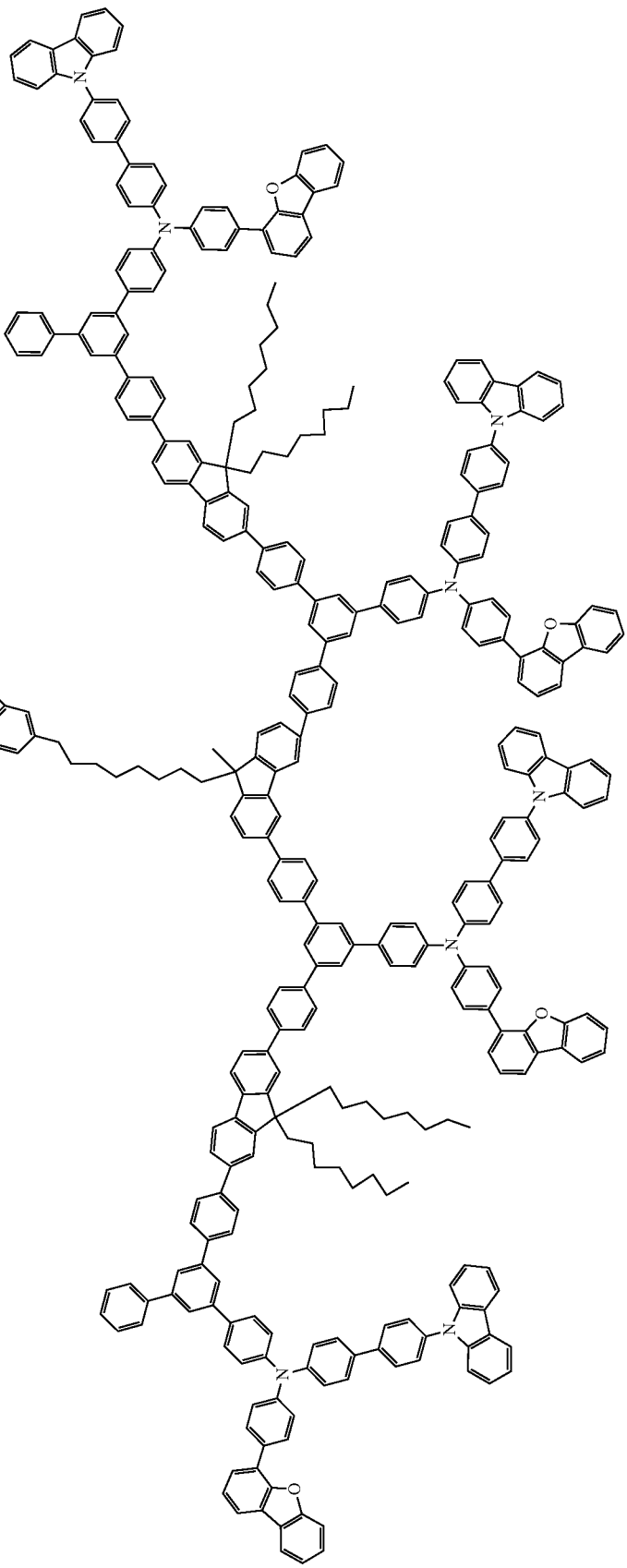

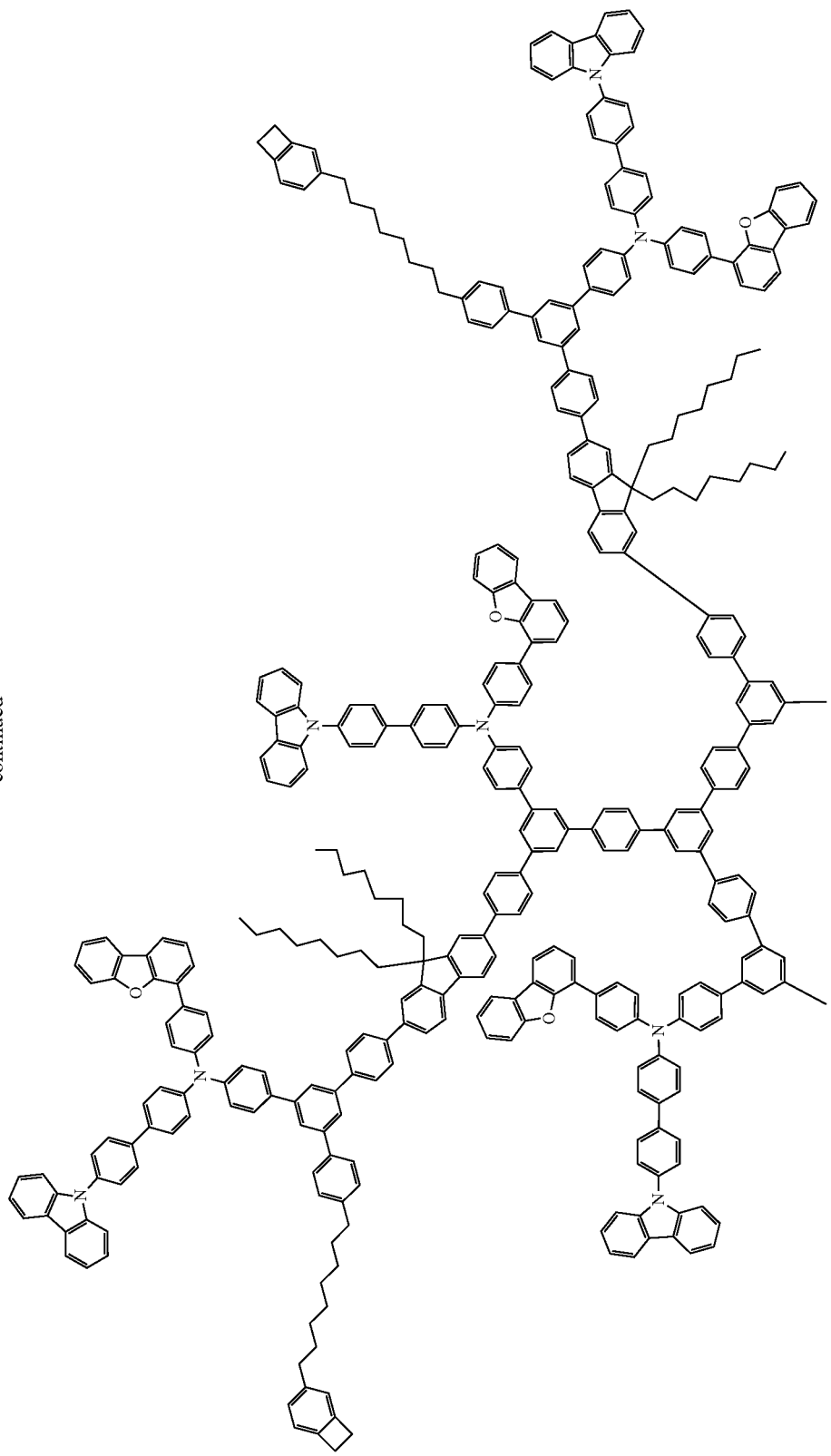

-continued
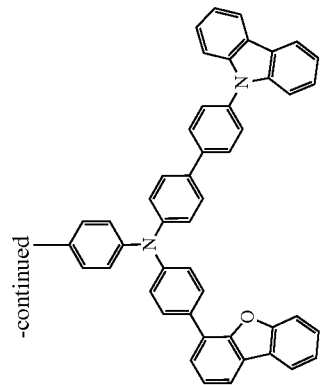
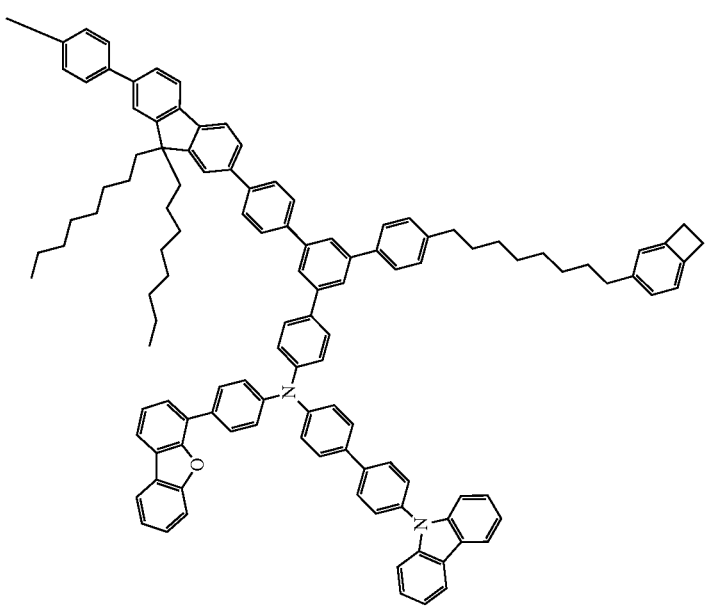

The aromatic amine derivative of the invention is used preferably as a material for an organic device, a hole-injecting/transporting material and a material for an organic electroluminescence device. The resulting organic device, in particular organic EL device has excellent device properties such as a prolonged life and a high luminous efficiency. In addition, even if the resulting device is driven at high temperatures, which is practical in applications of a display or an illumination, the device suffers only a small degree of deterioration, whereby a practicable organic EL device can be provided.

In addition, since a hole-injecting/transporting layer can be formed uniformly by a coating method, the derivative of the invention can be suitably used for reduction in cost or sizing up of a display or an illumination.

Examples of the above-mentioned organic device include, in addition to an organic EL device, an organic TFT, a photoelectric conversion element such as an organic solar cell and an image sensor.

The organic EL device of the invention can be suitably used as a planar emitting body such as a flat panel display of a wall-hanging television, general or special-purpose lighting, backlight of a copier, a printer or a liquid crystal display, light sources for instruments, a display panel, navigation light, or the like.

Further, the aromatic amine derivative of the invention can be also used as a material for an electrophotographic photoreceptor.

As for the polymerizable monomer as an aromatic amine derivative having a group comprising a polymerizable functional group, the polymer having one or more repeating units derived from the polymerizable monomer (often referred to as the polymer of the invention hereinafter) can be also used preferably as a material for an organic device, a hole-injecting/transporting material, a material for an organic electroluminescence device as described above. The resulting organic device, in particular organic EL device, has excellent device properties such as a prolonged life and a high luminous efficiency. In addition, even if the resulting device is driven at high temperatures, which is practicable in applications of a display or an illumination, it suffers only a small degree of deterioration, whereby a practicable organic EL device can be provided.

In addition, since a hole-injecting/transporting layer can be formed uniformly by a coating method, the derivative of the invention can be suitably used for reduction in cost or sizing up of a display or an illumination.

The polymer of the invention is any of the following polymers (a) to (c):
(a) a homopolymer having a repeating unit derived from one selected from the group consisting of the polymerizable monomers of the invention,
(b) a copolymer having a repeating unit derived from two or more monomers selected from the group consisting of the polymerizable monomers of the invention,
(c) a copolymer having a repeating unit derived from one or more selected from the group consisting of the polymerizable monomers of the invention and a repeating unit derived from other monomers than the monomer of the invention.

When the polymer of the invention is the copolymer (c), it contains a unit derived from the polymerizable monomer of the invention preferably in an amount of 50 mol % or more, more preferably in an amount of 70 mol % or more. If the polymerizable monomer of the invention is contained in an amount of less than 50 mol %, the above-mentioned advantageous effects obtained by using the polymerizable monomer of the invention may not be exhibited sufficiently.

The molecular weight of the polymer of the invention is not especially limited; varying from a molecular weight of an oligomer which is a dimer or more to an ultrahigh molecular weight.

The polymer has preferably a number average molecular weight (Mn) of $10^3$ to $10^8$, with $5\times10^3$ to $10^6$ being more preferable. It has a weight-average molecular weight of $10^3$ to $10^8$ preferably, more preferably $5\times10^3$ to $10^6$. The molecular weight distribution represented by Mw/Mn is not especially limited, but preferably 10 or less, further preferably 3 or less.

If the molecular weight of the polymer is too large, in the device production, uniform film formation cannot be achieved due to gelation. On the other hand, if the molecular weight of the polymer is too small, the control of solubility may become difficult.

Meanwhile, the number average molecular weight and the weight-average molecular weight can be determined by means of the Size Exclusion Chromatography (SEC) by weighing out using styrene as a polymer standard.

The polymer of the invention can be obtained by polymerizing the polymerizable monomer of the invention.

Although the method for polymerizing is not particularly restricted, examples thereof include radical polymerization, ionic polymerization, living polymerization, radical living polymerization and coordination polymerization. Radical polymerization or cationic polymerization is preferable.

As the initiator in radical polymerization, an azo compound or a peroxide can be given, for example. Azobisisobutyronitrile (AIBN), an azobisisobutyric acid diester derivative and benzoyl peroxide (BPO) are preferable.

As the initiator in cationic polymerization, various strong acids (p-toluenesulfonic acid, trifluoromethanesulfonic acid and the like) and Lewis acids are preferable.

The polymerization can also be conducted by light irradiation and/or heat treatment.

The organic EL device of the invention comprises one or more organic thin film layers including at least an emitting layer between a cathode and an anode, the least one of the organic thin film layers comprising the aromatic derivative of the invention and/or the polymer of the invention.

In the organic EL device of the invention, it is preferred that the organic thin film layers have at least one of a hole-transporting layer and a hole-injecting layer, and the aromatic amine derivative of the invention and/or the polymer of the invention be contained in at least one of the hole-transporting layer and the hole-injecting layer.

Further, it is more preferred that the aromatic amine derivative of the invention or the polymer of the invention be contained in the at least one of a hole-transporting layer and a hole-injecting layer as a main component. Specifically, in the hole-transporting layer or the hole-injecting layer, the aromatic amine derivative of the invention or the polymer of the invention is contained preferably at the amount of 51 to 100 wt %.

When the device comprises at least one of a hole-transporting layer and a hole-injecting layer, an acceptor material is preferably contained in at least one of the hole-injecting layer and the hole-transporting layer. The acceptor material is preferably contained in the layer adjacent to the anode.

The contained acceptor material increases the hole density or the hole mobility in the hole-injecting/transporting layer, whereby the resulting organic EL device can be driven at a lower voltage, and the resulting improved carrier balance enables the life of the device to be prolonged. In particular, the acceptor material is preferably contained in the layer adjacent to the anode.

The acceptor material is preferably an organic compound having an electron-attracting substituent or an electron deficient ring.

As the electron-attracting substituent, a halogen atom, CN—, a carbonyl group, an arylboron group and the like can be given, for example.

As the electron deficient ring, a compound and the like selected from the group consisting of 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, phthalazine, quinazoline, quinoxaline, 3-(1,2,4-N)-triazolyl, 5-(1,2,4-N)-triazolyl, 5-tetrazolyl, 4-(1-O,3-N)-oxazole, 5-(1-O,3-N)-oxazole, 4-(1-S,3-N)-thiazole, 5-(1-S,3-N)-thiazole, 2-benzoxazole, 2-benzothiazole, 4-(1,2,3-N)-benzotriazole and benzimidazole can be given, but not limited thereto.

As a representative device configuration of an organic EL device of the invention, the following configurations can be given.
(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron blocking layer/emitting layer/cathode
(7) Anode/organic semiconductor layer/emitting layer/adhesion improving layer/cathode
(8) Anode/hole-injecting layer/hole-transporting layer/emitting layer/electron injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron injecting layer/cathode Of these, the configuration (8) is normally used. However, the device configuration is not limited to these.

Each layer of the organic EL device of the invention may be composed of known materials. For example, the emitting layer contains a styryl amine compound, an aryl amine compound or a fluoranthene-based compound, preferably.

The organic EL device of the invention emits blue light, preferably. The reason therefor is that the aromatic amine derivative of the invention has a wide band gap suitable for blue emission which can block electrons to recombine holes and electrons in an emitting layer efficiently, and the ionization potential thereof can be adjusted easily so as to be suitable for injecting of holes into the blue emitting layer.

In addition, since the aromatic amine derivative has such a wide band gap, it can be applied not only to a fluorescent organic EL device but also to a phosphorescent organic EL device.

Each layer of the organic EL device of the invention can be formed by known methods including dry-type film forming methods such as vacuum vapor deposition, sputtering and plasma ion plating, and wet-type film forming methods such as spin coating, dipping and flow coating. Although the film thickness is not particularly restricted, it is required to be a proper value. If the film thickness is too large, a large applied voltage is required for a predetermined light output, thereby causing lower efficiency. If the film thickness is too small, pin holes and the like are generated, whereby sufficient luminance can hardly be obtained when electric field is impressed. The film thickness is normally in the range from 5 nm to 10 μm, further preferably in the range from 10 nm to 0.2 μm.

The layer containing the aromatic amine derivative and/or polymer of the invention (in particular, hole-injecting/transporting layer) can be formed by a spin coating method, a casting method, a micro gravure coating method, a gravure coating method, a bar coating method, a roll coating method, a slit coating method, a wire bar coating method, a dip coating method, a spray coating method, a screen printing method, a flexographic printing method, an offset printing method, an inkjet printing method, a nozzle printing method and the like. In the case of patterning, a screen printing method, a flexographic printing method, an offset printing method and an inkjet printing method are preferable. Film formation by these methods can be carried out under the conditions well known to the skilled in the art and need not be detailed.

After the film formation, it suffices to conduct drying in vacuum and with heating to remove the solvent. The resulting film can become completely insoluble through polymerization reaction by exposing to light and heating at high temperatures (250° C.).

It suffices to allow at least one of the aromatic amine derivatives of the invention to be contained in the solution for film formation. In addition to the above-mentioned materials, other hole-transporting materials, electron-transporting materials, emitting materials, acceptor materials, solvents, additives such as a stabilizer can be contained. The content of the aromatic amine derivative in the above-mentioned solution for film formation is preferably in the range of 20 to 100 wt % relative to the total amount of the composition excluding the solvent, more preferably 51 to 100 wt %. It is more preferred that the aromatic amine derivative be a main component of the composition excluding the solvent. The ratio of the solvent is preferably 1 to 99.9 wt % of the solution for film formation, with 80 to 99 wt % being more preferably.

The solution for film formation may contain additives for adjusting the viscosity and/or the surface tension, for example, thickeners (high-molecular-weight compound, poor solvent of the aromatic amine derivative of the invention or the like), viscosity depressants (low-molecular-weight compound or the like) and surfactants. Further, in order to improve the storage stability, antioxidants which have no impact on the performance of the resulting organic EL device, for example, phenolic antioxidants, phosphorous antioxidants or the like, can be contained.

Examples of the available high-molecular-weight compound include an insulating resin such as polystyrene, polycarbonate, polyarylate, polyester, polyamide, polyurethane, polysulfone, polymethyl methacrylate, polymethyl acrylate or cellulose, and a copolymer thereof, a photoconductive resin such as poly-N-vinyl carbazole or polysilane and a conductive resin such as polythiophene or polypyrrole.

Examples of the solvent of the solution for film formation include a chlorinated solvent such as chloroform, methylene chloride, 1,2-dichloroethane, 1,1,2-trichloroethane, chlorobenzene or o-dichlorobenene; an ether type solvent such as tetrahydrofuran, dioxane, dioxolan or anisole; an aromatic hydrocarbon type solvent such as toluene or xylene; an aliphatic hydrocarbon type solvent such as cyclohexane, methylcyclohexane, n-pentane, n-hexane, n-heptane, n-octane, n-nonane or n-decane, a ketone type solvent such as acetone, methyl ethyl ketone, cyclohexanone, benzophenone or acetophenone; an ester type solvent such as ethyl acetate, butyl acetate, ethyl cellosolve acetate, methyl benzoate or phenyl acetate; a polyol such as ethylene glycol, ethylene glycol monobutyl ether, ethylene glycol monoethyl ether, ethylene glycol monomethyl ether, dimethoxyethane, propylene glycol, diethoxyethane, triethylene glycol monoethyl ether, glycerin, 1,2-hexanediol or the like, and derivatives thereof; an alcohols solvent such as methanol, ethanol, propanol, isopropanol, cyclohexanol or the like; a sulfoxide type solvent such as dimethylsulfoxide or the like; and an amide type solvent such as N-methyl-2-pyrrolidone, N,N-dimethylformamide or the like. These organic solvents can be used singly or by combination thereof. Of these, in respect of the solubility, the uniform film formation, the viscosity characteristics or the like, aromatic hydrocarbon type solvents, ether type solvents, aliphatic hydrocarbon type solvents, ester type solvents and ketone type solvents are preferable. More preferable are toluene, xylene, ethyl benzene, diethyl benzene, trimethyl benzene, n-propyl benzene, isopropyl benzene, n-butyl benzene, isobutyl benzene, 5-butyl benzene, n-hexyl benzene, cyclohexyl benzene, 1-methylnaphthalene, tetralin, 1,3-dioxane, 1,4-dioxane, 1,3-dioxolan, anisole, ethoxybenzene, cyclohexane, bicyclohexyl, cyclohexenyl cyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-dacanone, dicyclohexyl ketone, acetophenone and benzophenone.

By the above-mentioned exemplified materials and methods for forming layers, an anode, an emitting layer, if needed, a hole-injecting/transporting layer and, if needed, an electron-injecting/transporting layer are formed and further a cathode is formed, whereby an organic EL device can be fabricated. From a cathode to an anode, an organic EL device can be fabricated in the reverse order of the above-mentioned order.

EXAMPLES

The invention will be explained in more detail with reference to Examples below. However the invention is not limited to the following Examples.

Example 1

A compound H-1 was synthesized by the following synthesis scheme.

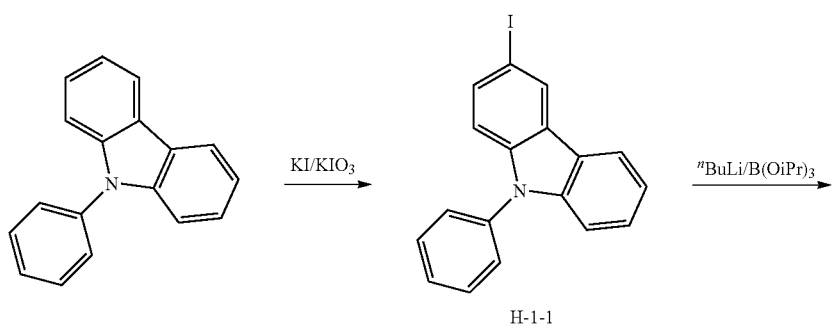

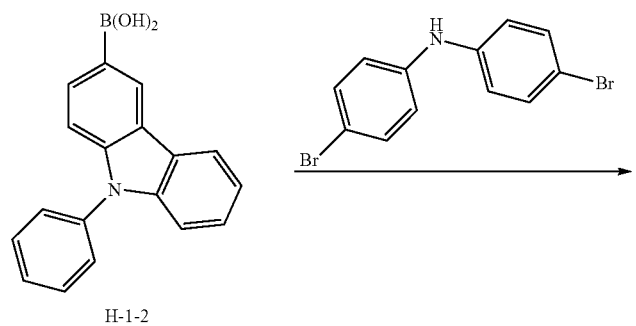

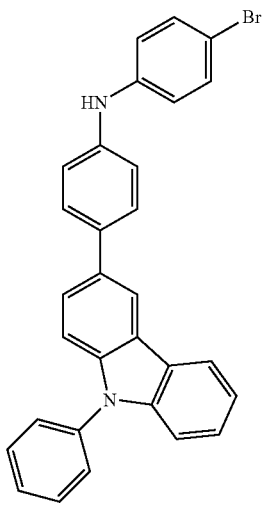
H-1-3
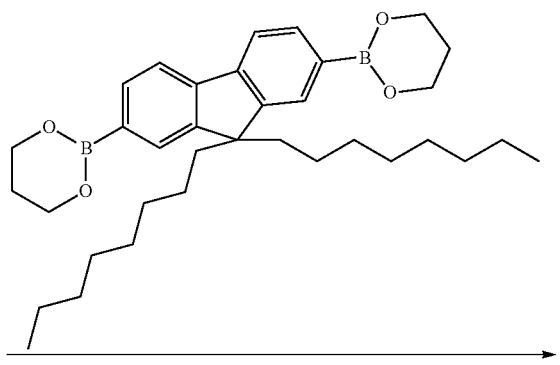
-continued
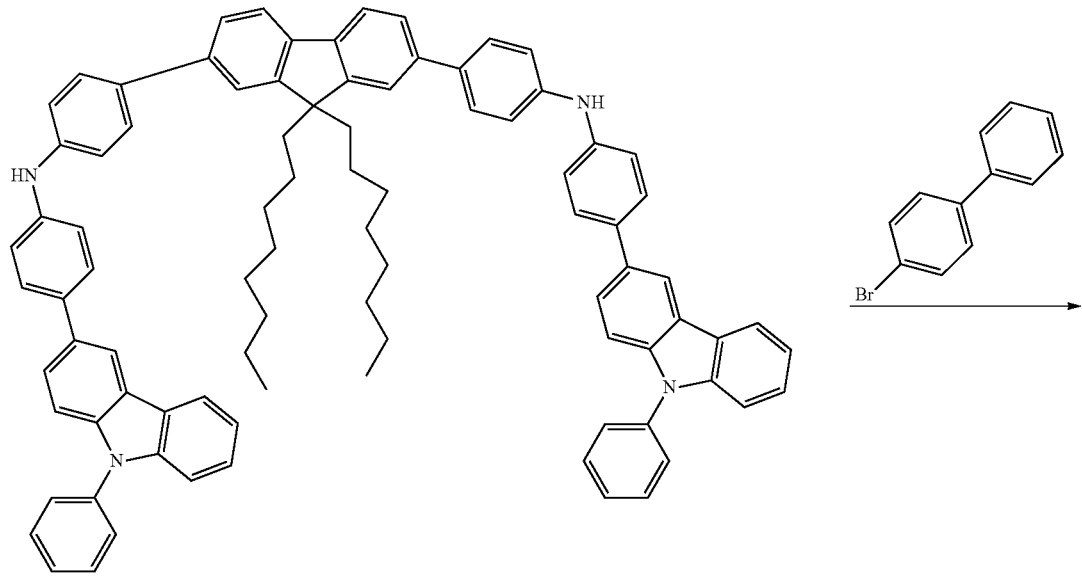
H-1-4

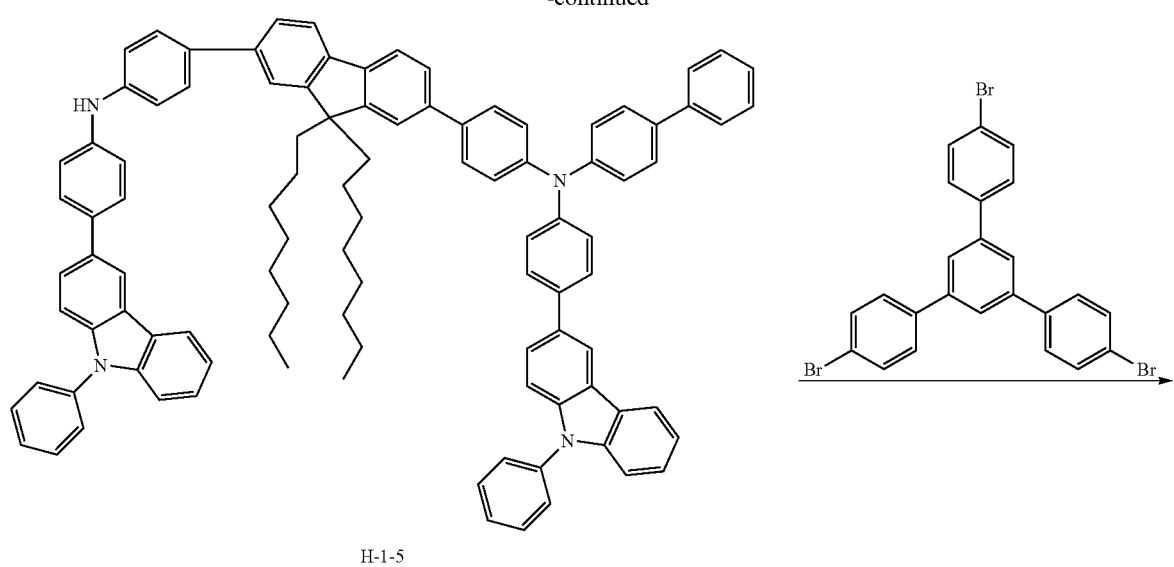
H-1-5
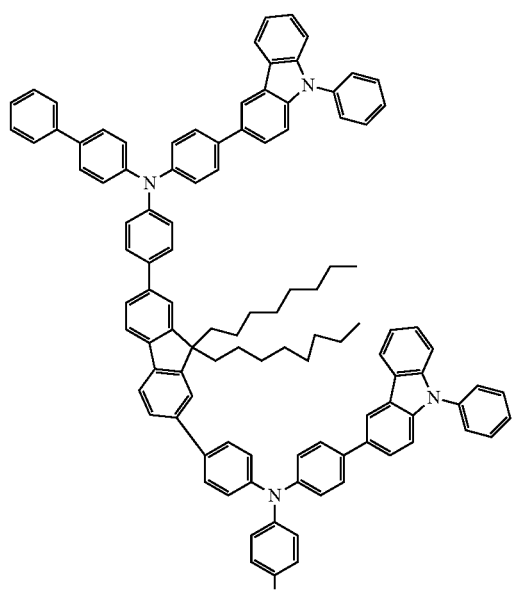

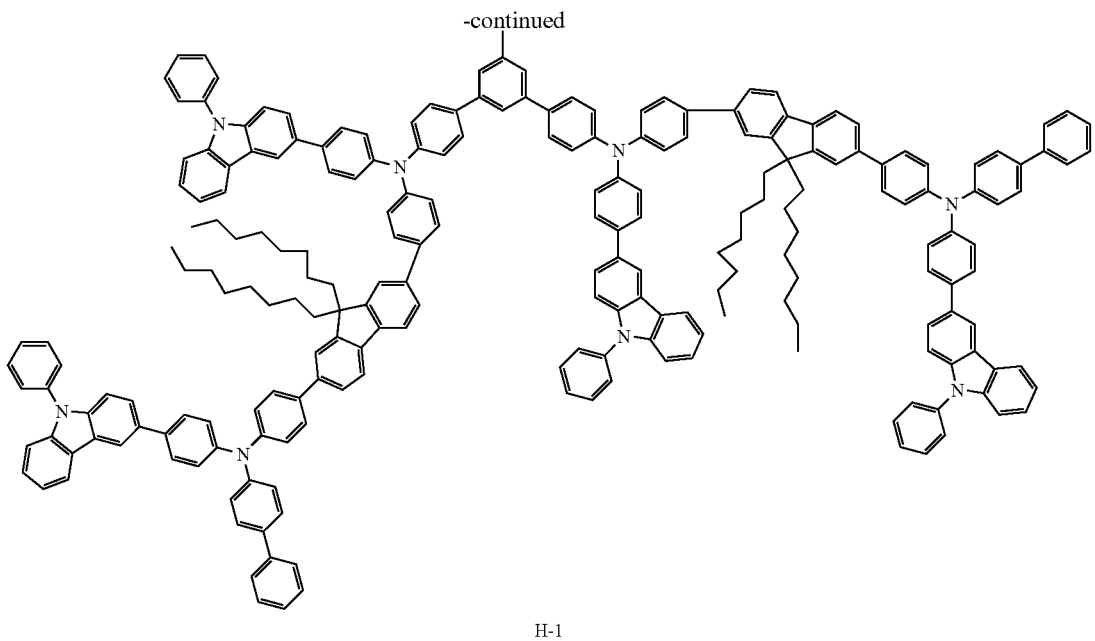

H-1

(1) Synthesis of Intermediate H-1-1

5.90 mL of sulfuric acid and 75 mL of ethanol were added to 17.7 g of 9-phenylcarbazole, 6.03 g of potassium iodide and 7.78 g of potassium iodate, and the mixture was reacted at 75° C. for 2 hours.

After cooling, water and ethyl acetate were added to the resulting solution, followed by separating and extraction. Then, the extracted organic phase was washed with sodium bicarbonate water and water, and then concentrated. The crude product obtained was purified by silica-gel chromatography (toluene). The resulting solids were dried under reduced pressure to obtain 21.8 g of white solids.

By Field Desorption Mass Spectrometry (hereinafter referred to as FD-MS), the white powder obtained was confirmed to be the intermediate H-1-1.

(2) Synthesis of Intermediate H-1-2

Under an argon atmosphere, dehydrated THF (300 mL) was added to 13.1 g of the intermediate H-1-1, and the mixture was cooled to −45° C. To the mixture, 25 mL of a solution of n-butyllithium in hexane (1.58M) was added dropwise, and the resulting solution was heated to −5° C. over an hour while stirring. The resulting solution was cooled to −45° C. again, and 25 mL of triisopropyl borate ester was added dropwise slowly and reacted for 2 hours.

A dilute hydrochloric acid solution (10%) was added and stirred to extract an organic phase. The organic phase was washed with saturated saline, and then dried with anhydrous magnesium sulfate, followed by filtration and concentration. The white powder obtained was purified by silica-gel chromatography. The resulting solids were washed with n-hexane, and dried under reduced pressure to obtain 7.10 g of white powder.

By FD-MS, the white powder obtained was confirmed to be the intermediate H-1-2.

(3) Synthesis of Intermediate H-1-3

Under an argon atmosphere, at room temperature, 17.2 g of the intermediate H-1-2, 19.6 g of bis(4-bromophenyl) amine and 3.47 g of Pd(PPh$_3$)$_4$ were stirred in 700 mL of DME. An aqueous solution of sodium carbonate (sodium carbonate: 42.1 g, distilled water: 350 mL) was dropped to the mixture. The resulting solution was stirred for 11 hours while heating under reflux. After completion of reaction, the water phase was removed. The organic layer was dried with sodium sulfate and then concentrated. The residue was purified by silica-gel column chromatography to obtain 10.2 g of white powder.

By FD-MS, the white powder obtained was confirmed to be the intermediate H-1-3.

(4) Synthesis of Intermediate H-1-4

Under an argon atmosphere, at room temperature, 10.2 g of the intermediate H-1-3, 5.25 g of 2,2'-(9,9-dioctyl-9H-fluorene-2,7-diyl)bis(1,3,2-dioxaborolane) and 1.09 g of Pd(PPh$_3$)$_4$ were stirred in 120 mL of THF. A sodium carbonate solution (sodium carbonate: 13.2 g, distilled water: 60 mL) was dropped to the mixture. The resulting solution was stirred for 13 hours while heating under reflux. After completion of reaction, the water phase was removed. The organic phase was dried with sodium sulfate and then concentrated. The residue was purified by silica-gel column chromatography to obtain 10.1 g of pale yellow powder.

By FD-MS, the white powder obtained was confirmed to be the intermediate H-1-4.

(5) Synthesis of Intermediate H-1-5

Under an argon atmosphere, at room temperature, 0.03 g of palladium acetate and 0.17 g of tri(tert-butyl)phosphine were stirred in 30 mL of toluene. Subsequently, 9.82 g of the intermediate H-1-4, 1.90 g of 4-bromobiphenyl and 60 mL of toluene were charged, and the mixture was heated to 90° C. Further, 1.09 g of t-BuONa was added, followed by stirring at 105° C. for 9 hours. After completion of the reaction, 100 mL of water was added and then the mixture was separated to remove the water phase. The organic phase was dried with sodium sulfate, followed by concentration. The residue was purified by silica-gel column chromatography to obtain 4.07 g of white powder.

By FD-MS, the pale yellow powder obtained was confirmed to be the intermediate H-1-5.

(6) Synthesis of Compound H-1

Under an argon atmosphere, at room temperature, 0.01 g of palladium acetate and 0.05 g of tri(tertiary butyl)phosphine were stirred in 3 mL of toluene. Subsequently, 3.79 g of the intermediate H-1-5, 0.46 g of 1,3,5-tris(p-bromophenyl)benzene and 7 mL of toluene were charged, and the mixture was heated to 90° C. Further, 0.34 g of t-BuONa was added, followed by stirring at 105° C. for 9 hours. After completion of the reaction, 10 mL of water was added and then the mixture was separated to remove the water phase. The organic phase was dried with sodium sulfate, followed by concentration. The residue was purified by silica-gel column chromatography to obtain 3.58 g of pale yellow powder.

By FD-MS, the pale yellow powder obtained was confirmed to be the compound H-1, which is an intended substance.

Example 2

A compound H-2 was synthesized by the following synthesis scheme.

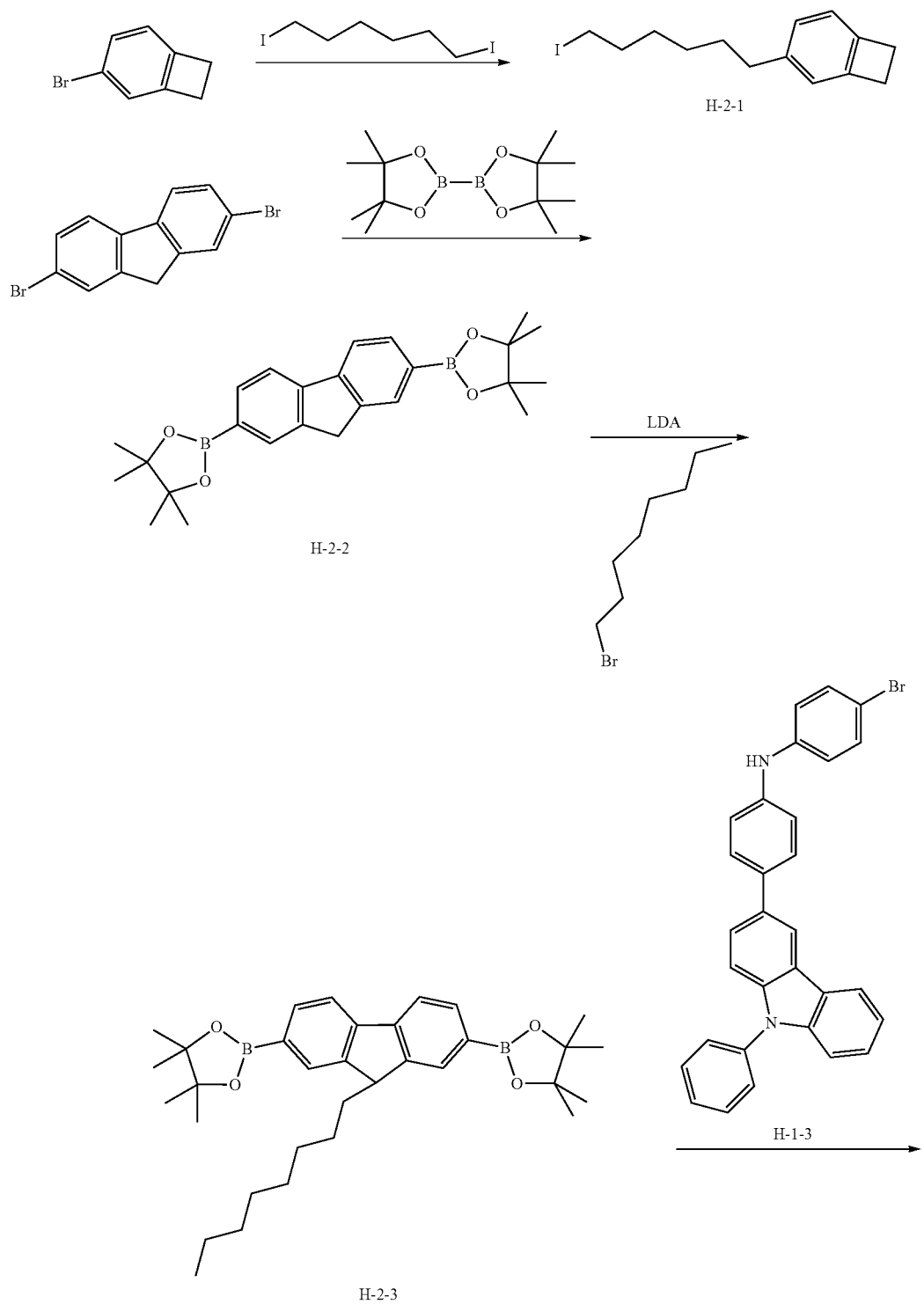

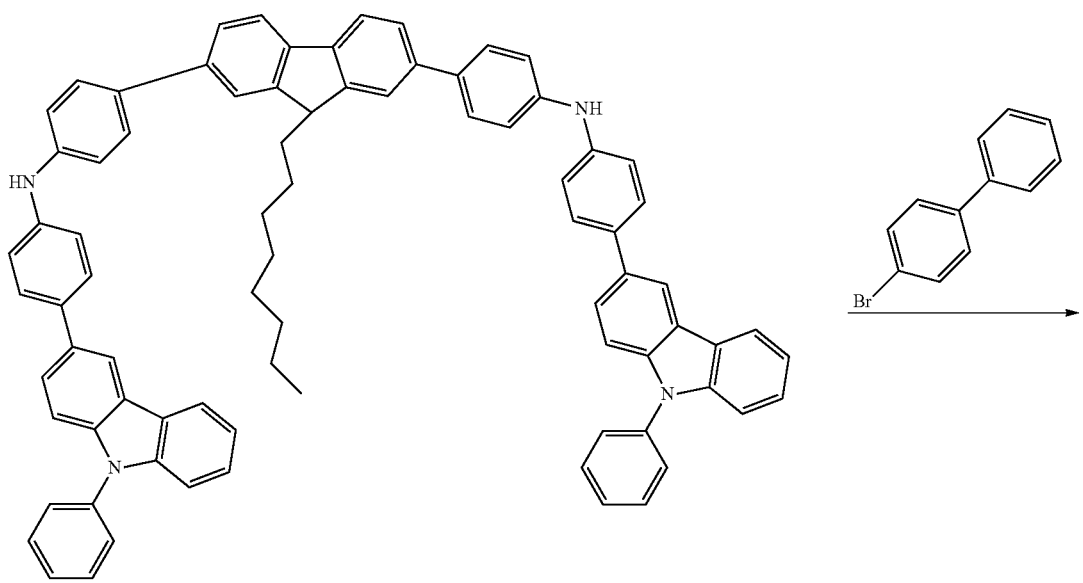
H-2-4
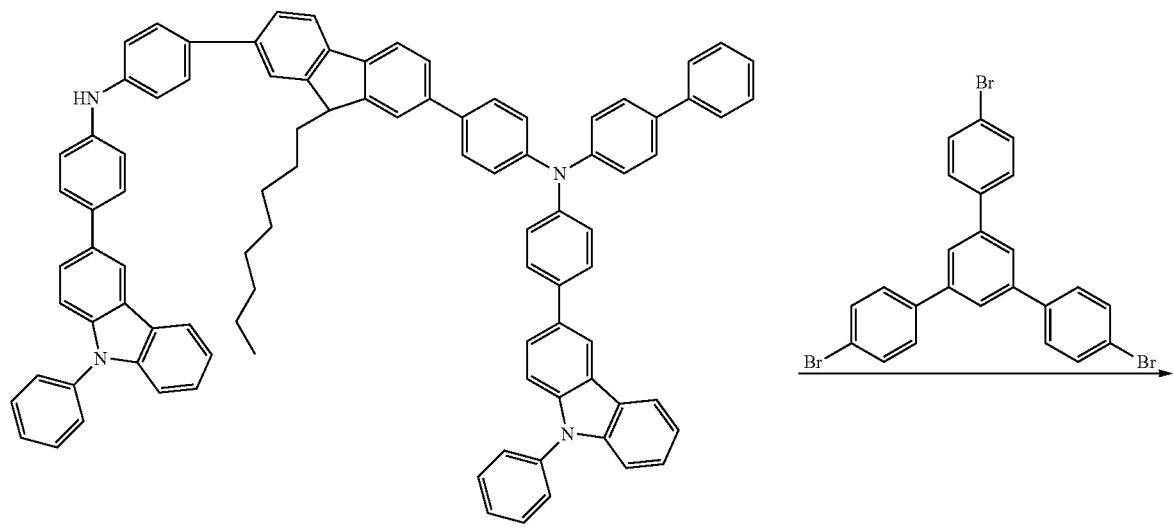
H-2-5

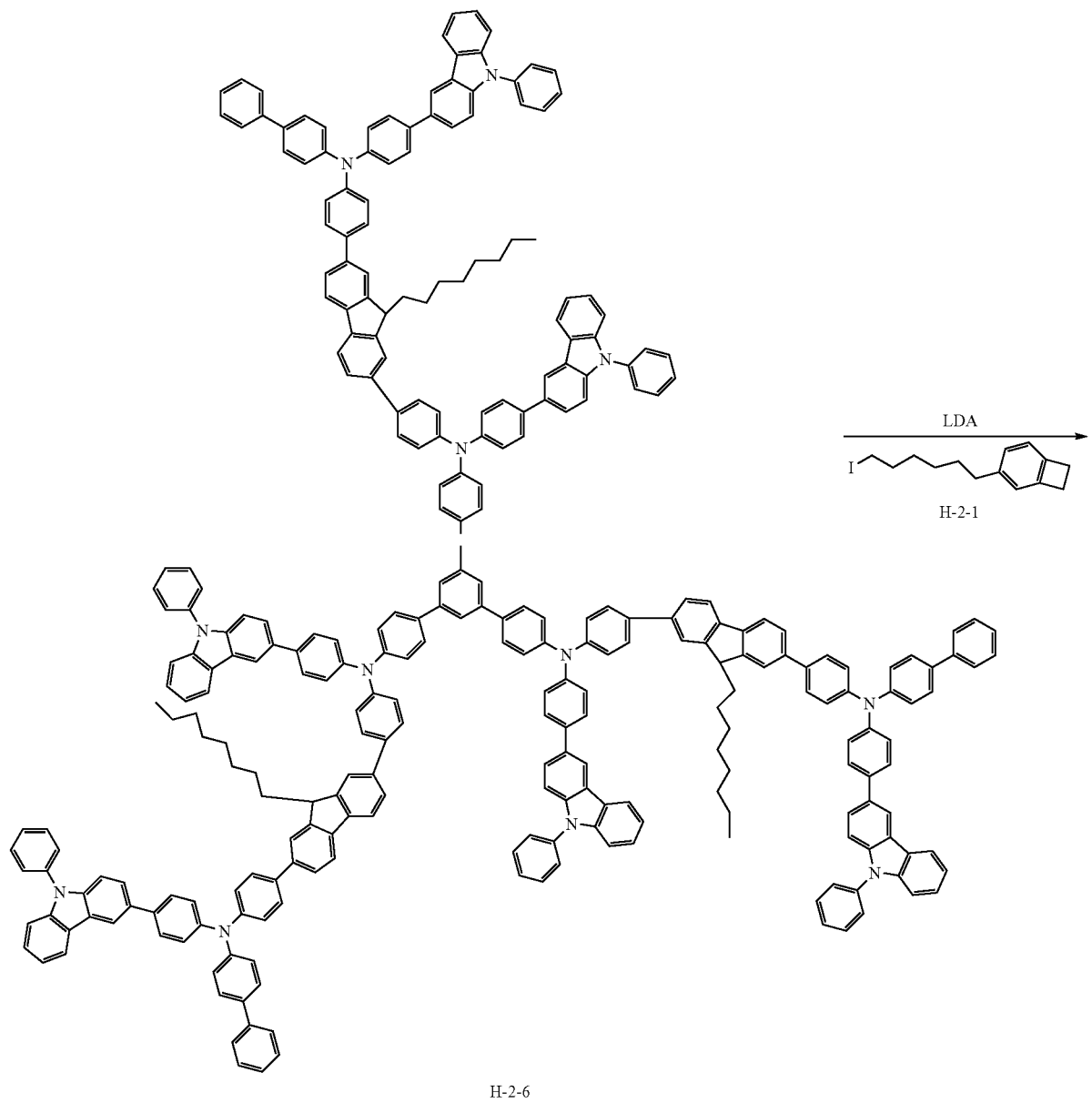
H-2-6

-continued

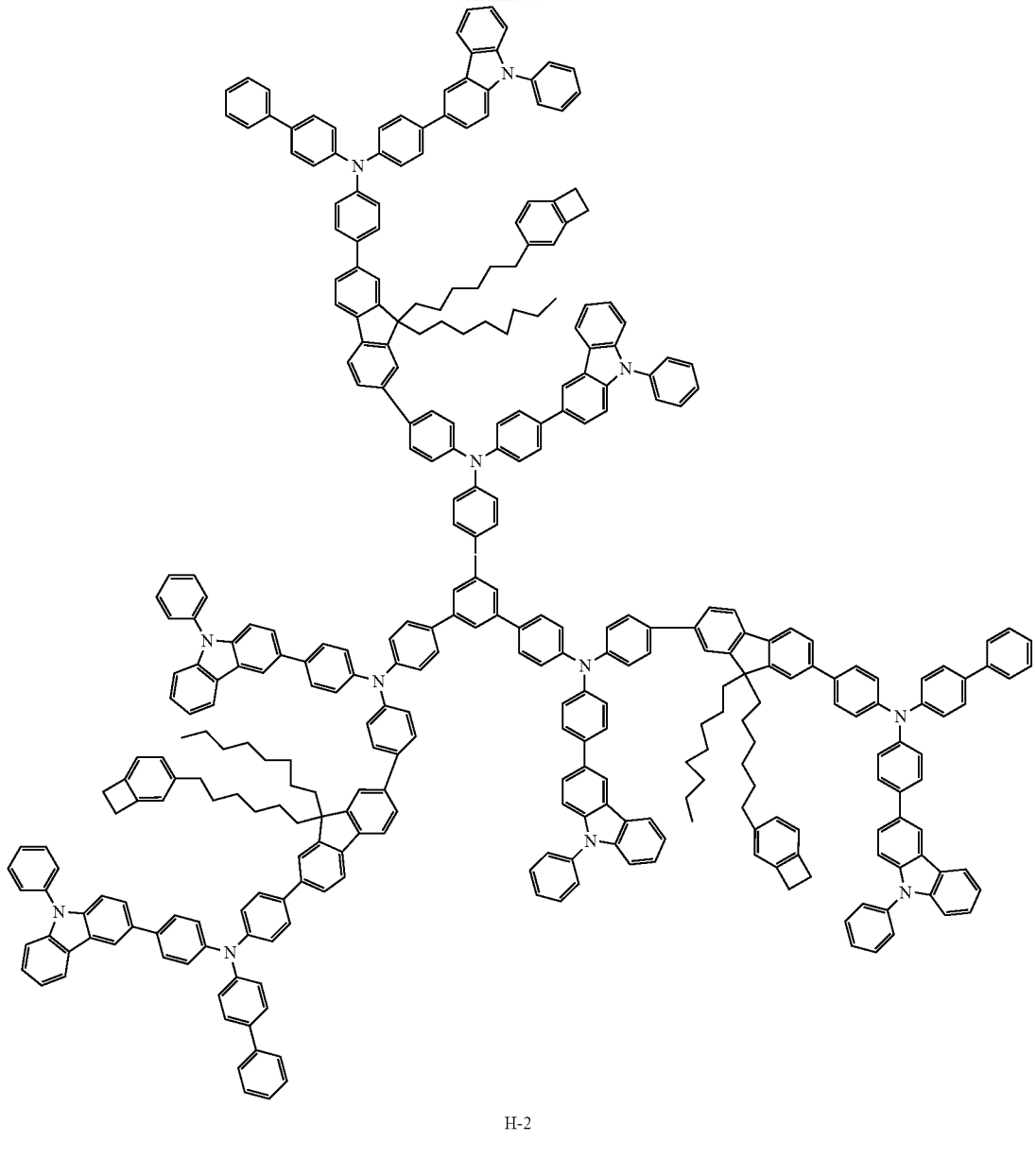

H-2

(1) Synthesis of Intermediate H-2-1

Under an argon stream, 300 mL of dehydrated THF was added to 18.3 g of 4-bromo-1,2-dihydrocyclobutabenzene, and the mixture was cooled to −78° C. To the mixture, 130 mL of a solution of n-butyl lithium in hexane (1.58M) was added dropwise. After the resulting solution was stirred for an hour, 16.5 mL of 1,6-diiodohexane was added dropwise slowly. The mixture was heated to room temperature for an hour, and further reacted for 2 hours.

A dilute hydrochloric acid solution (10%) was added and stirred to extract an organic phase. The organic phase was washed with saturated saline, and then dried with anhydrous magnesium sulfate, followed by filtration and concentration. The resulting solids were purified by silica-gel column chromatography, and dried under reduced pressure to obtain 12.6 g of colorless liquid.

By FD-MS, the white powder obtained was confirmed to be the intermediate H-2-1.

(2) Synthesis of Intermediate H-2-2

1000 mL of DMSO was added to the mixture of 32.4 g of 2,7-dibromo-9H-fluorene, 57.4 g of 4,4,4',4',5,5,5',5'-octamethyl-2,2'-bis(1,3,2-dioxaborolane), 4.90 g of 1,1-'bis(diphenylphosphino)ferrocene-palladium(11)dichloride-dichloromethane complex ($PdCl_2dppf \cdot CH_2Cl_2$) and 61.0 g of potassium acetate, and reacted at 80° C. for 18 hours.

After cooling, water and ethyl acetate were added to the resultant, followed by separation and extraction. Subsequently, the organic phase was washed with water, and concentrated. The crude product obtained was purified by silica-gel column chromatography. The resulting solids were dried under reduced pressure to obtain 25.1 g of white solids.

By FD-MS, the white solids obtained were confirmed to be the intermediate H-2-2.

(3) Synthesis of Intermediate H-2-3

Under an argon atmosphere, 120 mL of dehydrated THF was added to 12.5 g of the intermediate H-2-2, and the mixture was cooled to −78° C. To the mixture, 27 mL of a solution of lithium diisopropylamide (LDA) in hexane/THF (1.11M) was added dropwise. After the resulting solution was stirred for an hour, 5.2 mL of octylbromide was dropped slowly. The mixture was heated to room temperature over an hour, and further reacted for 2 hours.

A dilute hydrochloric acid solution (10%) was added and stirred to extract an organic phase. The organic phase was washed with saturated saline, and then dried with anhydrous magnesium sulfate, followed by filtration and concentration. The resulting solids were purified by silica-gel column chromatography, and dried under reduced pressure to obtain 12.2 g of white powder.

By FD-MS, the white powder obtained was confirmed to be the intermediate H-2-3.

(4) Synthesis of Intermediate H-2-4

Under an argon atmosphere, at room temperature, 20.6 g of the intermediate H-1-3, 11.2 g of the intermediate H-2-3 and 2.44 g of Pd(PPh$_3$)$_4$ were stirred in 260 mL of THF. A sodium carbonate solution (sodium carbonate: 29.6 g, distilled water: 130 mL) was dropped to the mixture. The resulting solution was stirred for 15 hours while heating under reflux. After completion of the reaction, a water phase was removed. The organic phase was dried with sodium sulfate and then concentrated. The residue was purified by silica-gel column chromatography to obtain 6.24 g of pale yellow powder.

By FD-MS, the pale yellow powder obtained was confirmed to be the intermediate H-2-4.

(5) Synthesis of Intermediate H-2-5

Under an argon atmosphere, at room temperature, 0.027 g of palladium acetate and 0.11 g of tri(tertiary butyl)phosphine were stirred in 15 mL of toluene. Subsequently, 6.20 g of the intermediate H-2-4, 1.32 g of 4-bromobiphenyl and 35 mL of toluene were charged, and the mixture was heated to 90° C. Further, 0.77 g of t-BuONa was added, followed by stirring at 105° C. for 9 hours. After completion of the reaction, 50 mL of water was added and then the mixture was separated to remove a water phase. The organic phase was dried with sodium sulfate, followed by concentration. The residue was purified by silica-gel column chromatography to obtain 3.20 g of white powder.

By FD-MS, the pale yellow powder obtained was confirmed to be the intermediate H-2-5.

(6) Synthesis of Intermediate H-2-6

Under an argon atmosphere, at room temperature, 0.01 g of palladium acetate and 0.05 g of tri(tertiary butyl)phosphine were stirred in 3 mL of toluene. Subsequently, 3.19 g of the intermediate H-2-5, 0.42 g of 1,3,5-tris(p-bromophenyl)benzene and 7 mL of toluene were charged, and the mixture was heated to 90° C. Further, 0.31 g of t-BuONa was added, followed by stirring at 105° C. for 9 hours. After completion of the reaction, 10 mL of water was added and then the mixture was separated to remove a water phase. The organic phase was dried with sodium sulfate, followed by concentration. The residue was purified by silica-gel column chromatography to obtain 2.57 g of pale yellow powder.

By FD-MS, the pale yellow powder obtained was confirmed to be the intermediate H-2-6.

(7) Synthesis of Compound H-2

Under an argon atmosphere, dehydrated THF was added to 2.57 g of the intermediate H-2-6, and the mixture was cooled to −78° C. To the mixture, 2.9 mL of a solution of LDA in hexane/THF (1.11M) was added dropwise. After the resulting solution was stirred for an hour, 0.6 mL of the intermediate 2-H-1 was dropped slowly. The mixture was heated to room temperature over an hour, and further reacted for 2 hours.

A dilute hydrochloric acid solution (10%) was added and stirred to extract an organic phase. The organic phase was washed with saturated saline, and then dried with anhydrous magnesium sulfate, followed by filtration and concentration. The resulting solids were purified by silica-gel column chromatography, and dried under reduced pressure to obtain 1.70 g of pale yellow powder.

By FD-MS, the pale yellow powder obtained was confirmed to be the intermediate H-2, which is an intended substance.

Example 3

Fabrication and Evaluation of Organic EL Device

A glass substrate, measuring 25 mm×75 mm×1.1 mm thick, with an ITO transparent electrode (manufactured by Geomatics Co.) was subjected to ultrasonic cleaning in isopropyl alcohol for 5 minutes and then UV ozone cleaning for 30 minutes. On the cleaned glass substrate with transparent electrode lines, a mixture of polyethylenedioxythiophene/polystyrenesulfonate (PEDOT:PSS) was formed into a 10 nm-thick film as a hole-injecting layer by spin coating (PSS: acceptor). Subsequently, as a hole-transporting material, a xylene solution (1.0% by weight) of the compound H-1 prepared in Example 1 was prepared and formed into a 40 nm-thick film by spin coating. After drying at 100° C. for 30 minutes, a homogeneous hole-transporting layer was obtained. Next, the compound EM1 and an amine compound (D1) having a styryl group were deposited such that the weight ratio of EM1 and D1 became 40:2 to form a 40 nm-thick film as an emitting layer. On this film, the following Alq was formed into a 10 nm-thick film. This layer functions as an electron-injecting layer. After that, Li as a reducing dopant (Li source: manufactured by SAES Getters Co., Ltd.) and Alq were co-deposited to form an Alq:Li film (film thickness: 10 nm) as an electron-injecting layer (cathode). On the Alq:Li layer, metal Al was deposited to form a metallic cathode. Glass sealing was conducted in nitrogen to fabricate an organic EL device.

The above-mentioned compound EM1, compound D1 and Alq are compounds having the following structure, respectively.

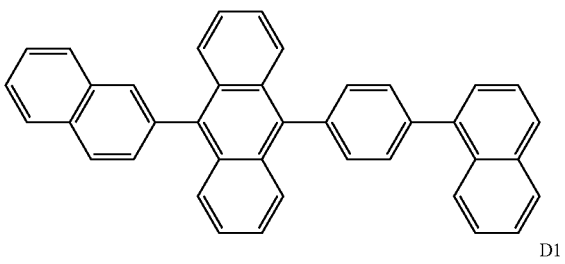

EM1

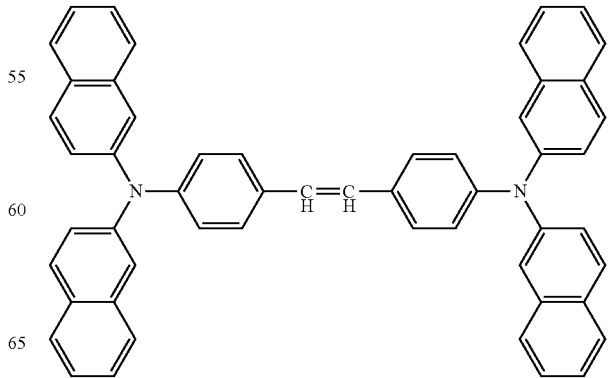

D1

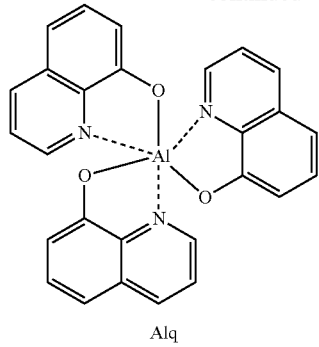

Alq

The fabricated organic EL device was evaluated by applying an electric current. The organic EL device emitted blue, and had a luminous efficiency of 6.9 cd/A, and a luminance half-decay lifetime (LT50) at room temperature of 3500 hr@1,000 cd/m². When the fabricated organic EL device was driven in an oven heated to 60° C., the luminance half-decay lifetime (LT50) was 1,700 hr@1,000 cd/m². Therefore, the ratio of the luminance half-decay lifetime at 60° C. to that at room temperature was 0.48.

Comparative Example 1

An organic EL device was fabricated in the same manner as in Example 3, except that a comparative compound 1 was used instead of the compound H-1 as a hole-transporting layer.

The solubility of the comparative compound 1 in xylene was insufficient, and hence, the hole-transporting layer obtained was inhomogeneous.

Comparative compound 1

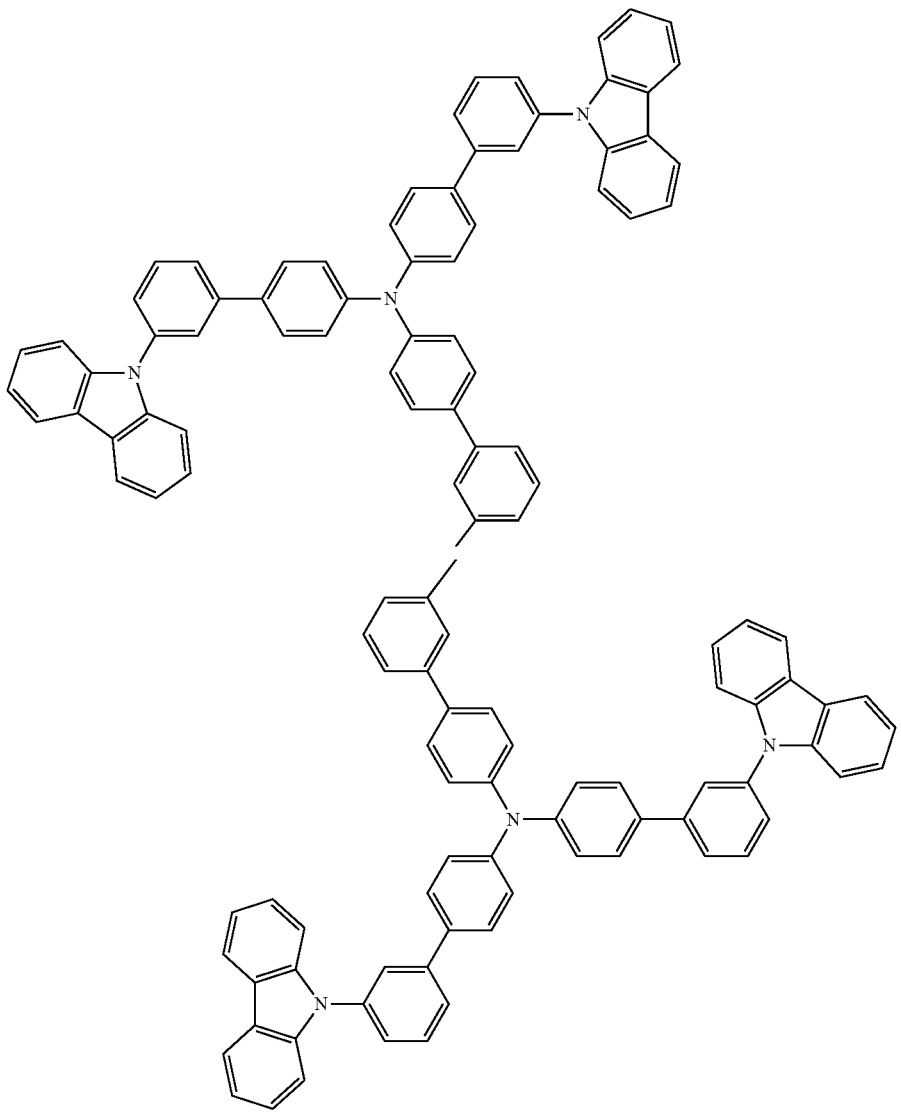

The fabricated organic EL device was evaluated by applying an electric current. The organic EL device emitted blue, and had a luminous efficiency of 2.3 cd/A, and a luminance half-decay lifetime (LT50) at room temperature of 500 hr@1,000 cd/m². When the fabricated organic EL device was driven in an oven heated to 60° C., the luminance half-decay lifetime (LT50) was 100 hr@1,000 cd/m². Therefore, the ratio of the luminance half-decay lifetime at 60° C. to that at room temperature was 0.20.

Comparative Example 2

An organic EL device was fabricated in the same manner as in Example 3, except that the following comparative compound 2 was used instead of the compound H-1 as a hole-transporting material. However, the hole-transporting layer obtained were strongly heterogeneous, and hence, the fabricated organic EL device could not emit light due to the leakage of current.

Comparative compound 2

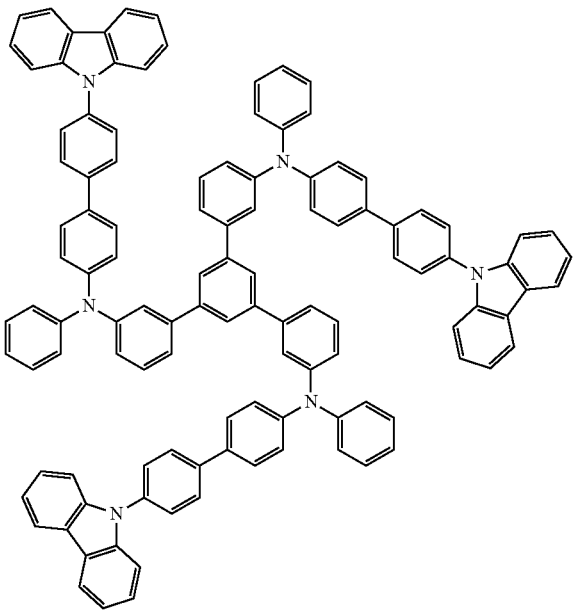

Example 4

Fabrication and Evaluation of Organic EL Device

A glass substrate, measuring 25 mm×75 mm×1.1 mm thick, with an ITO transparent electrode (manufactured by Geomatics Co.) was subjected to ultrasonic cleaning in isopropyl alcohol for 5 minutes and then UV ozone cleaning for 30 minutes. On the cleaned glass substrate with transparent electrode lines, a mixture of polyethylenedioxythiophene/polystyrenesulfonate (PEDOT:PSS) was formed into a 10 nm-thick film as a hole-injecting layer by spin coating (PSS: acceptor). Subsequently, as a polymerizable monomer, a xylene solution (1.0% by weight) of the monomer H-2 obtained in Example 2 was formed into a 40 nm-thick film by spin coating. Drying at 230° C. for 30 minutes and heat hardening were conducted to form a hole-transporting layer. Next, a xylene solution (1.0% by weight) in which the compound EM1 (host) and the amine compound (D1) having a styryl group (dopant) were mixed at the solid matter weight ratio of 95:5 was formed into a 40 nm-thick film by spin coating, dried at 150° C. for 30 minutes to obtain an emitting layer. On this film, Alq was deposited to form a 10 nm-thick film. This layer functions as an electron-injecting layer. After that, Li as a reducing dopant (Li source: manufactured by SAES Getters Co., Ltd.) and Alq were co-deposited to form an Alq:Li film (film thickness: 10 nm) as an electron-injecting layer (cathode). On the Alq:Li film, metal Al was deposited to form a metallic cathode. Glass sealing was conducted in nitrogen to fabricate an organic EL device.

The fabricated organic EL device was evaluated by applying an electric current. The organic EL device emitted blue, and had a luminous efficiency of 5.3 cd/A, and a luminance half-decay lifetime (LT50) at room temperature of 1,500 hr@1,000 cd/m². When the fabricated organic EL device was driven in an oven heated to 60° C., the luminance half-decay lifetime (LT50) was 600 hr@1,000 cd/m². Therefore, the ratio of the luminance half-decay lifetime at 60° C. to that at room temperature was 0.40.

Example 5

An organic EL device was fabricated and evaluated in the same manner as in Example 4, except that the following arylamine compound D2 was used instead of the amine compound D1 having a styryl group as an emitting material.

The fabricated organic EL device was evaluated by applying an electric current. The organic EL device emitted blue, and had a luminous efficiency of 5.6 cd/A, and a luminance half-decay lifetime (LT50) at room temperature of 1,500 hr@1,000 cd/m². When the fabricated organic EL device was driven in an oven heated to 60° C., the luminance half-decay lifetime (LT50) was 600 hr@1,000 cd/m². Therefore, the ratio of the luminance half-decay lifetime at 60° C. to that at room temperature was 0.40.

D2

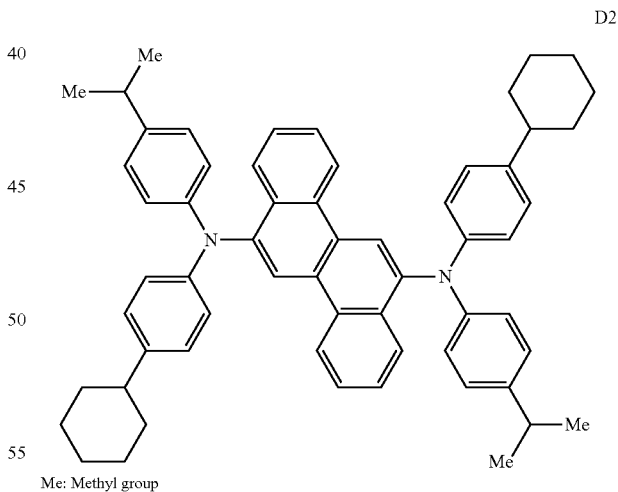

Me: Methyl group

Comparative Example 3

In Example 4, by using a xylene solution of the following compound X1 (1.0% by weight) as a hole-transporting material, instead of a xylene solution of the compound H-2 (1.0% by weight), an attempt was made to form a film. However, the film was crystallized, and hence, a homogeneous hole-transporting layer could not be formed.

X-1

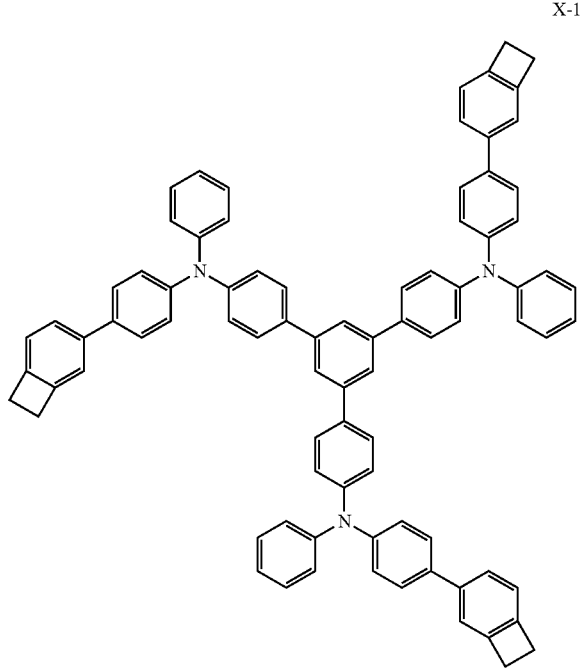 [SMILES: c1ccc(N(c2ccc(-c3cc(-c4ccc(N(c5ccccc5)c5ccc(-c6ccc7c(c6)CC7)cc5)cc4)cc(-c4ccc(N(c5ccccc5)c5ccc(-c6ccc7c(c6)CC7)cc5)cc4)c3)cc2)c2ccc(-c3ccc4c(c3)CC4)cc2)cc1]

Comparative Example 4

An organic EL device was fabricated in the same manner as in Example 4, except that the following monomer X-2 disclosed in JP-2008-218983A was used instead of the compound H-2 as a hole-transporting material.

The fabricated organic EL device was evaluated by applying an electric current. The organic EL device emitted blue, and had a luminous efficiency of 3.0 cd/A, and a luminance half-decay lifetime (LT50) at room temperature of 600 hr@1,000 cd/m². When the fabricated organic EL device was driven in an oven heated to 60° C., the luminance half-decay lifetime (LT50) was 150 hr@1,000 cd/m². Therefore, the ratio of the luminance half-decay lifetime at 60° C. to that at room temperature was 0.25.

Example 6

An organic EL device was fabricated in the same manner as in Example 3, except that the hole-transporting layer was formed in a film thickness of 25 nm by spin coating. As a result, a homogeneous hole-transporting layer was obtained.

Example 7

An organic EL device was fabricated in the same manner as in Example 4, except that the hole-transporting layer was formed in a film thickness of 25 nm by spin coating. As a result, a homogeneous hole-transporting layer was obtained.

The results of Examples 1 to 5 and Comparative Examples 1 to 4 show that an organic EL device using an aromatic amine derivative of the invention has an excellent luminous efficiency and a prolonged lifetime as compared with an organic EL device using comparative compounds which are also an aromatic amine derivative. In addition, in the organic EL device of the invention, the life time is shortened only slightly even if it is driven at high temperatures.

Further, the results of Examples 6 and 7 show that use of an aromatic derivative of the invention enables formation of a homogeneous and thin hole-transporting layer.

INDUSTRIAL APPLICABILITY

The present invention can provide an aromatic amine derivative or the like, which is useful as a hole injecting/transporting material in an organic device, in particular, an organic EL device or the like. Further, the present invention can provide an organic EL device which has excellent properties such as a prolonged life and a high luminous efficiency, and suffers only slight deterioration even when subjected to high-temperature driving which is practical in the applications of a display and an illumination, and hence, it is suitable for practical use.

Although only some exemplary embodiments and/or examples of this invention have been described in detail above, those skilled in the art will readily appreciate that many modifications are possible in the exemplary embodiments and/or examples without materially departing from

X-2

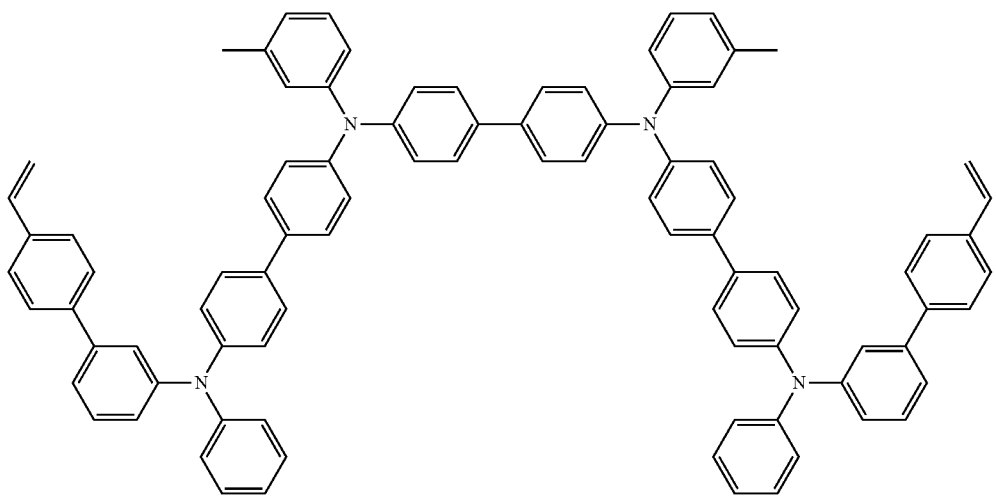

The novel teachings and advantages of this invention. Accordingly, all such modifications are intended to be included within the scope of this invention.

The documents described in the Japanese application specification claiming priority under the Paris Convention and the United State provisional application specification are incorporated herein by reference in its entirety.

The invention claimed is:
1. An aromatic amine derivative represented by the following formula (1):

$$[Z_1]_n L_1 \quad (1)$$

wherein $Z_1$ is a group represented by the following formula (2);
$L_1$ is a group represented by any of the following formulas:

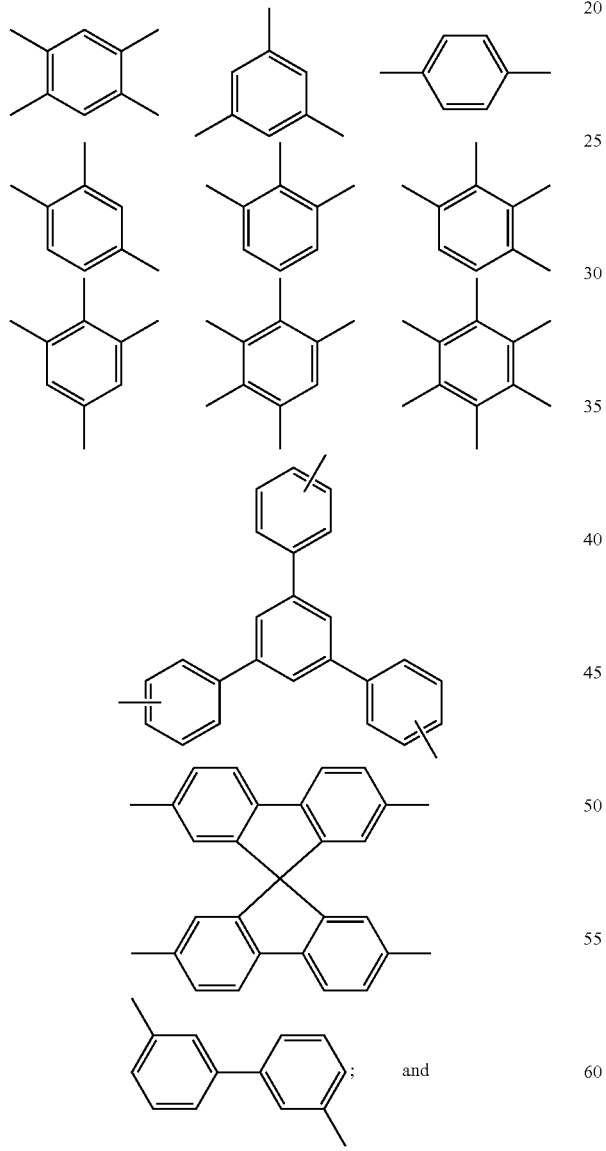

n is an integer of 2 to 10:

$$[Z_2]_m L_2 \quad (2)$$

wherein $Z_2$ is a group represented by the following formula (3) or (3');
$L_2$ is a group represented by the following formula:

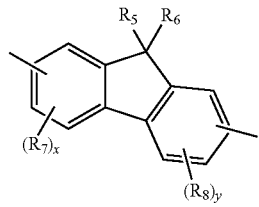

wherein $R_5$, $R_6$, $R_7$ and $R_8$ are independently a hydrogen atom, a liner or branched alkyl group including 1 to 20 carbon atoms, a liner or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms;
$R_5$ and $R_6$ and/or $R_7$ and $R_8$ may be bonded to each other to form a saturated or unsaturated ring;
x and y are an integer of $1 \leq x \leq 3$ and an integer of $1 \leq y \leq 3$, respectively, and when x is 2 or 3, each $R_7$ may be the same or different, and when y is 2 or 3, each $R_8$ may be the same or different;
$L_1$ in the formula (1) bonds to any of $Z_2$ and $L_2$; and
m is an integer of 2 to 10:

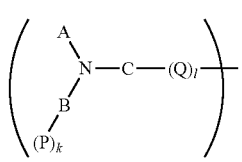

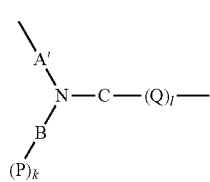

wherein in the formulas (3) and (3'),
A is a hydrogen atom, a substituted or unsubstituted aromatic hydrocarbon group including 6 to 25 ring carbon atoms, a substituted or unsubstituted aromatic heterocyclic group including 5 to 25 ring atoms or a group formed of plural rings;
A' is a single bond, a substituted or unsubstituted aromatic hydrocarbon group including 6 to 25 ring carbon atoms, a substituted or unsubstituted aromatic heterocyclic group including 5 to 25 ring atoms or a group formed of plural rings;
B is a single bond, a substituted or unsubstituted aromatic hydrocarbon group including 6 to 25 ring carbon atoms, a substituted or unsubstituted aromatic heterocyclic group including 5 to 25 ring atoms or a group formed of plural rings;

C is a single bond, a substituted or unsubstituted aromatic hydrocarbon group including 6 to 25 ring carbon atoms, a substituted or unsubstituted aromatic heterocyclic group including 5 to 25 ring atoms or a group formed of plural rings;

P and Q are independently a substituted or unsubstituted aromatic hydrocarbon group including 6 to 25 ring carbon atoms, a substituted or unsubstituted aromatic heterocyclic group including 5 to 25 ring atoms, a group formed of plural rings or a group represented by the following formula (4) or (5);

when $Z_2$ is represented by the formula (3), $L_2$ bonds to any of A, B, C, P and Q, and when $Z_2$ is represented by the formula (3'), $L_2$ bonds to A'; and k and l are independently an integer of 0 or 1, and $k+l \geq 1$:

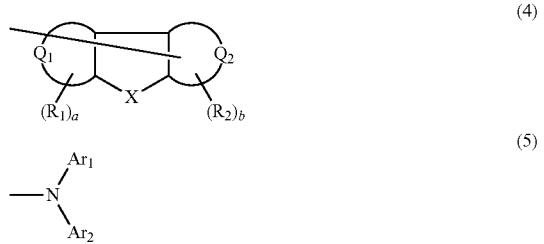

wherein in the formula (4), X is —O—, —S—, or —N($R_a$)—, $R_a$ is an atom or a group selected from a hydrogen atom, a substituted or unsubstituted linear or branched alkyl group including 1 to 20 carbon atoms, a substituted or unsubstituted linear or branched alkenyl group including 2 to 20 carbon atoms, a substituted or unsubstituted cycloalkyl group including 3 to 20 carbon atoms, a trialkylsilyl group of which the alkyl parts are each a substituted or unsubstituted alkyl group including 1 to 20 carbon atoms, a triarylsilyl group of which the aryl parts are each a substituted or unsubstituted aryl group including 6 to 24 ring carbon atoms, an alkylarylsilyl group including a substituted or unsubstituted alkyl group including 1 to 20 carbon atoms and a substituted or unsubstituted aryl group including 6 to 24 ring carbon atoms, a substituted or unsubstituted aryl group including 6 to 25 ring carbon atoms and a substituted or unsubstituted heteroaryl group including 5 to 24 ring atoms;

$R_1$ and $R_2$ are independently an atom or a group selected from a substituted or unsubstituted linear or branched alkyl group including 1 to 20 carbon atoms, a substituted or unsubstituted linear or branched alkenyl group including 2 to 15 carbon atoms, a substituted or unsubstituted cycloalkyl group including 3 to 20 carbon atoms, a trialkylsilyl group of which the alkyl parts are each a substituted or unsubstituted alkyl group including 1 to 20 carbon atoms, a triarylsilyl group of which the aryl parts are each a substituted or unsubstituted aryl group including 6 to 24 ring carbon atoms, an alkylarylsilyl group including a substituted or unsubstituted alkyl group including 1 to 20 carbon atoms and a substituted or unsubstituted aryl group including 6 to 24 ring carbon atoms, a substituted or unsubstituted aryl group including 6 to 24 ring carbon atoms, a substituted or unsubstituted heteroaryl group including 5 to 24 ring atoms, a halogen atom and a cyano group, and adjacent $R_1$ groups, adjacent $R_2$ groups, and/or adjacent $R_1$ and $R_2$ may bond to each other to form a saturated or unsaturated ring;

a and b are independently an integer of 0 to 3 and $Q_1$ and Q2 are independently a group including 5 to 25 atoms which forms a saturated or unsaturated ring;

in the formula (5), $Ar_1$ and $Ar_2$ are independently a substituted or unsubstituted aromatic hydrocarbon group including 6 to 25 ring carbon atoms or a substituted or unsubstituted aromatic heterocyclic group including 5 to 25 ring atoms, and at least one of $Ar_1$ and $Ar_2$ is a group formed of plural rings including 9 to 40 ring carbon atoms or a fused aromatic ring group including 10 to 25 ring carbon atoms.

2. The aromatic amine derivative according to claim 1, wherein one or more selected from A and A' is a linkage group or a group comprising a group represented by any of the following formulas:

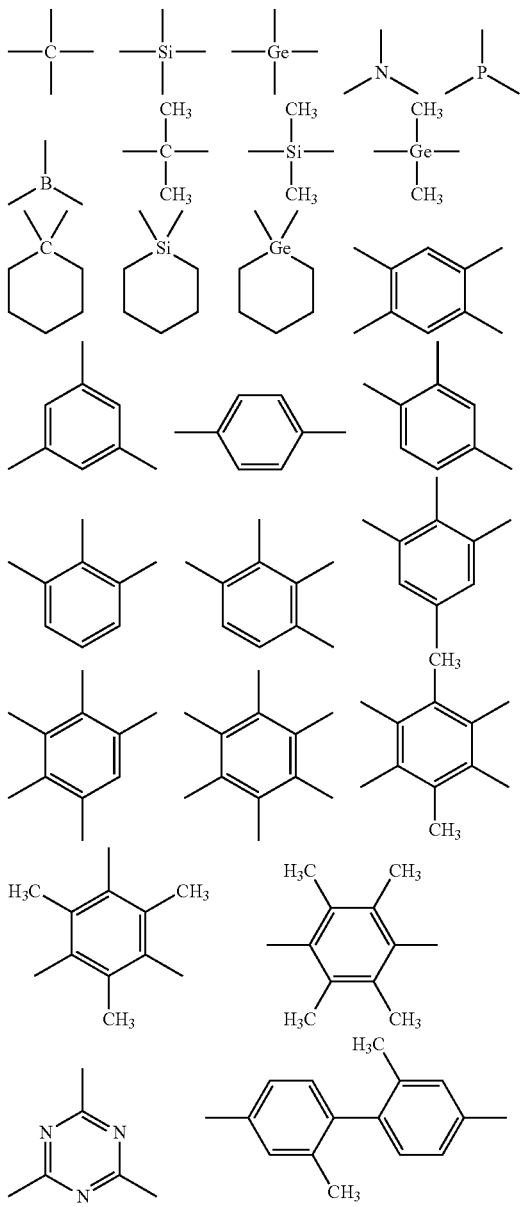

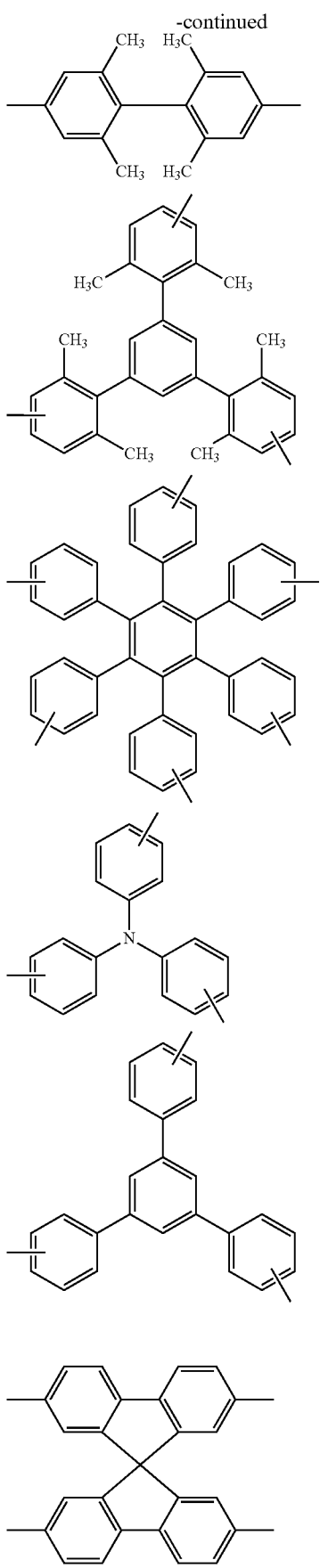

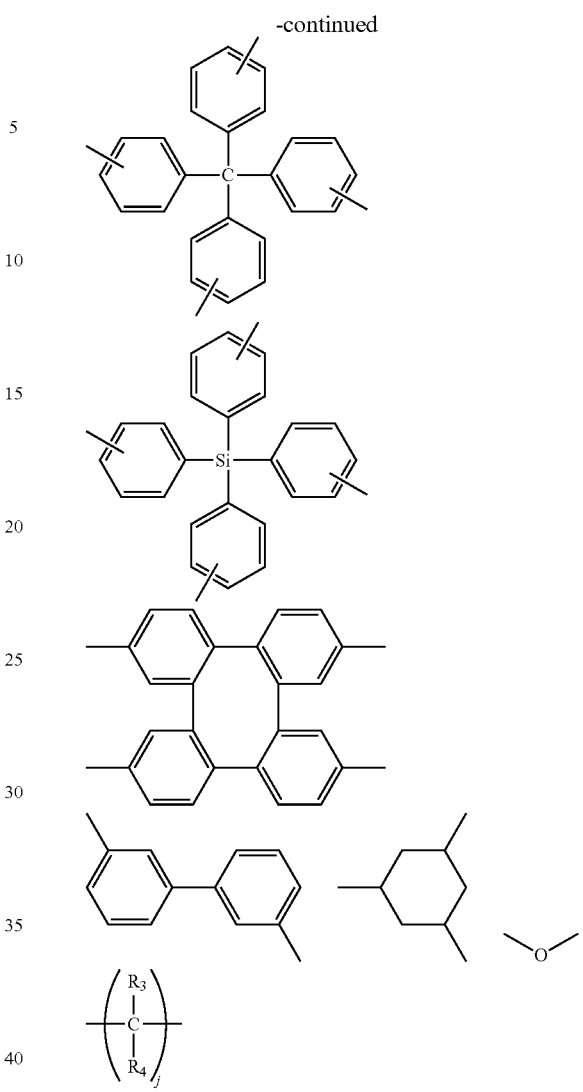

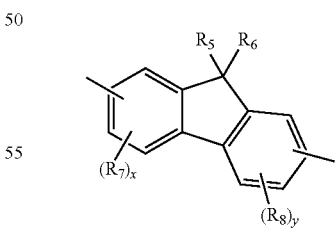

wherein $R_3$ and $R_4$ are independently a hydrogen atom, a methyl group, an ethyl group, a propyl group, an isopropyl group, a butyl group, an isobutyl group or a t-butyl group;

j is an integer of $2 \leq j \leq 20$, each $R_3$ may be the same or different, and each $R_4$ may be the same or different:

wherein $R_5$, $R_6$, $R_7$ and $R_8$ are independently a hydrogen atom, a liner or branched alkyl group including 1 to 20 carbon atoms, a liner or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms;

$R_5$ and $R_6$ and/or $R_7$ and $R_8$ may be bonded to each other to form a saturated or unsaturated ring;

x and y are an integer of $1 \leq x \leq 3$ and an integer of $1 \leq y \leq 3$, respectively, and when x is 2 or 3, each $R_7$ may be the same or different, and when y is 2 or 3, each $R_8$ may be the same or different:

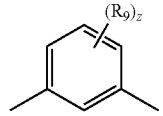

wherein $R_9$ is a hydrogen atom, a linear or branched alkyl group including 1 to 20 carbon atoms, a linear or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms; and z is an integer of $1 \leq z \leq 4$, and when z is 2, 3 or 4, each $R_9$ may be the same or different:

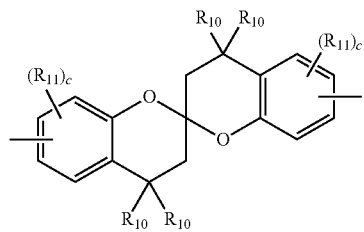

wherein $R_{10}$ and $R_{11}$ are independently a hydrogen atom, a linear or branched alkyl group including 1 to 20 carbon atoms, a linear or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms;

each $R_{10}$ and/or each $R_{11}$ may be bonded to each other to form a saturated or unsaturated ring; and c is an integer of $1 \leq c \leq 3$, and when c is 2 or 3, each $R_{11}$ may be the same or different.

3. The aromatic amine derivative according to claim 1, wherein one or more selected from A and A' is a linkage group or a group comprising a group that interrupts conjugation between N atoms.

4. The aromatic amine derivative according to claim 3, wherein the linkage group or the group comprising a group that interrupts conjugation between N atoms is a linkage group or a group comprising a group represented by any of the following formulas:

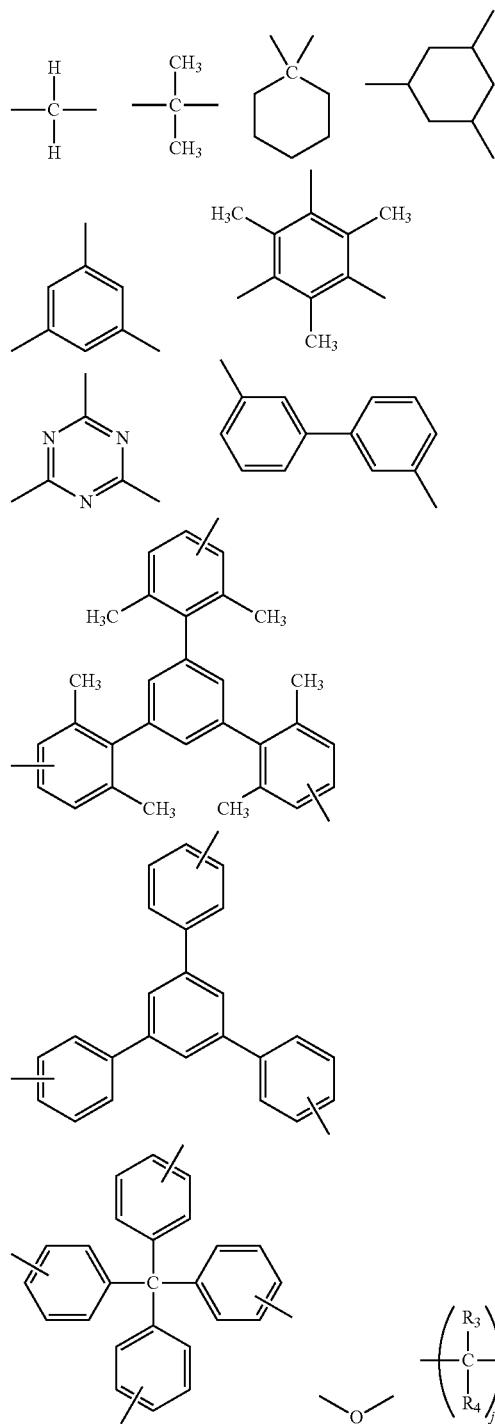

wherein $R_3$ and $R_4$ are independently a hydrogen atom, a methyl group, an ethyl group, a propyl group, an isopropyl group, a butyl group, an isobutyl group or a t-butyl group, and j is an integer of $2 \leq j \leq 20$, each $R_3$ may be the same or different, and each $R_4$ may be the same or different:

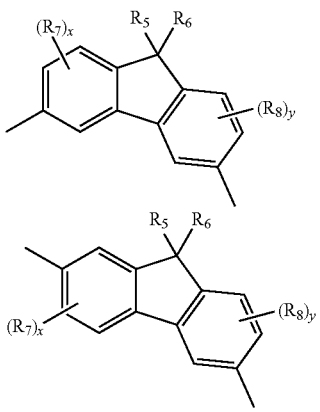

wherein $R_5$, $R_6$, $R_7$ and $R_8$ are independently a hydrogen atom, a linear or branched alkyl group including 1 to 20 carbon atoms, a linear or branched alkenyl group including 2 to 20 carbon atoms, a cycloalkyl group including 3 to 20 carbon atoms, a trialkylsilyl including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms;

$R_5$ and $R_6$ and/or $R_7$ and $R_8$ may be bonded to each other to form a saturated or unsaturated ring; and x and y are an integer of $1 \leq x \leq 3$ and an integer of $1 \leq y \leq 3$, respectively, and when x is 2 or 3, each $R_7$ may be the same or different, and when y is 2 or 3, each $R_8$ may be the same or different:

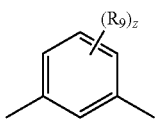

wherein $R_9$ is a hydrogen atom, a linear or branched alkyl group including 1 to 20 carbon atoms, a linear or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms; and z is an integer of $1 \leq z \leq 4$, and when z is 2, 3 or 4, each $R_9$ may be the same or different:

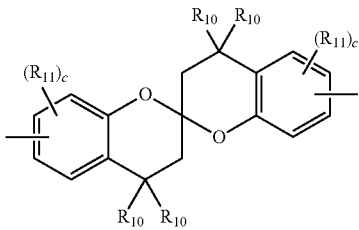

wherein $R_{10}$ and $R_{11}$ are independently a hydrogen atom, a linear or branched alkyl group including 1 to 20 carbon atoms, a linear or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms;

each $R_{10}$ and/or each $R_{11}$ may be bonded to each other to form a saturated or unsaturated ring; and c is an integer of $1 \leq c \leq 3$, and when c is 2 or 3, each $R_{11}$ may be the same or different.

5. The aromatic amine derivative according to claim 1, wherein P and/or Q is independently a group represented by the following formula (6) or (7):

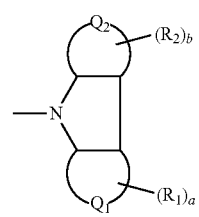

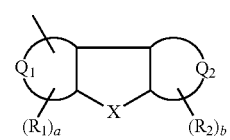

wherein $R_1$, $R_2$, a, b, $Q_1$ and $Q_2$ are as defined in the formula (4); and X is —O—, —S—, or —N($R_a$)—, and $R_a$ is as defined in the formula (4).

6. The aromatic amine derivative according to claim 1, wherein P and/or Q is independently a group represented by the following formula (8):

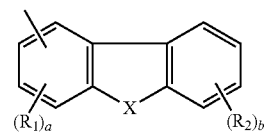

wherein $R_1$, $R_2$, a and b are as defined in the formula (4); and

X is —O—, —S—, or —N($R_a$)—, and $R_a$ is as defined in the formula (4).

7. The aromatic amine derivative according to claim 1, wherein P and/or Q is independently a group represented by the following formula (8-1) or (8-2):

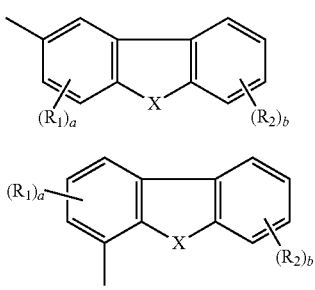
(8-1)

(8-2)

wherein $R_1$, $R_2$, a and b are as defined in the formula (4); and

X is —O—, —S—, or —N($R_a$)—, and $R_a$ is as defined in the formula (4).

8. The aromatic amine derivative according to claim 1, wherein at least one of $L_1$, $L_2$, A, A', B, C, P and Q is bonded to a group comprising a polymerizable functional group.

9. The aromatic amine derivative according to claim 8, wherein the group comprising a polymerizable functional group is a group comprising a vinyl group, a vinylidene group, a vinylene group or an ethynylene group represented by the following formula (i);

a group comprising a benzocyclobutene group represented by the following formula (ii);

a group comprising an N-maleimide group represented by the following formula (iii);

a group comprising a norbornenyl group represented by the following formula (iv);

a group comprising an acetylenyl group represented by the following formula (v); or (vi) a group comprising a functional group capable of cyclopolymerization or ring-opening polymerization selected from the group consisting of a group including a substituted or unsubstituted norbornene skeleton other than a group represented by the formula (iv), a group including a substituted or unsubstituted epoxy group or an oxetane group, a functional group including a lactone structure or a lactam structure, a cyclooctatetraene group, a 1,5-cyclooctadiene group, a 1,ω-diene group, an O-divinylbenzene group and a 1,ω-diyne group:

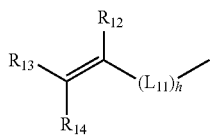
(i)

wherein $R_{12}$, $R_{13}$ and $R_{14}$ are independently a hydrogen atom, a fluorine atom, a substituted or unsubstituted linear or branched alkyl group including 1 to 20 carbon atoms, or a substituted or unsubstituted aryl group including 6 to 24 ring carbon atoms;

$L_{11}$ is a linkage group; and h is an integer of 0 or 1, and when h is 0, $L_{11}$ is a single bond:

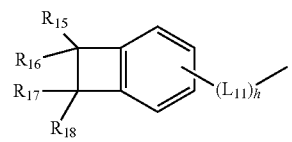
(ii)

wherein $R_{15}$, $R_{16}$, $R_{17}$ and $R_{18}$ are independently a hydrogen atom, a linear or branched alkyl group including 1 to 20 carbon atoms, a linear or branched alkenyl group including 2 to 20 carbon atoms, a cycloalkyl group including 3 to 20 carbon atoms, a trialkylsilyl group including an alkyl group including 1 to 20 carbon atoms, a triarylsilyl group including an aryl group including 6 to 24 ring carbon atoms, an alkylarylsilyl group including an alkyl group including 1 to 20 carbon atoms and an aryl group including 6 to 24 ring carbon atoms, an aryl group including 6 to 24 ring carbon atoms or a heteroaryl group including 5 to 24 ring atoms;

$R_{15}$ and $R_{16}$, $R_{16}$ and $R_{17}$, and/or $R_{17}$ and $R_{18}$ may be bonded to each other to form a saturated or unsaturated ring, $L_{11}$ is a linkage group; and h is an integer of 0 or 1, and when h is 0, $L_{11}$ is a single bond:

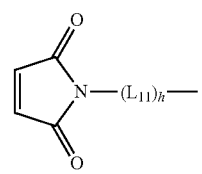
(iii)

wherein $L_{11}$ is a linkage group; and h is an integer of 0 or 1, and when h is 0, $L_{11}$ is a single bond:

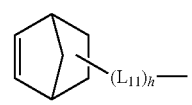
(iv)

wherein $L_{11}$ is a linkage group; and h is an integer of 0 or 1, and when h is 0, $L_{11}$ is a single bond:

(v)

wherein $R_{19}$ is a hydrogen atom, a substituted or unsubstituted linear or branched alkyl group including 1 to 20 carbon atoms, or a substituted or unsubstituted aryl group including 6 to 24 ring carbon atoms, $L_{11}$ is a linkage group; and h is an integer of 0 or 1, and when h is 0, $L_{11}$ is a single bond.

10. An organic electroluminescence device comprising one or more organic thin film layers including at least an emitting layer between a cathode and an anode, wherein at least one layer of the organic thin film layers comprises the aromatic amine derivative according to claim 1 and/or a polymer containing one or more types of repeating units derived from the aromatic amine derivative.

11. The organic electroluminescence device according to claim 10, wherein
the organic thin film layers comprise at least one layer of a hole-transporting layer and a hole-injecting layer, and
the at least one layer of a hole-transporting layer and a hole-injecting layer comprises the aromatic amine derivative and/or the polymer containing one or more types of repeating units derived from the aromatic amine derivative.

12. The aromatic amine derivative according to claim 1, wherein A is a hydrogen atom, or a substituted or unsubstituted aromatic hydrocarbon group including 6 to 25 ring carbon atoms.

13. The aromatic amine derivative according to claim 1, wherein A' is a single bond, or a substituted or unsubstituted aromatic hydrocarbon group including 6 to 25 ring carbon atoms.

14. The aromatic amine derivative according to claim 1, wherein B is a single bond, or a substituted or unsubstituted aromatic hydrocarbon group including 6 to 25 ring carbon atoms.

15. The aromatic amine derivative according to claim 1, wherein C is a single bond, or a substituted or unsubstituted aromatic hydrocarbon group including 6 to 25 ring carbon atoms.

16. The aromatic amine derivative according to claim 1, wherein P and Q are independently a group represented by the formula (4) or (5).

17. The aromatic amine derivative according to claim 1, wherein k is 1, and l is 0.

18. The aromatic amine derivative according to claim 1, wherein X is $-N(R_a)-$, and $R_a$ is a hydrogen atom, or a substituted or unsubstituted aryl group including 6 to 25 ring carbon atoms.

* * * * *